United States Patent
Scholz et al.

(10) Patent No.: US 10,421,776 B2
(45) Date of Patent: *Sep. 24, 2019

(54) METHOD FOR PREVENTING THE UNFOLDING OF A (POLY)PEPTIDE AND/OR INDUCING THE (RE-)FOLDING OF A (POLY)PEPTIDE

(71) Applicant: Leukocare AG, Martinsried/Munchen (DE)

(72) Inventors: Martin Scholz, Oberursel (DE); Jens Altrichter, Kavelstorf (DE); Kristina Kemter, Garching bei Munchen (DE)

(73) Assignee: Leukocare AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/995,130

(22) Filed: Jan. 13, 2016

(65) Prior Publication Data

US 2016/0215015 A1    Jul. 28, 2016

Related U.S. Application Data

(62) Division of application No. 14/123,168, filed as application No. PCT/EP2012/062645 on Jun. 28, 2012, now Pat. No. 9,321,848.

(30) Foreign Application Priority Data

Jun. 28, 2011  (EP) .................................... 11005280
Nov. 14, 2011  (EP) .................................... 11009019

(51) Int. Cl.
*C07K 1/113*   (2006.01)
*A61K 9/19*    (2006.01)
(Continued)

(52) U.S. Cl.
CPC .............. *C07K 1/1136* (2013.01); *A61K 9/08* (2013.01); *A61K 9/19* (2013.01);
(Continued)

(58) Field of Classification Search
CPC .................................................. C07K 1/1136
See application file for complete search history.

(56) References Cited

U.S. PATENT DOCUMENTS

2002/0103126 A1  8/2002  Rodel et al.
2003/0125234 A1  7/2003  Middaugh
(Continued)

FOREIGN PATENT DOCUMENTS

EP   1 491 208 A1   12/2004
EP   1 712 223 A1   10/2006
(Continued)

OTHER PUBLICATIONS

Carpenter et al., Freeze-Drying/Lyophilization of Pharmaceutical and Biological Products, Second Edition, CRC Press 2004 ISBD:13:978-0-203-02132-3, pp. 170-171.
(Continued)

*Primary Examiner* — Rosanne Kosson
(74) *Attorney, Agent, or Firm* — Gavrilovich, Dodd & Lindsey LLP

(57) ABSTRACT

The present invention relates to a method for preventing the unfolding of a (poly)peptide during drying and/or inducing the (re-)folding of a (poly)peptide after drying, comprising the step of embedding the (poly)peptide in an aqueous solution, wherein the solution comprises (i) at least three different amino acids; or (ii) at least one dipeptide or tripeptide; and wherein the solution is free or substantially free of (a) sugar; and (b-i) protein; and/or (b-ii) denaturing compounds; and (c) silanes.

12 Claims, 32 Drawing Sheets

Figure 1:
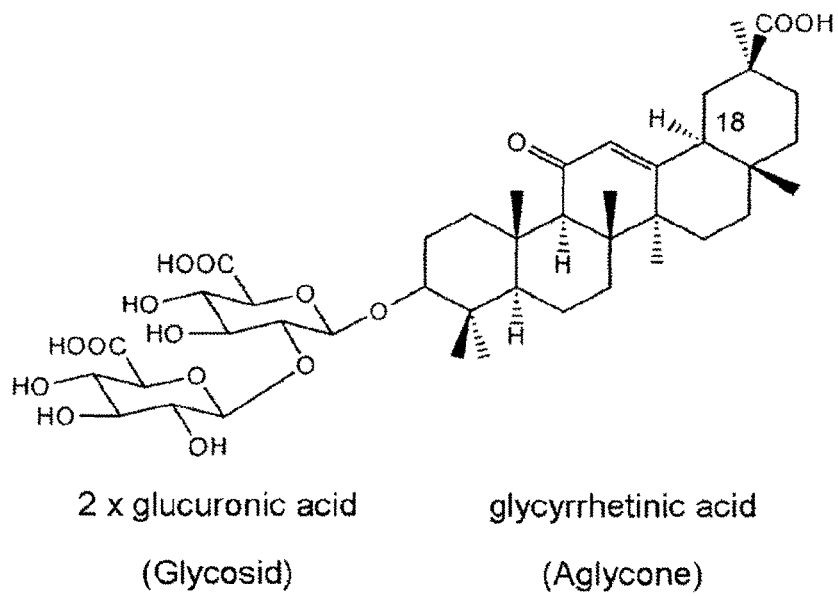

(51) Int. Cl.
| | |
|---|---|
| A61K 47/18 | (2017.01) |
| A61K 9/08 | (2006.01) |
| A61K 39/395 | (2006.01) |
| C07K 16/24 | (2006.01) |
| C07K 16/32 | (2006.01) |
| C12N 7/00 | (2006.01) |
| C07K 17/00 | (2006.01) |
| C12N 9/04 | (2006.01) |
| C12N 9/96 | (2006.01) |
| C07K 14/005 | (2006.01) |
| C07K 17/08 | (2006.01) |

(52) U.S. Cl.
CPC ...... *A61K 39/39591* (2013.01); *A61K 47/183* (2013.01); *C07K 1/113* (2013.01); *C07K 14/005* (2013.01); *C07K 16/241* (2013.01); *C07K 16/248* (2013.01); *C07K 16/32* (2013.01); *C07K 17/00* (2013.01); *C07K 17/08* (2013.01); *C12N 7/00* (2013.01); *C12N 9/0006* (2013.01); *C12N 9/96* (2013.01); *C07K 2317/94* (2013.01); *C12N 2710/10331* (2013.01); *C12N 2760/16151* (2013.01); *C12Y 101/01027* (2013.01)

(56) References Cited

U.S. PATENT DOCUMENTS

| | | |
|---|---|---|
| 2004/0022792 A1 | 2/2004 | Klinke et al. |
| 2007/0134199 A1 | 6/2007 | Frevert |
| 2008/0267979 A1* | 10/2008 | Lazar ............... C07K 16/303 424/174.1 |
| 2009/0291076 A1 | 11/2009 | Morichika et al. |

FOREIGN PATENT DOCUMENTS

| | | |
|---|---|---|
| EP | 1 977 763 A1 | 10/2008 |
| EP | 2 236 520 A1 | 10/2010 |
| EP | 2 236 617 A1 | 10/2010 |
| JP | 2003-507388 | 2/2003 |
| JP | 2004-515467 | 5/2004 |
| JP | 2006-528137 | 12/2006 |
| WO | 2001/12653 A1 | 2/2001 |
| WO | 2002/11695 A2 | 2/2002 |
| WO | 2009/049318 A2 | 4/2009 |
| WO | 2009049318 A2 | 4/2009 |
| WO | 2010112576 A1 | 10/2010 |
| WO | 2010115835 A2 | 10/2010 |

OTHER PUBLICATIONS

Lee et al., Molecular origins of surfactant-mediated stabilization of protein drugs, Adv. Drug Deliv. Rev. (2011).

Wang et al., Antibody Structure, Instability, and Formulation, Journal of Pharmaceutical Sciences, 96(1):1-26 (2007).

Weinzierl, Gerhard, Third Party Observations for European Patent Application No. EP12733061.1-1453 (Jan. 30, 2018).

Fennema, Owen R., Food Chemistry (2003), (translated into Chinese by Wang et al.) pp. 292-303.

Swarbrick, J., Encyclopedia of Pharmaceutical Technology (I) (translated into Chinese by Wang et al.) pp. 836-843.

Wang et al., Biochemistry (3rd edition) (2010), pp. 50-53.

Communication Pursuant to Rule 114(2) EPC, Observations by a Third Party, European Patent Office, Application No. 12733061.1; Jul. 25, 2018.

Mattern et al., "Formulation of Proteins in Vacuum-Dried Glasses. II. Process and Storage Stability in Sugar-Fee Amino Acid Systems", Pharmaceutical Development and Technology, 4(2), 199-208, 1999.

Tian et al., "Spectroscopic evaluation of the stabilization of humanized monoclonal antibodies in amino acid formulations", International Journal of Pharmaceutics, 2007, 335, 20-31.

Arakawa et al., "Biotechnology applications of amino acids in protein purification and formulations," Amino acids, vol. 33, pp. 587-605, Mar. 16, 2007.

Wang, Wei, "Instability, stabilization, and formulation of liquid protein pharmaceuticals," International Journal of Pharmaceutics, vol. 185, pp. 129-130, 1999, Abstract only; full article not submitted, only 1st 2 pp.

Weinzierl, G., "Third Party Observation," European Patent Office, EP Application No. 12733061.1, May 10, 2017.

Wang, Wei, "Instability, stabilization, and formulation of liquid protein pharmaceuticals", International Journal of Pharmaceutics, 1999, 185, pp. 129-188.

Matsubara, Hiroko, Japanese Patent Application No. 2014-517722, Mailing Date: Mar. 3, 2016.

Batra et al., "Circular dichroic study fo conformational changes in ovalbumin induced by modificatino of sulthydryl groups and disulfide reduction," J. Protein Chem., 8(5):609-617, 1989.

Schleifenbaum, A., International Search Report, European Patent Office, PCT/EP2012/062645, dated Sep. 27, 2012.

Liu et al., "Disulfide bond structures of IgG molecules Structural variations, chemical modifications and possible impacts to stability and biological function," mAbs, 4(1):17-23, Jan./Feb. 2012.

* cited by examiner 2 x glucuronic acid     glycyrrhetinic acid (Glycosid)     (Aglycone)

Mannitol-Albumin

Embedding

Figure 5A:
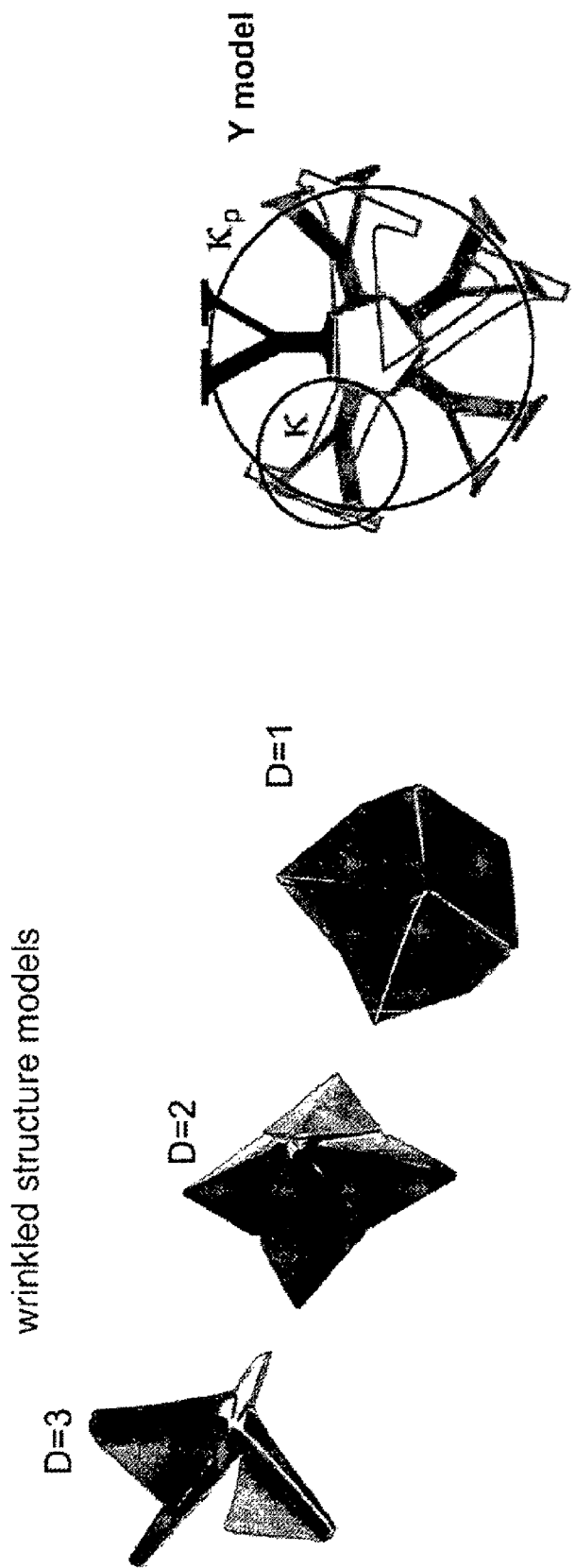

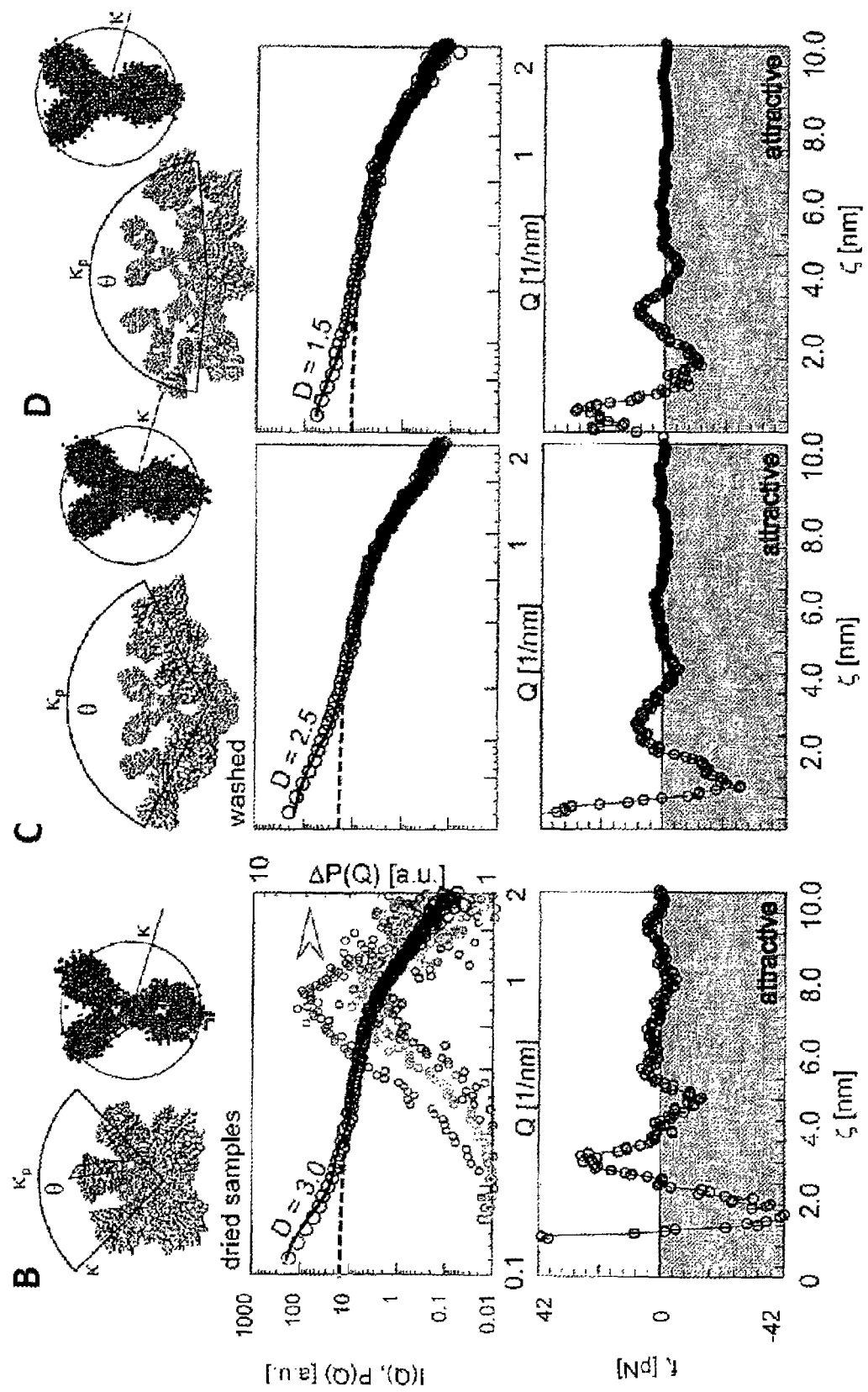
FIG. 5B-D

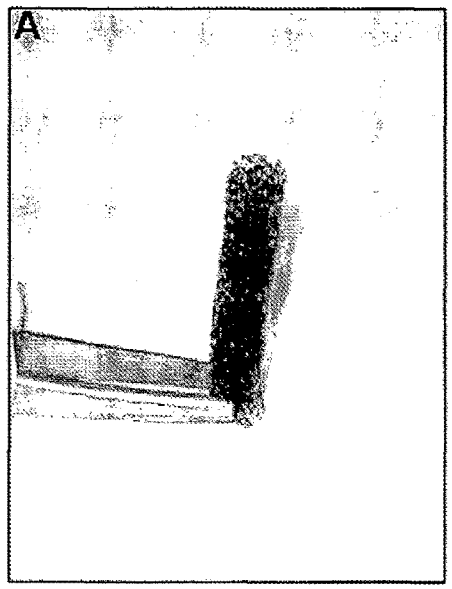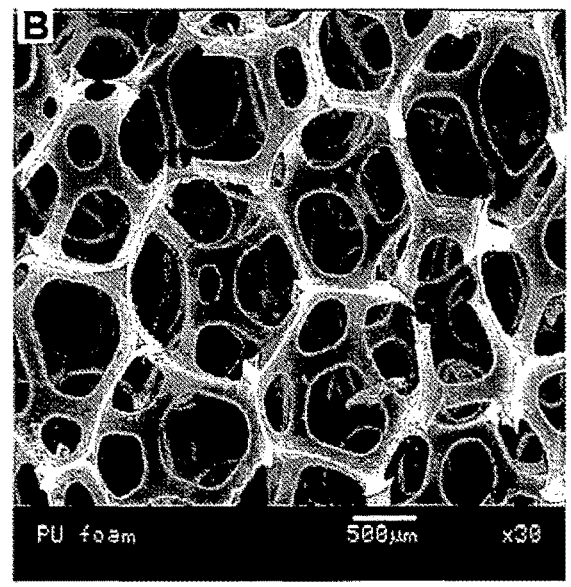
FIG. 7A
FIG. 7B
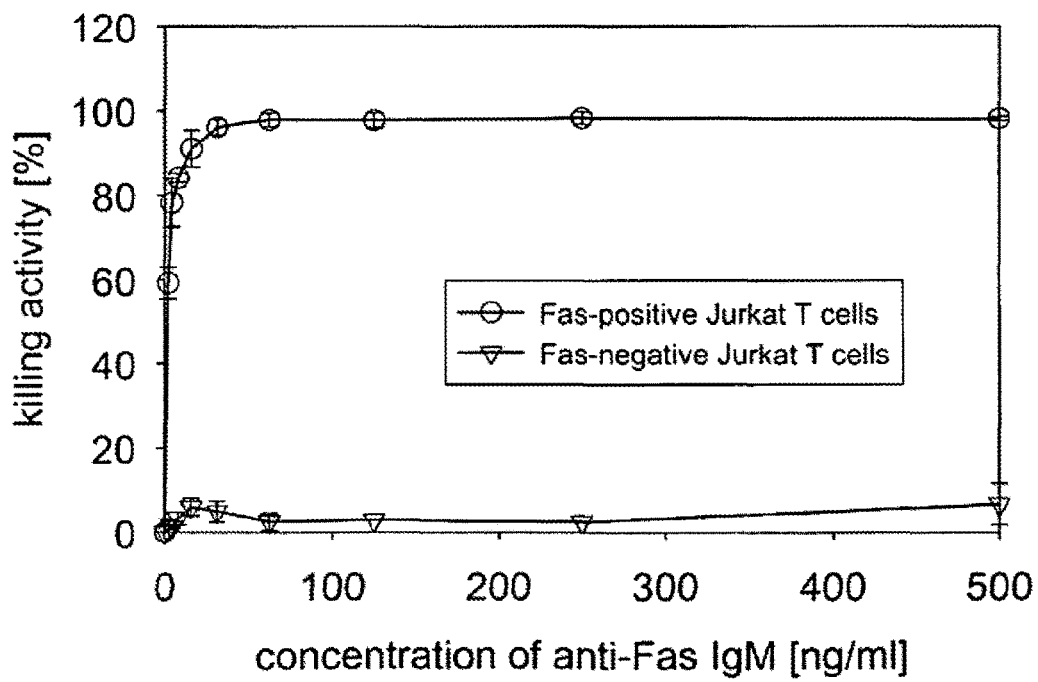
FIG. 7C

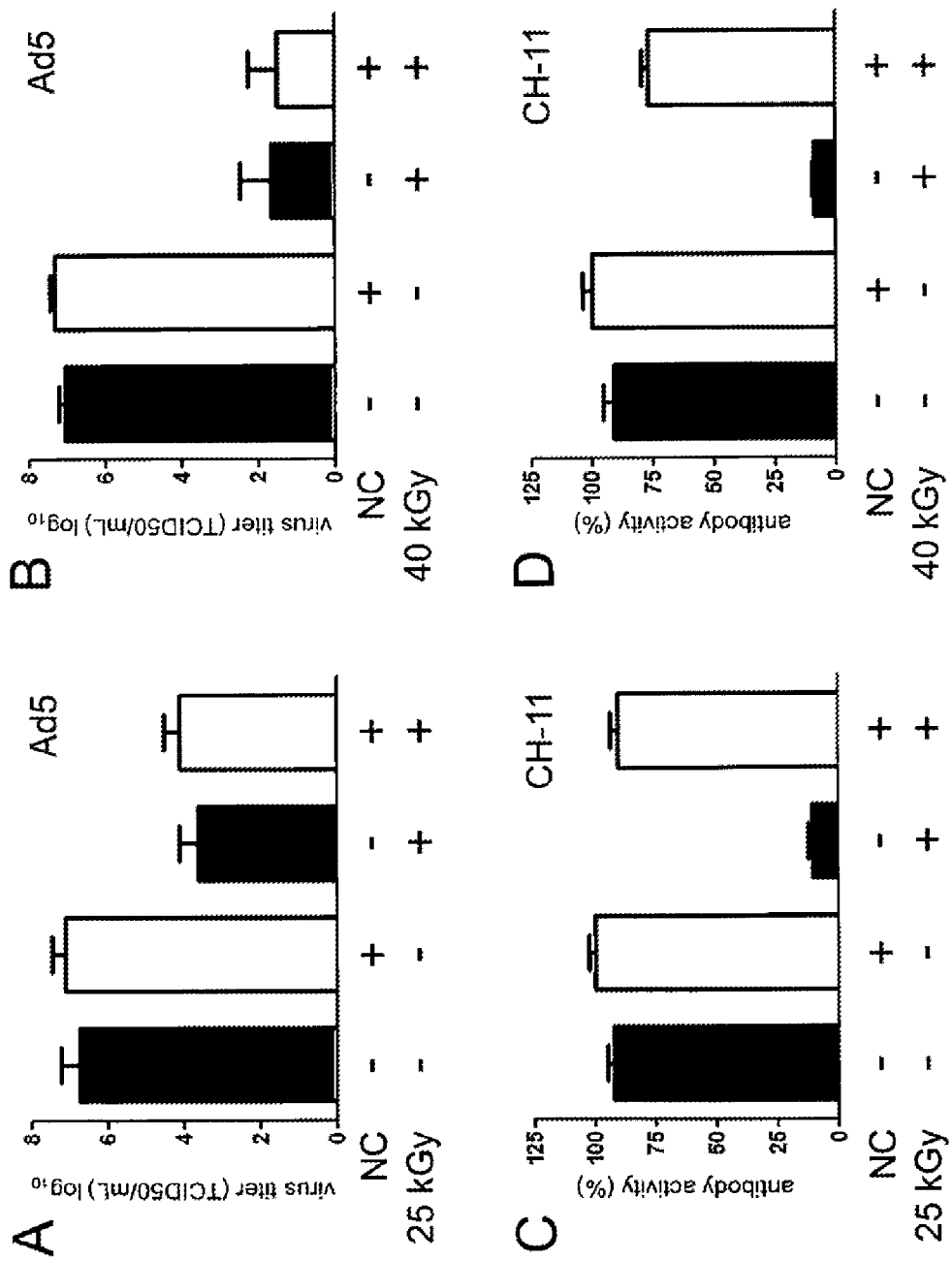
FIG. 8A-D

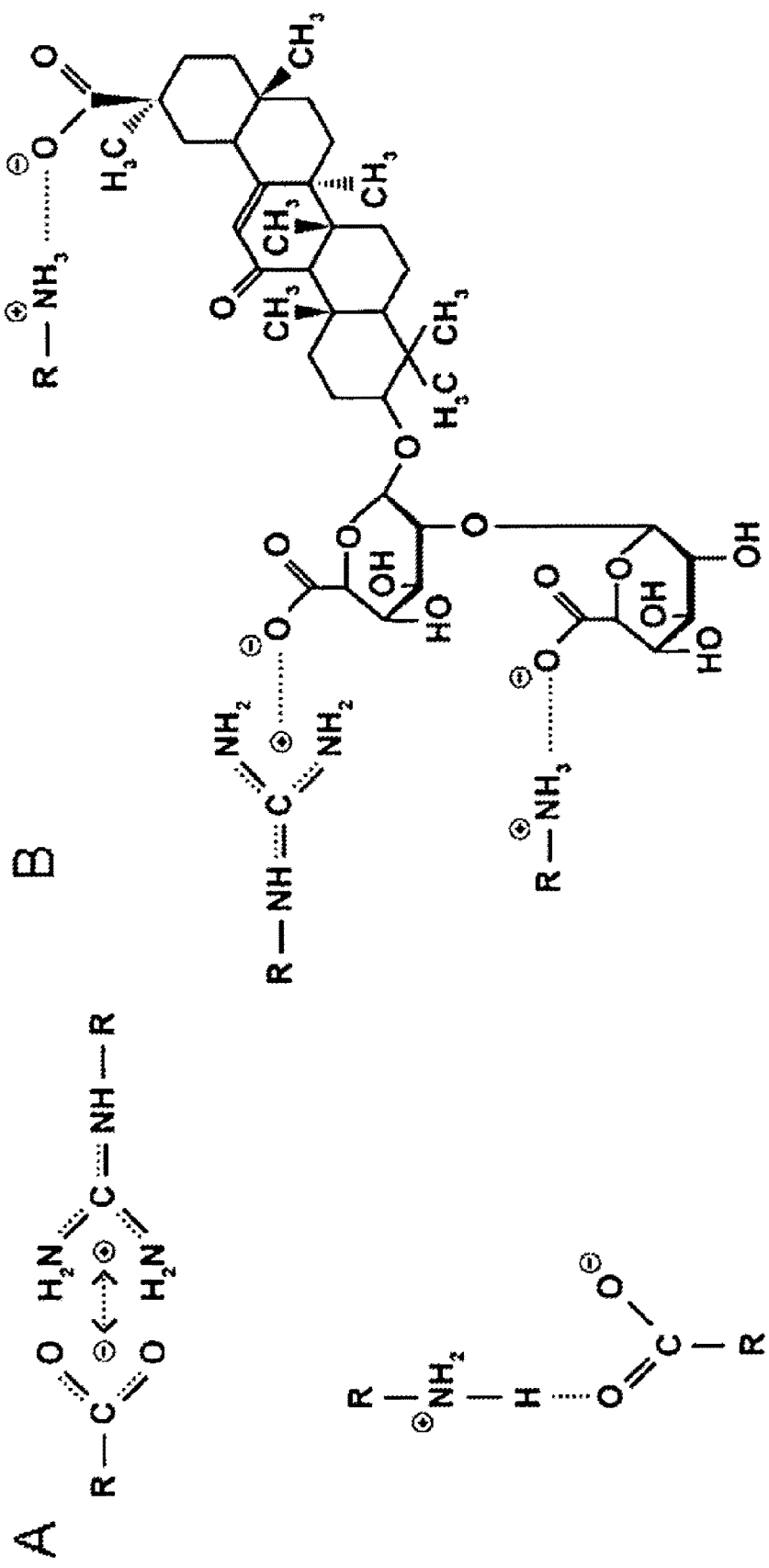
FIG. 9A-B

| calculated hemagglutinin concentration [ng/ml] | | 8000 | 4000 | 2000 | 1000 | 500 | 250 | 125 | 62,5 | 31,1 | 15,7 | 7,8 |
|---|---|---|---|---|---|---|---|---|---|---|---|---|
| Approach | Formulations | Type of stress | | | | | | | | | | | |
| A | Influenza A split vaccine H1N1 in the original formulation - liquid | No | | | | | | | | | | | |
| | Influenza A split vaccine H1N1 in the original formulation - lyophilized | Lyo | | | | | | | | | | | |
| B | Formulation 1 | No | | | | | | | | | | | |
| | | Lyo | | | | | | | | | | | |
| | | 40kGy | | | | | | | | | | | |
| | Formulation 2 | No | | | | | | | | | | | |
| | | Lyo | | | | | | | | | | | |
| | | 40kGy | | | | | | | | | | | |
| | Formulation 3 | No | | | | | | | | | | | |
| | | Lyo | | | | | | | | | | | |
| | | 40kGy | | | | | | | | | | | |
| | Formulation 4 | No | | | | | | | | | | | |
| | | Lyo | | | | | | | | | | | |
| | | 40kGy | | | | | | | | | | | |
| | Formulation Approaches A, B, C refer to different experimental settings with different hemagglutinin concentrations after rebuffering. GA: glycyrrhicic acid; Lyo: lyophilization; 40kGy: Irradiation dose.

METHOD FOR PREVENTING THE UNFOLDING OF A (POLY)PEPTIDE AND/OR INDUCING THE (RE-)FOLDING OF A (POLY)PEPTIDE

CROSS REFERENCE TO RELATED APPLICATIONS

This application is a divisional of U.S. patent application Ser. No. 14/123,168, filed Nov. 29, 2013, which is a U.S. National Stage Application filed under 35 U.S.C. § 371 based upon International Application No. PCT/EP2012/062645, filed 28 Jun. 2012, which claims priority to EP11005280.0, filed Jun. 28, 2011, and EP11009019.8, filed Nov. 14, 2011, the disclosures of which are incorporated herein by reference.

FIELD OF THE INVENTION

The disclosure relates to a method and compositions for preventing the unfolding of a (poly)peptide during drying and/or inducing the (re-)folding of a (poly)peptide after drying.

BACKGROUND

International application WO2005/007185 describes attempts to stabilize protein pharmaceuticals without the addition of the often used stabilizer human serum albumin (HAS). The stabilizing solution employed in WO2005/007185 instead comprises (i) a surface-active substance that is preferably a non-ionic detergent, i.e. a surfactant and (ii) a mixture of at least two amino acids, wherein the at least two amino acids are either glutamate and glutamine or aspartate and asparagine. The sole example testing the stabilizing effect of amino acids on their own (table 2) shows that in the absence of the surfactant polysorbat 80, no or only insubstantial stabilization—for a limited amount of time—of the protein solution was found.

In the international application WO 2008/000780, a spray dried powder containing protein is stabilized and has an advantageous aerodynamic behavior when at least 30% or at least 40% phenylalanine are included. Due to the addition of phenylalanine in the powder, the cohesive and adhesive properties of the powder are altered to reduce the interactions between the particles. By rendering the surface of the powder particles more hydrophobic, the aerodynamic properties of the powder are improved, thus rendering it more suitable for pulmonary application. The induction of folding or prevention of unfolding of proteins by a solution containing amino acids is not envisaged in WO 2008/000780.

European Patent application EP 1789019 describes spray dried powders of protein drugs for pulmonary application that are stabilized by the addition of novel oligosaccharide mixtures. International application WO 2010/151703 discloses a pharmaceutical composition for increasing the stability, reducing aggregation or reducing immunogenicity of a peptide or polypeptide, comprising at least one alkylglycoside.

In summary, it is crucial that the formulation scientist has a thorough knowledge of several factors: how to optimize the physical and chemical stability of the active ingredient; how, rationally, to include specific excipients in the formulation; how to obtain the optimum conditions for stability; how to prevent stability issues during up-scaling; and, finally, how to design a formulation that is suitable for the intended route of administration, that is, one that allows the absorption barrier to be overcome. The choice of excipients is often based on previous experience and on which excipients have been approved by authorities. Excipients are generally chosen (i) to ensure a successful end point for a preparation process, for example, allowing a dry powder to be obtained; (ii) to ensure that a liquid formulation remains at constant pH value; or (iii) to stabilize the protein against a certain production induced effect, for example adsorption. However, what may be useful for one protein can have detrimental effects on another.

The large size of proteins, their compositional variety and amphiphatic characteristics constitute specific behavior such as folding, conformational stability, and unfolding/denaturation. The structural differences among different proteins are so significant that generalization of universal stabilization strategies has not been successful to date. Despite the fact that a lot of research is invested into providing suitable methods to prevent unfolding and/or ensure proper folding of proteins during the exposure to the different forms of stresses, there are still problems with e.g. aggregation or increased unspecific immunogenicity due to protein misfolding. Even more, to date, the basic properties of a protein usually need to be examined prior to the development of a stable protein formulation. These properties include protein purity, pI as well as solubility and stability at different pH and in different buffer systems. With these data, protein formulation issues are usually addressed.

While it is desirable to keep the number of functional excipients as low as possible, for example in order to reduce instability resulting from solid state interactions, the vast amount of potential destabilizing effects often necessitates the addition of several excipients. Furthermore, for each protein of interest, cumbersome investigations are necessary to identify the respectively suitable excipients. Consequently, there is still a need to provide improved means to fold proteins or to prevent their unfolding during the exposure to the different forms of stresses upon the production and storage process that overcome these problems and are suitable for the majority of proteins and peptides, eliminating the need for individual investigations.

This need is addressed by the provision of the embodiments characterised in the claims.

BRIEF SUMMARY OF THE INVENTION

The present invention relates to a method for preventing the unfolding of a (poly)peptide during drying and/or inducing the (re-)folding of a (poly)peptide after drying, comprising the step of embedding the (poly)peptide in an aqueous solution, wherein the solution comprises (i) at least three different amino acids; or (ii) at least one dipeptide or tripeptide; and wherein the solution is free or substantially free of (a) sugar; and (b-i) protein; and/or (b-ii) denaturing compounds; and (c) silanes.

BRIEF DESCRIPTION OF THE DRAWINGS

FIG. 1: Formula of glycyrrhizic acid. (3β,18α)-30-hydroxy-11,30-dioxoolean-12-en-3-yl 2-O-β-D-glucopyranuronosyl-β-D-glucopyranosiduronic acid.

FIG. 2A-D: Wide-angle X-ray diffraction patterns and wide-angle X-ray powder diffraction patterns. (A) X-ray diffraction patterns of a non-embedded surface with four characteristic peaks for the used carrier material. (B) An embedded surface without glycyrrhizic acid (amorphous structure). (C) An embedded surface with glycyrrhizic acid (amorphous structure; embedding covers diffraction signal of the non-embedded carrier), and (D) X-ray powder diffraction patterns of freeze-dried antibody samples in the presence of embedding.

Figure 3A:
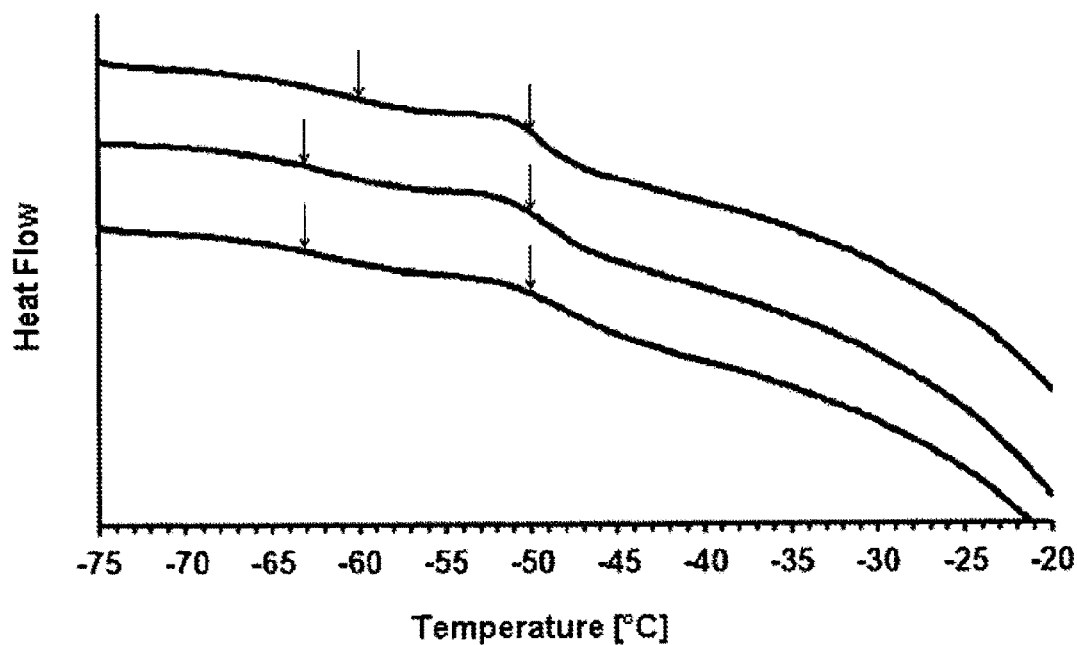
Figure 3B:
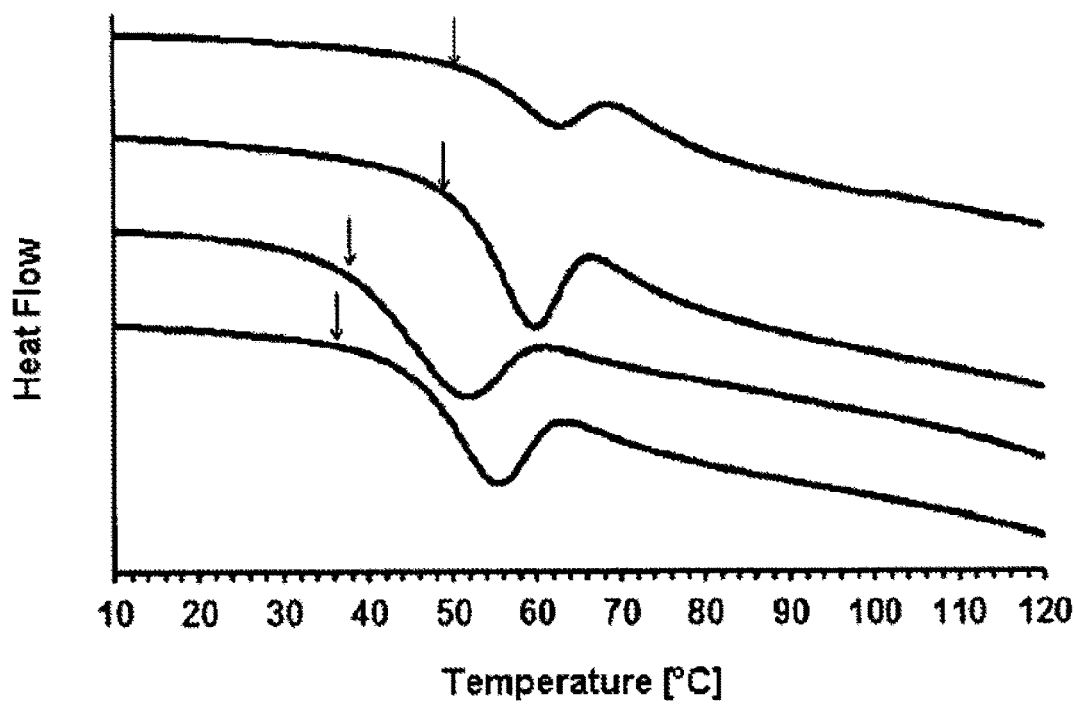

FIG. 3A-B: Thermograms of differential scanning calorimetry experiments. (A) Differential Scanning Calorimetry (DSC) of frozen solutions of embedding solution without glycyrrhizic acid (top curve), embedding with glycyrrhizic acid ([2 mg/ml], middle curve), and embedding with glycyrrhizic acid ([5 mg/ml], bottom curve) showing two glass transition points indicated by arrows (glycyrrhizic acid decreases the lower $T_g'$ of the amino acid solution by almost 2.5° C.), (B) DSC of antibody solids freeze-dried in the presence of embedding solution with and without β-irradiation. Embedding solution was mixed with 110 mg (top two curves) and 77 mg (bottom two curves) of antibody in a (ratio of 1.2:1) prior to freeze-drying and left untreated (first and third curve from top) or β-irradiated (first and third curve from bottom) before DSC measurements. Glass transition points are indicated by arrows.

Figure 4A:
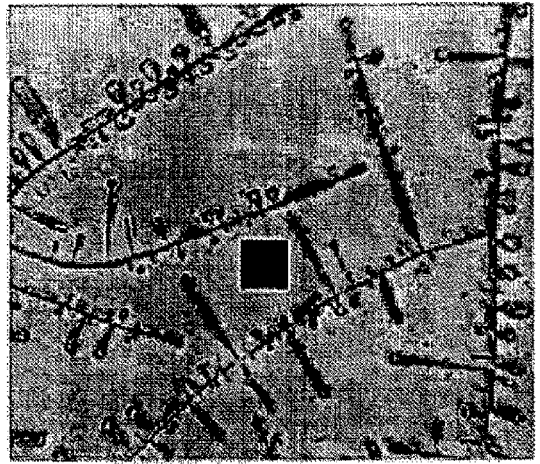
Figure 4B:
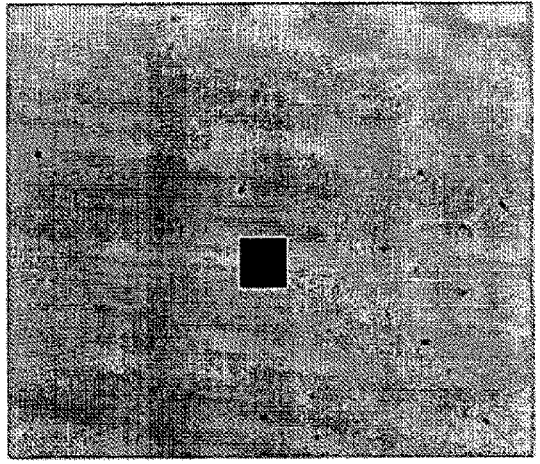
Figure 4C:
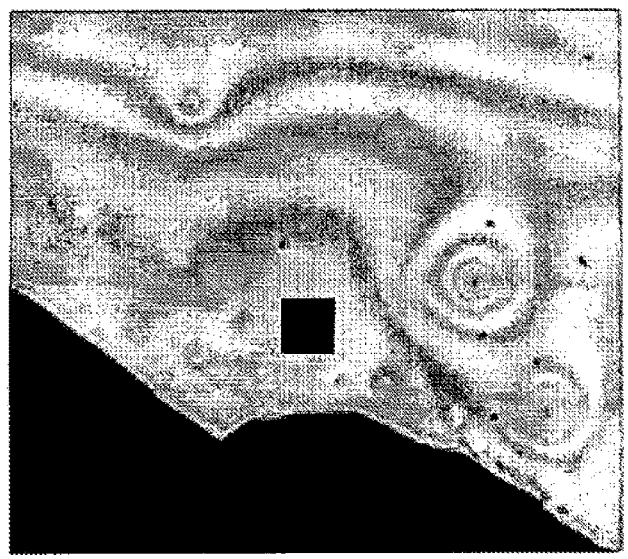

FIG. 4A-C: Spectral reflectance analyses of embedding on Si. (A) Photomicrographs of a dried mannitol-albumin mixture (crystalline) and (B) nano-coating (amorphous) on Si. (C) Representative "rainbow" effects of nano-coating in the nanometer range.

Figure 15:
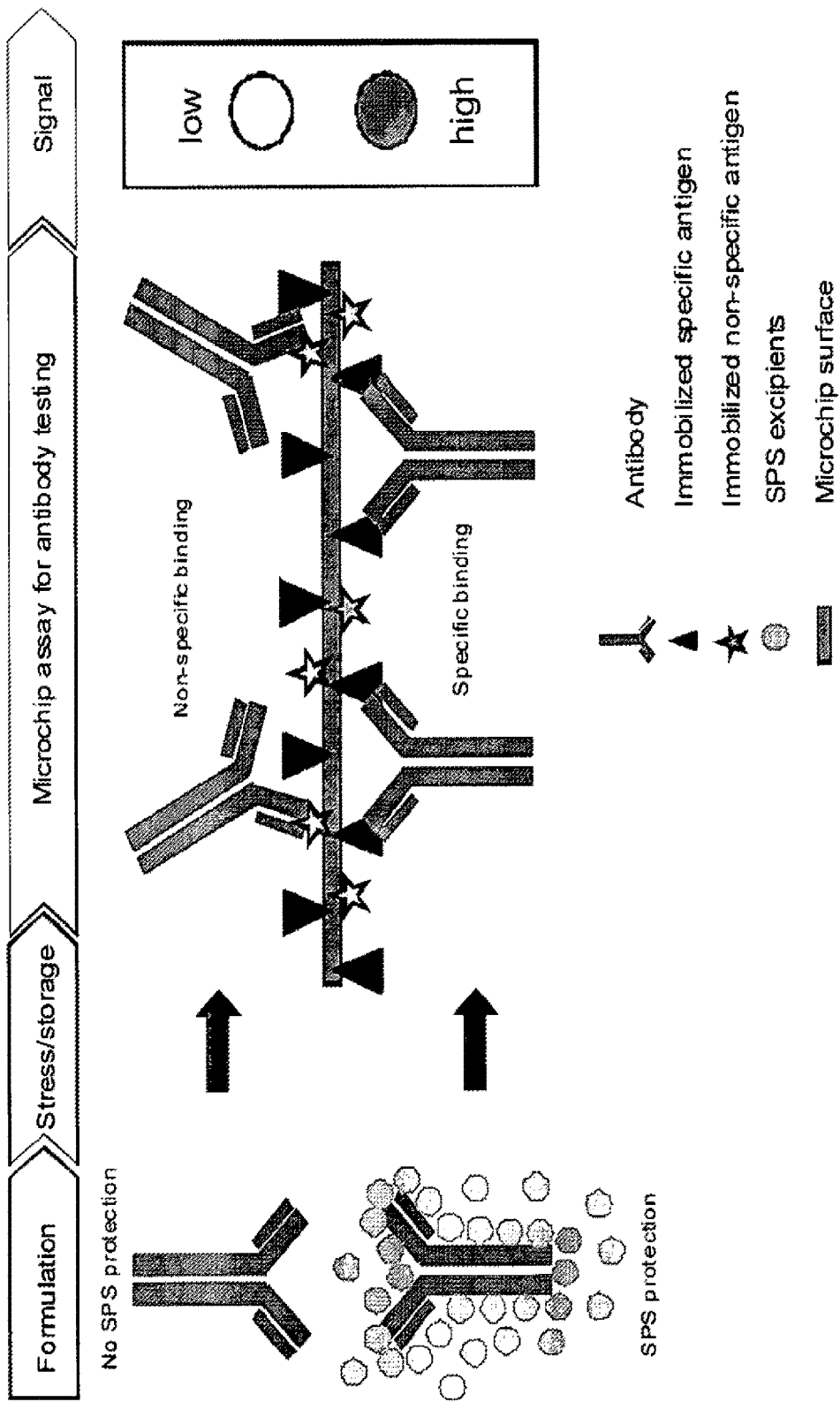

FIG. 5A-D: SAXS images of functionalized open porous polyurethane foam. (A) The self-similarity of the IgM molecule and the impact on the fractal dimension can be depicted by the geometrically wrinkled structure models on the top of the figure, wherein the fractal dimension D=3 counts for a closed object. Physically, the IgM is entirely dehydrated, and a decrease in the fractal dimension D leads to the opening of the models. The latter may be anticipated by an entirely open IgM unit (rehydrated). Additionally, the self-similarity of the IgM molecule at different length scales, based on its characteristic Y-like structure, is depicted in the Y model. With D=3, the mean diameter of the IgG arm, κ, is smaller than the diameter $\kappa_p$. For D=2, both radii are equivalent, and for D=1, the equation $2\kappa=\kappa_p$ is applicable. IgG structural models are given by gray bead models. Green bead models: IgM is built as a pentamer of IgG subunits. In the upper panel, large red open circles correspond to background-corrected scattering intensities. Dashed lines indicate analytic form factors. Black lines give the full fit of SAXS data based on the gray IgG structural models and their mean forces. In the lower panel, small open connected circles indicate corresponding mean forces. (B) Background-corrected scattering intensities of dried samples *PU-$IgM_{Fas}$, PU-$IgM_{Fas}$-NC, and *PU-$IgM_{Fas}$-NC (the asterisk indicates β-irradiation). The relative change of their form factors ΔP(Q) with respect to PU-$IgM_{Fas}$ are given (small red, gray, and black open circles, respectively). For D=3, the mean forces hold a pronounced corrugation and are given as a multitude of kT, where k is the Boltzmann constant and T is the system temperature. (C) The sample PU-$IgM_{Fas}$ was rehydrated. The system's fractal dimension decreased to 2.5. The corrugation of the corresponding mean force decreased. (D) The rehydrated samples of *PU-$IgM_{Fas}$ could not be analyzed because of the lack of measurable signals whereas the *PU-$IgM_{Fas}$-NC samples exhibited a fractal dimension of 1.5 and a decreased corrugation of the corresponding mean force.

FIG. 6A-C: Preservation of $IgM_{Fas}$ epitope recognition after embedding by ELISA. (A/B) Binding of immobilized $IgM_{Fas}$ ((A) CH-11; (B) LO-MM-3) to graded amounts of recombinant human Fas antigen fragment (hFas::Fc) after β-irradiation and/or embedding. (C) Binding of immobilized $IgM_{Fas}$ to graded amounts of epitope peptide after β-irradiation and/or embedding. For $K_D$ determination, data were fitted to a 1:1 Langmuir binding model.

FIG. 7A-E: Apoptosis induction by PU-$IgM_{Fas}$. Macroscopic (A) and raster electron microscopic (B) photography of PU foam samples. PU foam samples were cut into cylindrical pieces (here: 3 $cm^3$) for the apoptosis induction assays. The pore diameter of open porous PU foam was approximately 1.5-2 mm. (C) Effects of PU-$IgM_{Fas}$ containing different concentrations of anti-Fas IgM on the induction of apoptosis in Fas-positive and Fas-negative Jurkat T-cells. (D/E) Ex vivo detection of apoptosis in neutrophils from severely injured patients by fluorescent staining ((D), condensation of nuclei) and by propidium iodide staining and flow cytometry ((E), DNA-strand fragments).

FIG. 8A-D: Adenovirus type 5 (Ad5) infectivity assay. (A/B) Ad5 samples were β-irradiated at 25 kGy (A) and 40 kGy (B) with and without embedding. The titers of infective virus particles before and after irradiation are shown. (C/D) In the same setting an IgM antibody was irradiated. The relative antigen binding capacity before and after irradiation is shown.

FIG. 9A-C: Proposed mechanism of the embedding solution. (A) Interactions between the multiple functional groups of amino acids in solution and particularly during drying. (B) Interactions between basic functional groups of the amino acids with the anionic carboxyl groups within the glycyrrhizic acid molecule, triggering the formation of a highly amorphous state. (C) Sequential substitution of the stabilizing hydrogen bonds between protein and water molecules (hydrate shell) by stabilizing molecular interactions between protein, amino acids, and glycyrrhizic acid in the dried and amorphous states.

FIG. 10A-B: (A) SDS-PAGE; Lane 1: OVA control, Lane 2: OVA degraded, Lane 3: (OVA+inventive solution) SD, Lane 3: Marker (Pageruler™); (B) CD spectra of OVA control, OVA degraded and (OVA+inventive solution) SD (spectra of protein only).

FIG. 11: Enhancement of fluorescence intensity of ANS on binding to OVA.

FIG. 12: Fluorescence intensity of OVA control and (OVA+inventive solution) SD (spectra of protein only) after binding with ANS.

FIG. 13A-B: TNF-α binding by a therapeutic anti-TNF-α antibody. Antibody binding was analyzed with the protein microchip (UNIchip®). (A) Time course of TNF-α binding ($t_0$ refers to freshly reconstituted antibody; $t_6$ refers to reconstituted antibody after 6 weeks and stored at 40° C.) and of the loss of fluorescence intensity signals overtime. Error bars represent the Mean+/−SD from four spots (representative data of two independent microchip assays). Bovine serum albumin (BSA) was used as negative control and did not show any binding activity to TNF-α. *$p<0.05$ or **$p<0.005$ between $t_0$ and $t_6$. (B) Loss of fluorescence intensity as shown for four spots (20 fmol antigen/spot) at day 0 and after six weeks. Bright fluorescence (left) and medium fluorescence (right) is shown.

FIG. 14: Stabilization of a therapeutic anti-TNF-α antibody. Antibody binding intensity values to the specific antigen after lyophilization with or without SPS formulation versus anti-TNF-α antibody control (liquid storage) are shown. Error bars represent the Mean+/−SD from four spots (representative data of two independent microchip assays) printed in the concentration of 20 fmol/spot. *$p<0.05$ versus group "anti-TNF-α antibody $t_6$"; **$p<0.005$ versus group "anti-TNF-α antibody$t_0$".

FIG. 15: Schematic representation of specific and non-specific binding of antibodies to the microchip and the resulting difference in signaling intensity.

Figure 16:
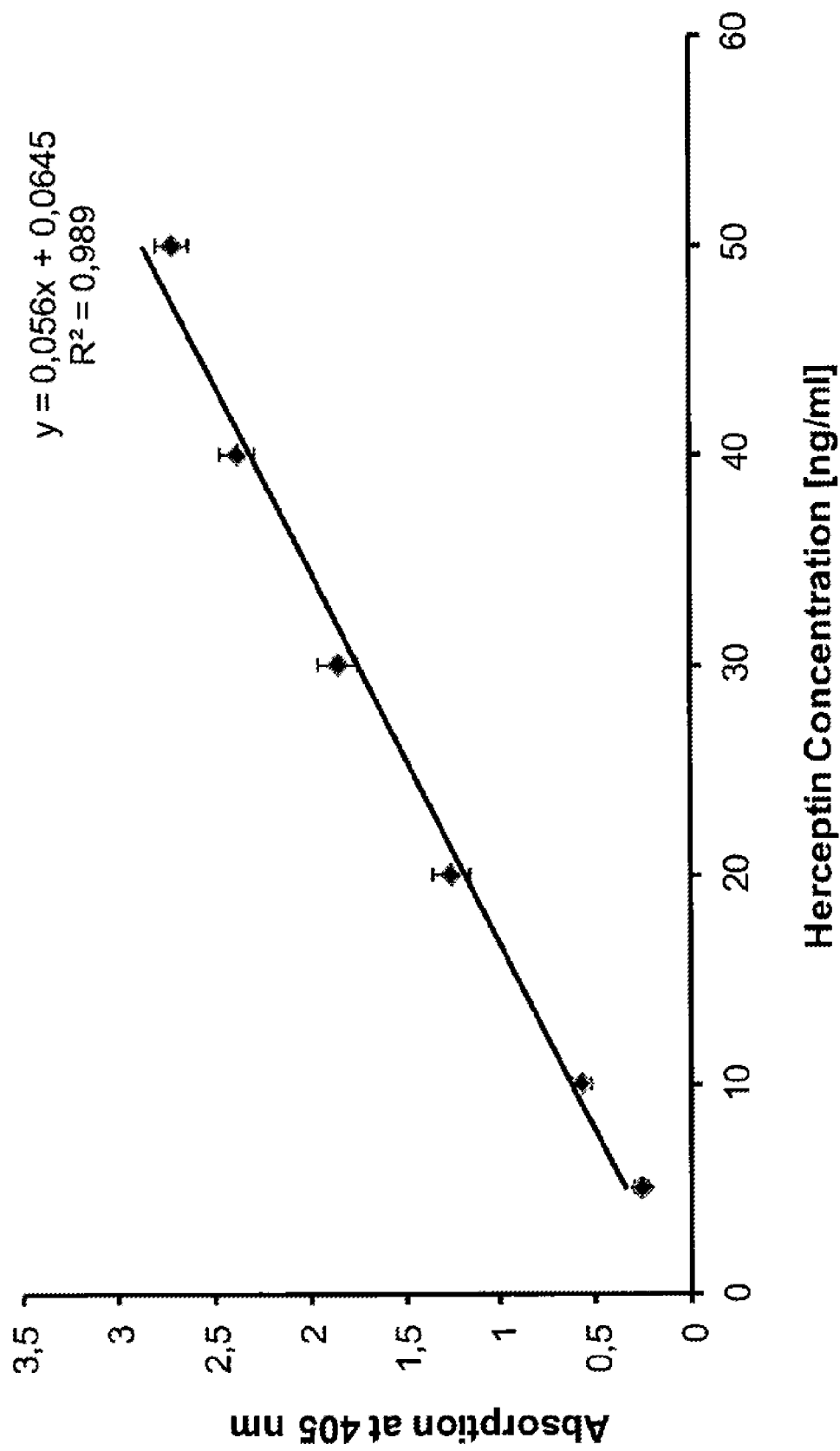

FIG. 16: Establishment and Validation of an anti-ErbB2-ELISA. The assay comprises coupling of ErbB2 antigen to the microtiter plates, blocking of free protein binding sites on the plate using a blocking buffer, binding of the anti-ErbB2 antibody to ErbB2 antigen, binding of the detection antibody and enzymatic conversion of the alkaline phosphatase substrate p-nitrophenylphosphat. The readout is a time and concentration dependent color reaction monitoring the amount of bound (functional) anti-ErbB2 antibody at 405 nm. The relationship between the responses to increasing concentrations of anti-ErbB2 antibody was demonstrated to be continuous and reproducible. Between-run precision was tested with n=10 independent experiments using freshly reconstituted therapeutic anti-ErbB2 antibody. A linear dependency of the concentration response relationship for a anti-ErbB2 antibody concentration range between 5 and 50 ng/mL with a goodness of fit $R^2=0,989$ and only small standard deviations was found.

Figure 17:
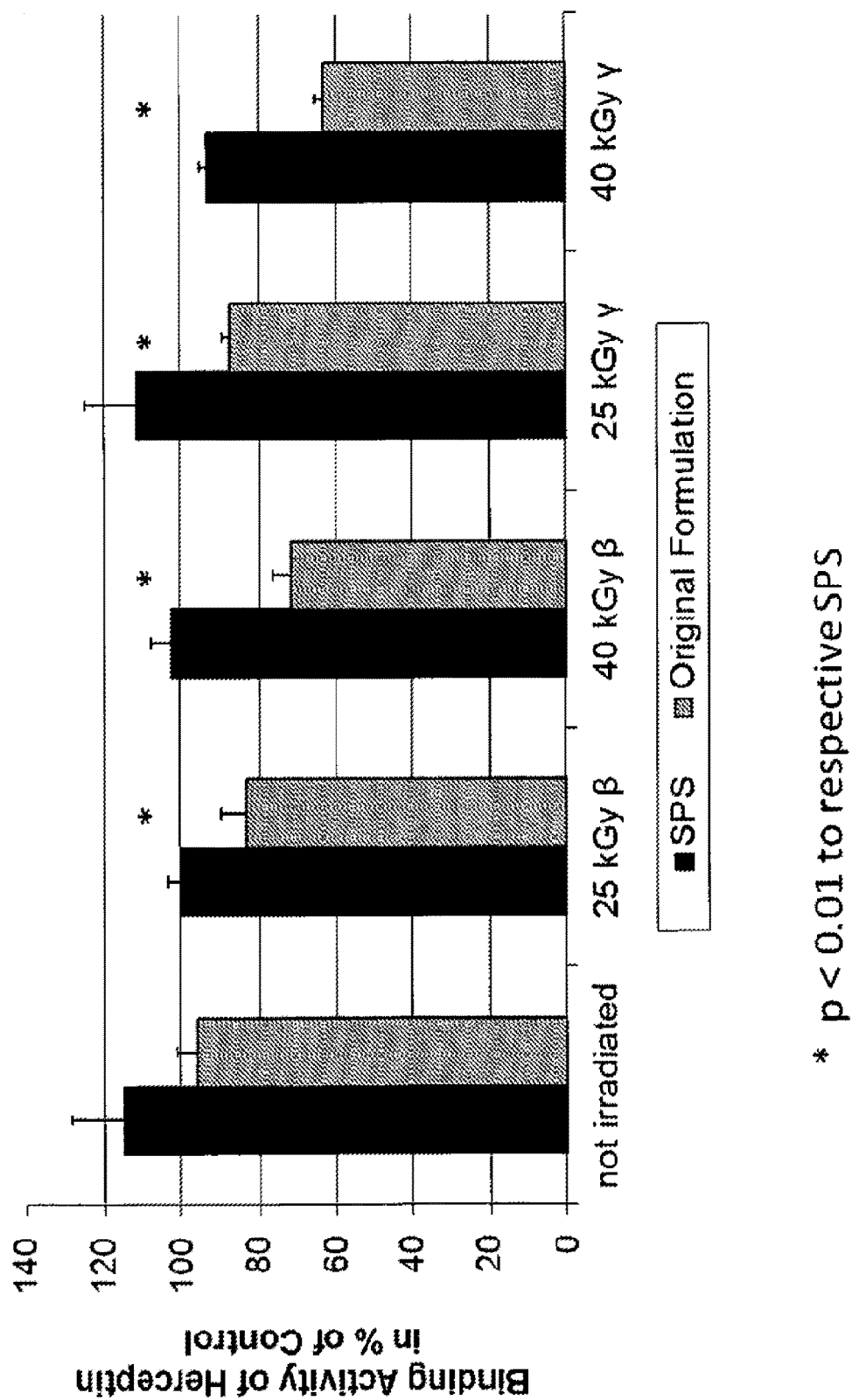

FIG. 17: Functional ELISA data. A comparison of the calculated binding activities of anti-ErbB2 antibodyin % of the control in the reconstituted lyophilized anti-ErbB2 antibody formulation with and without exposure to β- and γ-irradiation of different doses is depicted. Freshly reconstituted anti-ErbB2 antibody in the original supplier formulation (control) at 20 ng/mL served as reference (100%). All experiments to monitor the functionality of anti-ErbB2 antibody following lyophilization and irradiation were performed with reconstituted anti-ErbB2 antibody at 20 ng/mL. All experiments were done at least in triplicates and data are depicted as Mean±SD. SigmaStat 3.0 was used to conduct nonparametric analyses using Mann-Whitney Rank Sum Test. Differences were considered significant at $p<0.01$. Calculated significances are emphasized by asterisks.

Figure 18A:
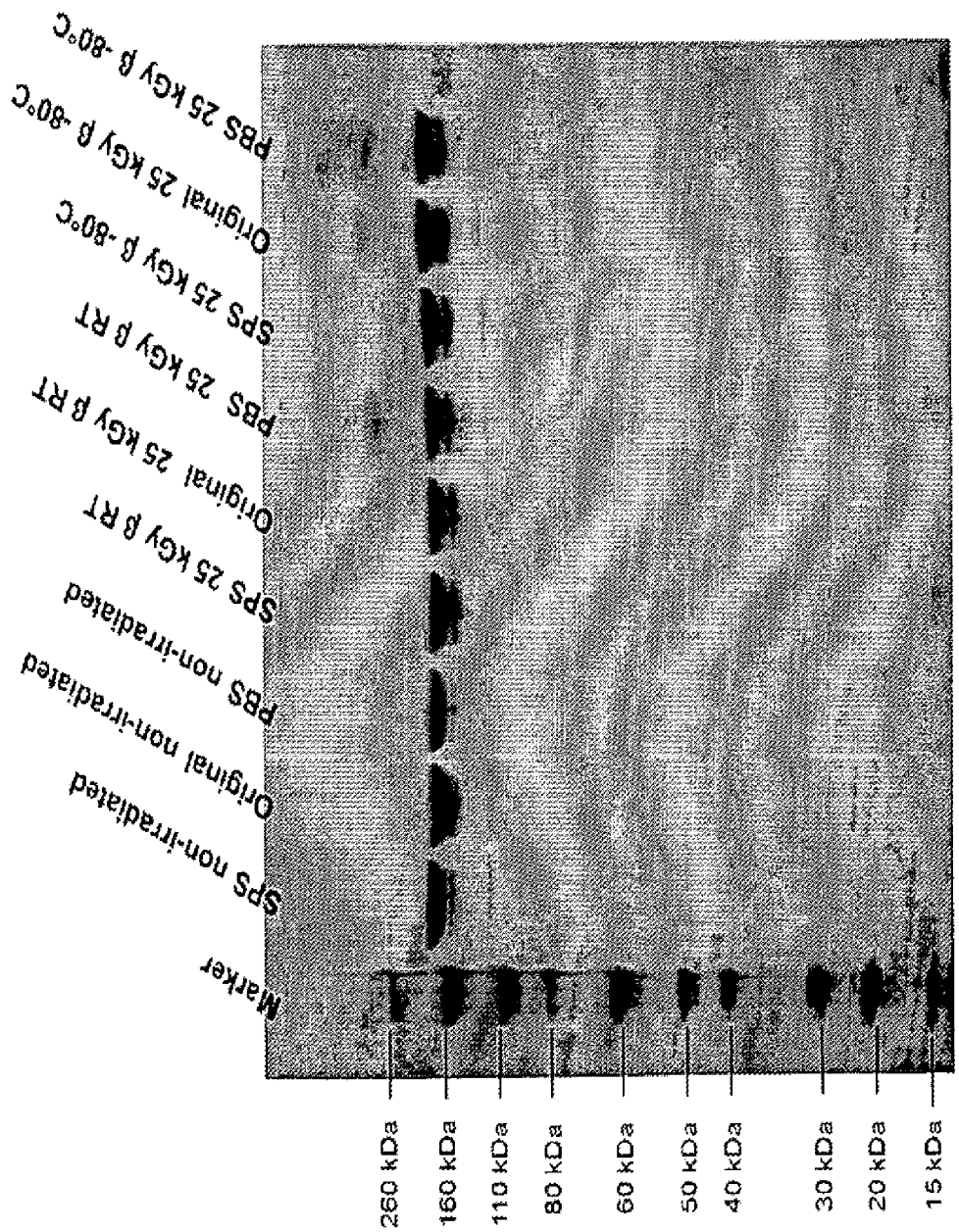
Figure 18B:
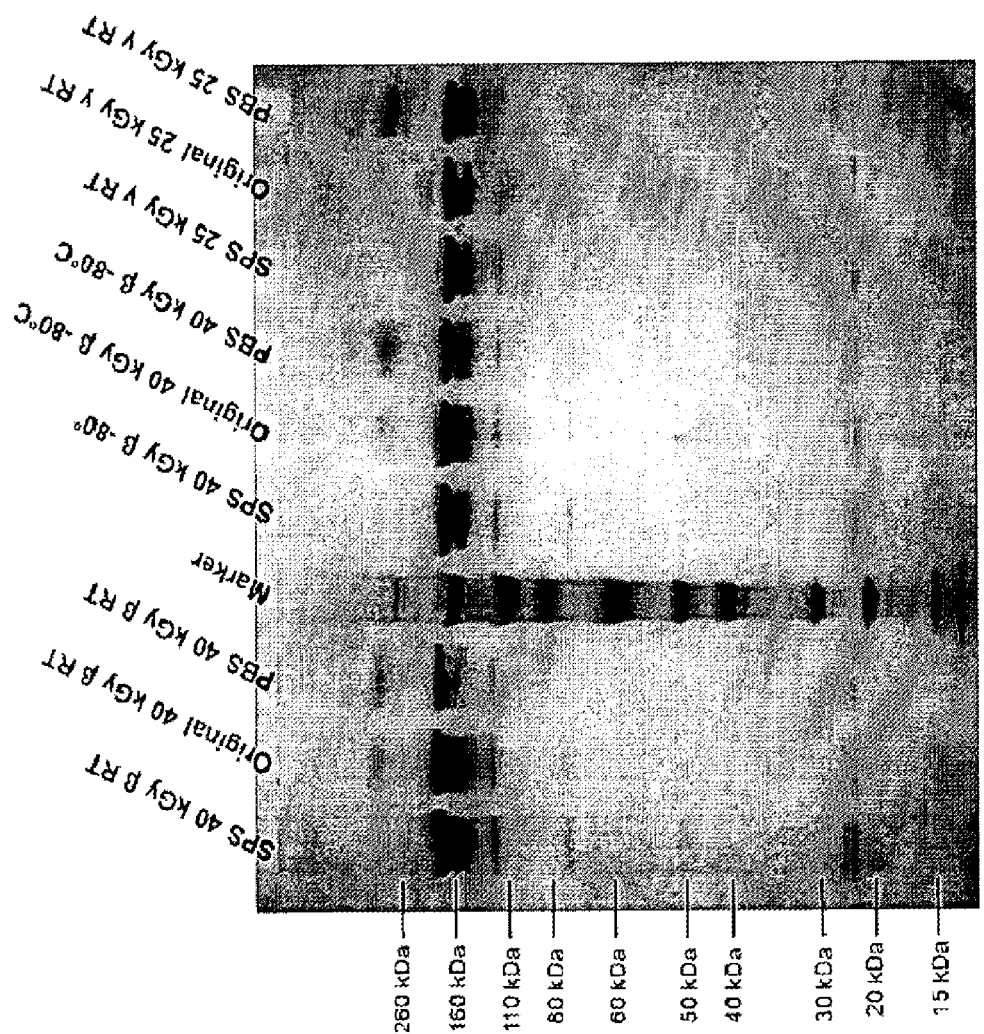
Figure 18C:
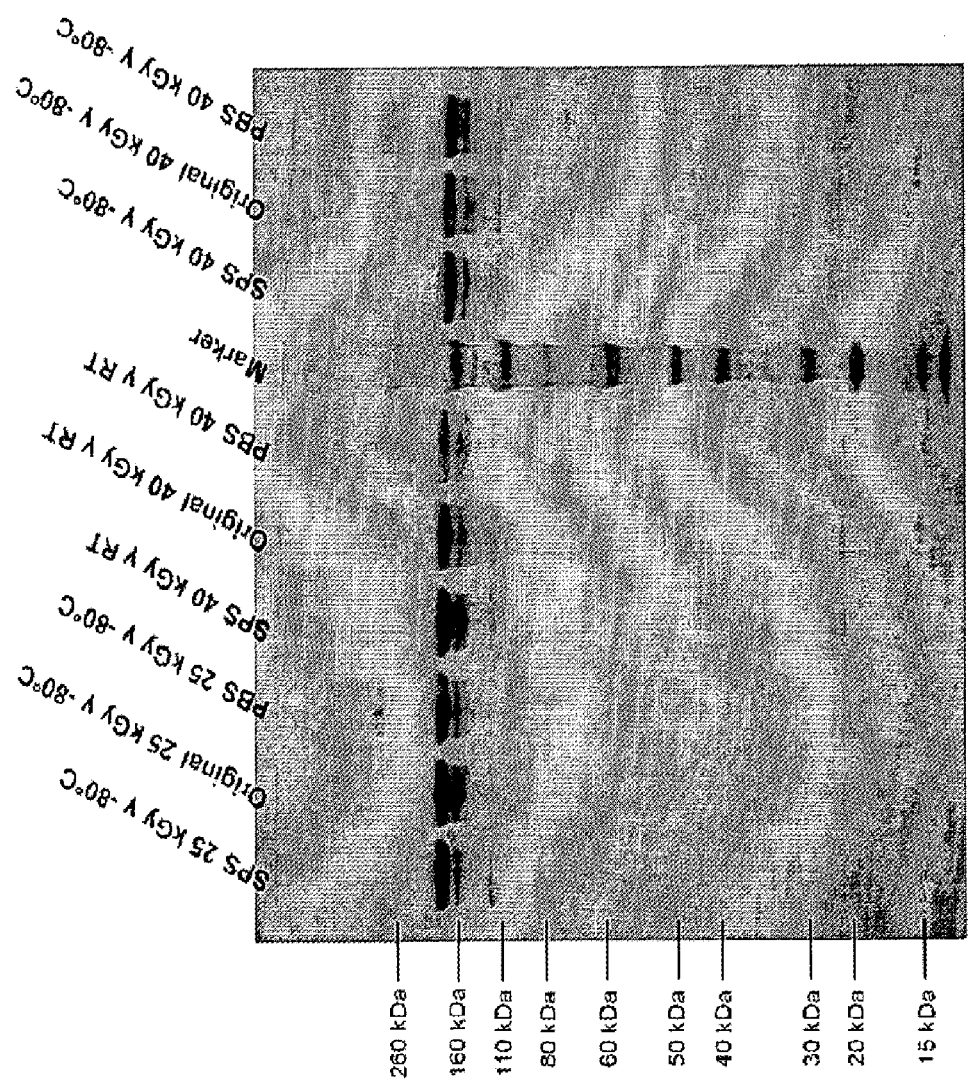

FIG. 18A-C: Non-reducing SDS-PAGE gels of anti-ErbB2 antibody after lyophilization and subsequent irradiation with different protocols. (A) A molecular weight standard was analyzed on each gel to determine the molecular weight of the detected bands (Marker). Concerning the formulations the samples are loaded for each treatment condition in the following order: SPS, Original supplier Formulation and PBS. The treatment conditions from the left to the right are non-irradiated, 25 kGy β-irradiation, 40 kGy β-irradiation, 25 kGy γ-irradiation and 40 kGy γ-irradiation. (B-C) For the corresponding doses and kinds of irradiation discriminations between irradiation at room temperature (RT) and at −80° C. are shown. The predominant bands in the gel correspond to the intact IgG1 antibody at a molecular weight of approximately 160 kDa. In the irradiated samples without SPS formulation the intensities of these bands are decreasing to the same extent as the intensities of the bands corresponding to covalent aggregates above 260 kDa are increasing. Traces of degradation in all lanes are a consequence of the sample preparation for the gel with the following molecular weight assignment of the bands: 110 kDa—heavy chain dimer, between 80 and 60 kDa—heavy/light chain dimer, 50 kDa—heavy chain, between 30 and 20 kDa —light chain.

Figure 19:
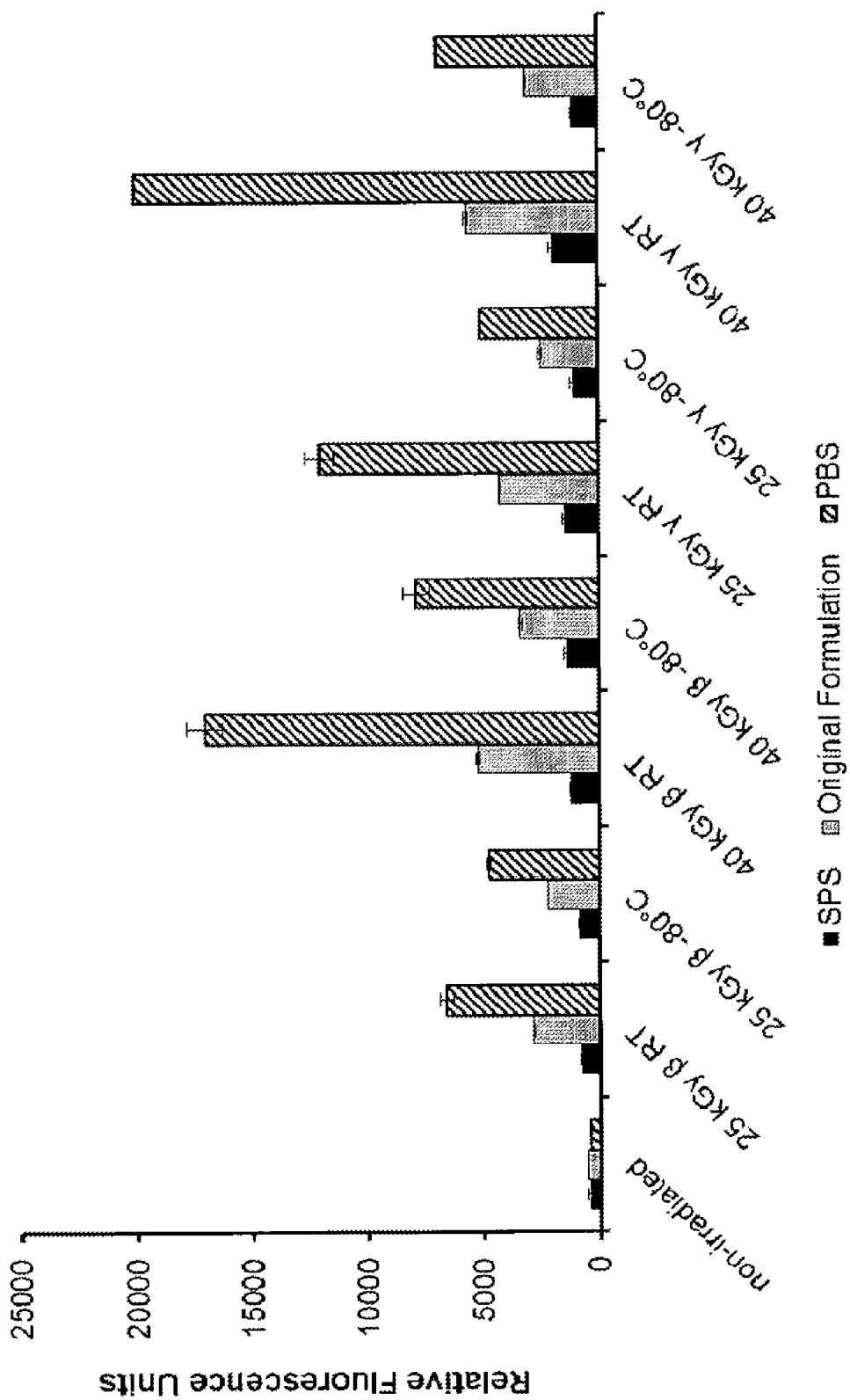

FIG. 19: Fluorescence-based microplate aggregation assay. The results from the semi-quantitative ProteoStat® fluorescence-based aggregation assay substantiate the patterns of the non-reducing SDS-PAGE in FIG. 19. Only traces of aggregates were measured in the non-irradiated samples. In all irradiated SPS-formulated samples only a slight increase in aggregation was detected. The propensity for aggregation increases in the order of formulations: SPS<<Original formulation<PBS. The amount of measured aggregates depends on the dose and kind of irradiation and decreases with irradiation temperature at various extends.

Figure 20A:
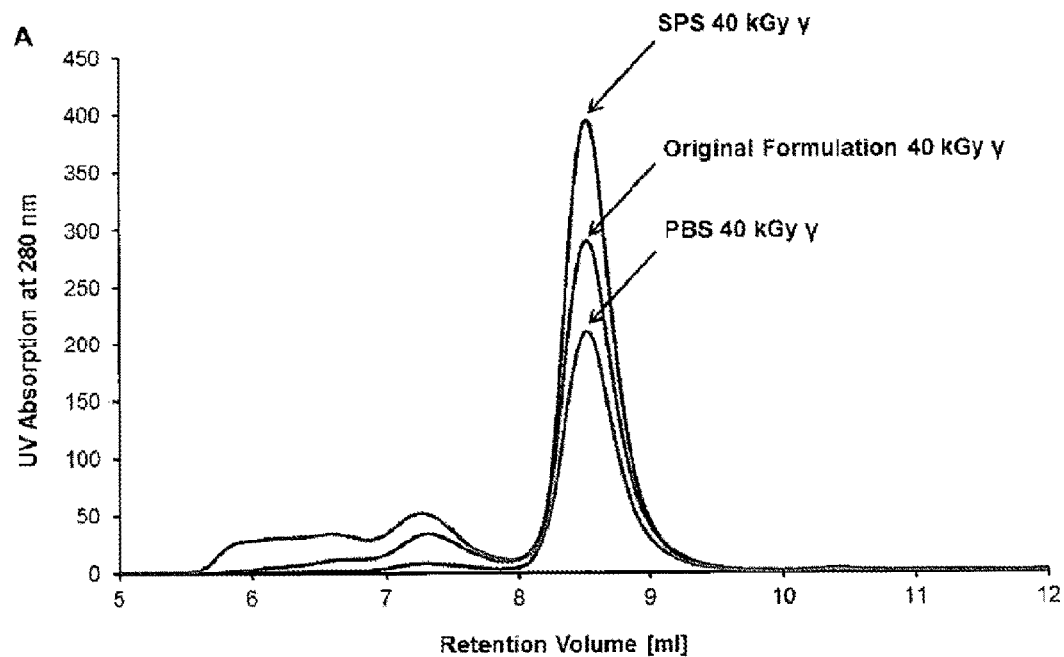
Figure 20B:
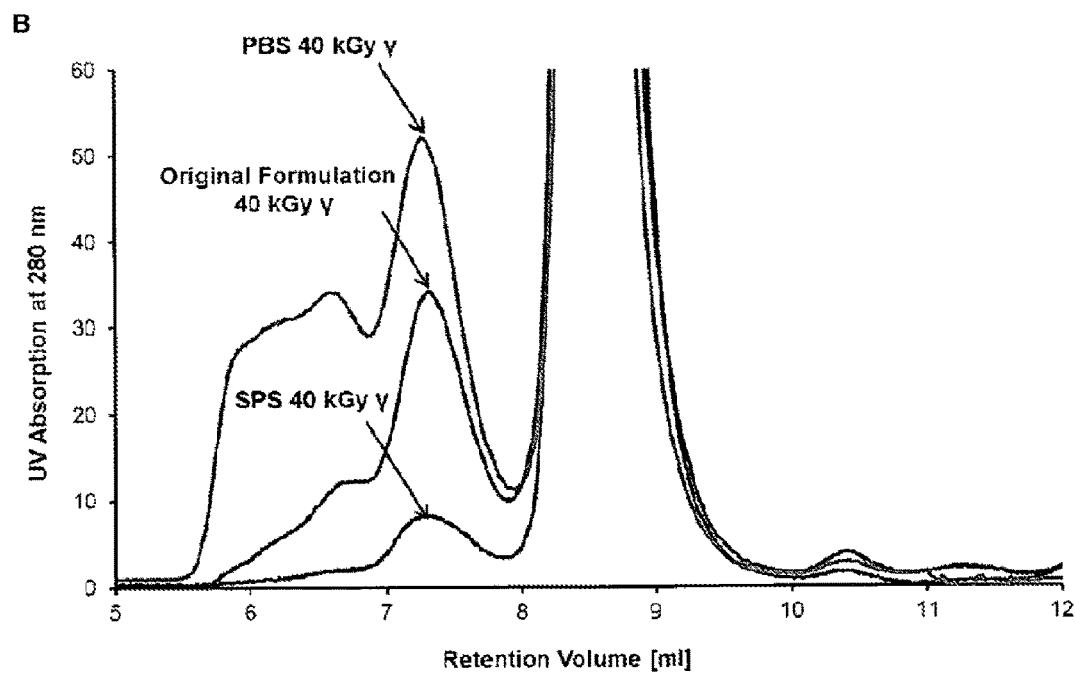

FIG. 20A-B: Size Exclusion Chromatography (SEC) of a therapeutic anti-ErbB2 antibody after lyophilization and subsequent irradiation. The semi-quantitative observations depicted in FIGS. 19 and 20 were confirmed by quantification of the aggregation using SEC analysis of the reconstituted non-irradiated and irradiated samples, respectively. Comparison with molecular weight standards led to the following assignments of the elution peaks: High Molecular weight aggregates (tetramers, trimers, dimers) eluted between 5.5 to 8 mL; the main peaks at an elution volume of 8.5 mL were dedicated to the intact IgG monomer with a molecular weight of approx. 160 kDa and traces of degradation are detected at elution volumes between 10-11 mL. A and B: Comparison of the chromatograms of a therapeutic anti-ErbB2 antibody formulated in SPS, in original formulation and in PBS after lyophilization, γ-irradiation at 40 kGy. The intensities of the main peaks corresponding to the intact IgG are decreasing to the same extent as the intensities of the aggregation peaks are increasing in the samples without SPS formulation. This increase in aggregation is emphasized in the enlarged version of this comparison in FIG. 20B.

Figure 21:
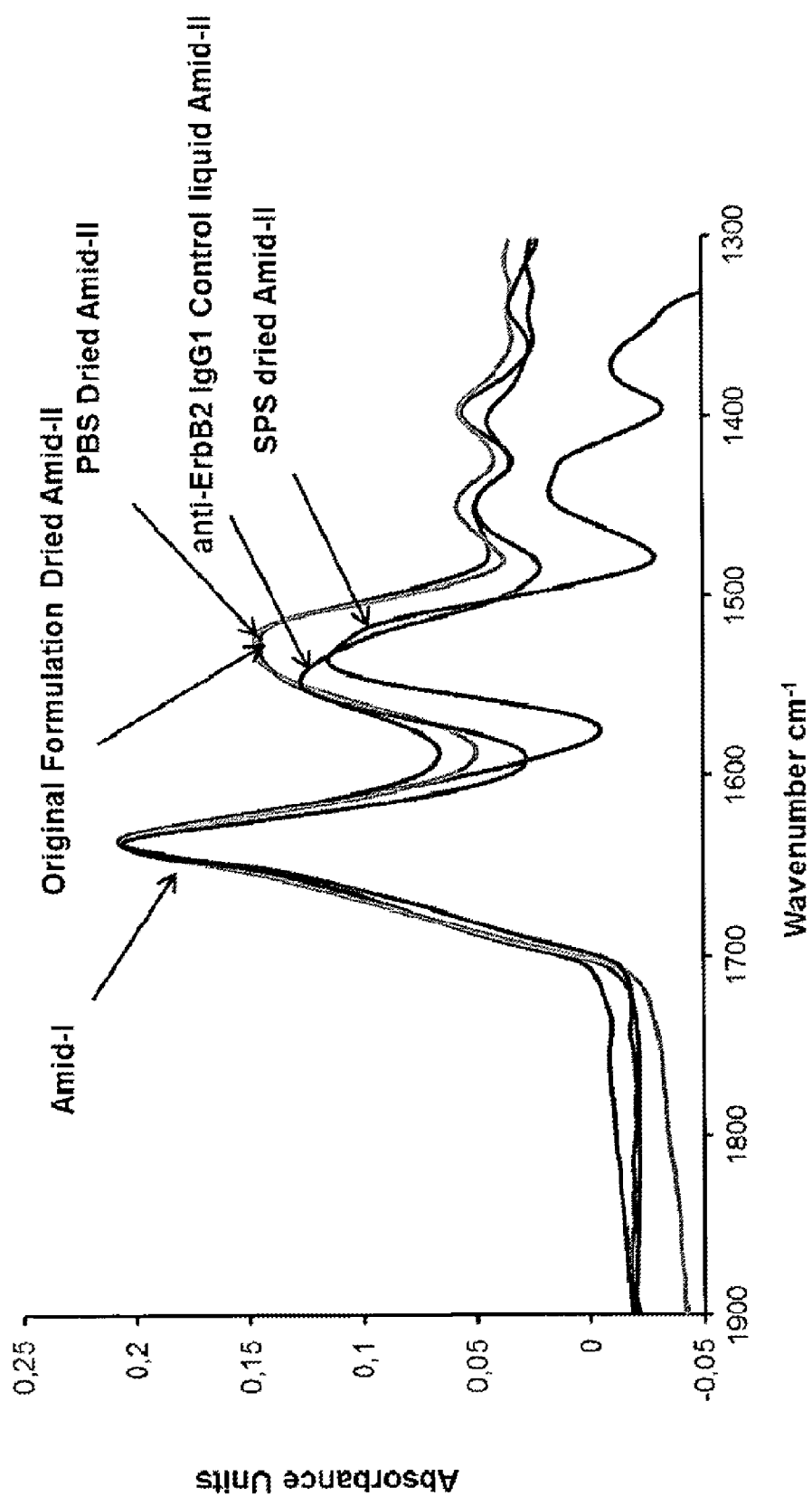

FIG. 21: Secondary structure analysis of a therapeutic anti-ErbB2 antibody by Fourier-Transform Infrared Spectroscopy after lyophilization. Normalized FT-IR absorption spectra of the dried samples in comparison to the freshly reconstituted antibody control.

Figure 22:
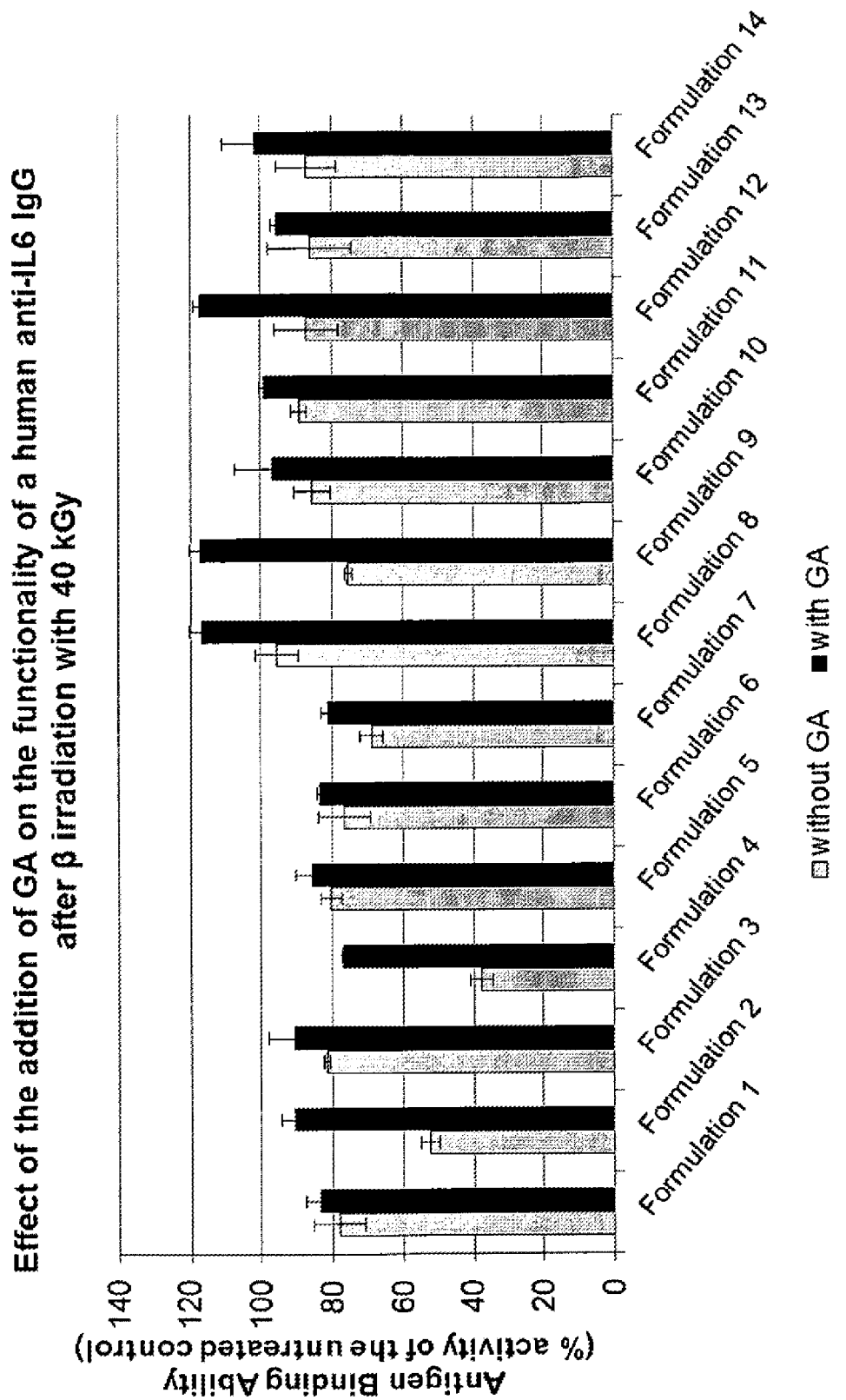

FIG. 22: Stabilization of a human anti-IL6-IgG antibody adsorbed on a 96 well ELISA plate by a variety of different compositions of the protecting solutions against 40 kGy β irradiation monitored by the antigen binding activity in the corresponding anti-IL6-ELISA model in percent of the untreated control. Compositions with seven amino acids (amino acid mixture 1: Ala, Arg, Gly, Glu, Lys, His, Trp) or with five amino acids (amino acid mixture 2: Ala, Arg, Gly, Glu, Lys and amino acid mixture 3: Ala, Gly, Glu, His, Trp, respectively) were used. Supplementation of glycyrrhizic acid to the amino acid mixtures, particularly in combination with the dipeptide carnosin, and other dipeptides resulted in a rescue of the irradiation mediated loss of function to varying degrees.

Figure 23:
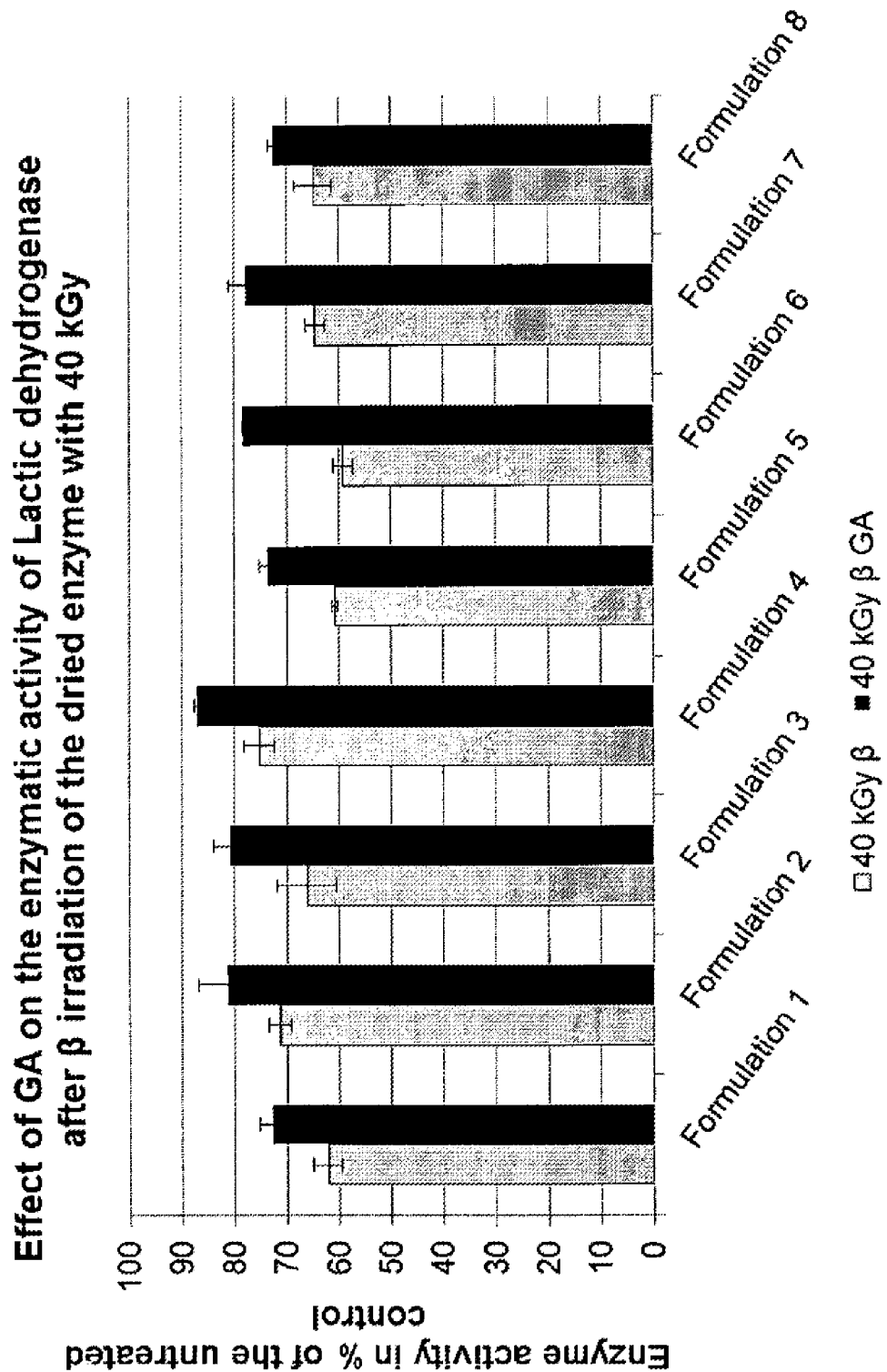

FIG. 23: Retention of enzymatic activity of recombinant lactic dehydrogenase dried in combination with different compositions of the protecting solution according to the present invention against β irradiation with 40 kGy. Enzymatic activity was measured photometrically by monitoring the decrease of the absorption of the enzyme's reduced cofactor NADH at 340 nm upon its oxidation to NADH$^+$ and the simultaneously reduction of the substrate pyruvate to lactate. The enzymatic activity is depicted in percent of the untreated control. Compositions with seven amino acids (amino acid mixture 1: Ala, Arg, Gly, Glu, Lys, His, Trp) or with five amino acids (amino acid mixture 2: Ala, Arg, Gly, Glu, Lys) were used. Supplementation of glycyrrhizic acid to the amino acid mixtures, particularly in combination with the dipeptide carnosin, and other dipeptides resulted in a rescue of the irradiation mediated loss of function to varying degrees.

Figure 24:
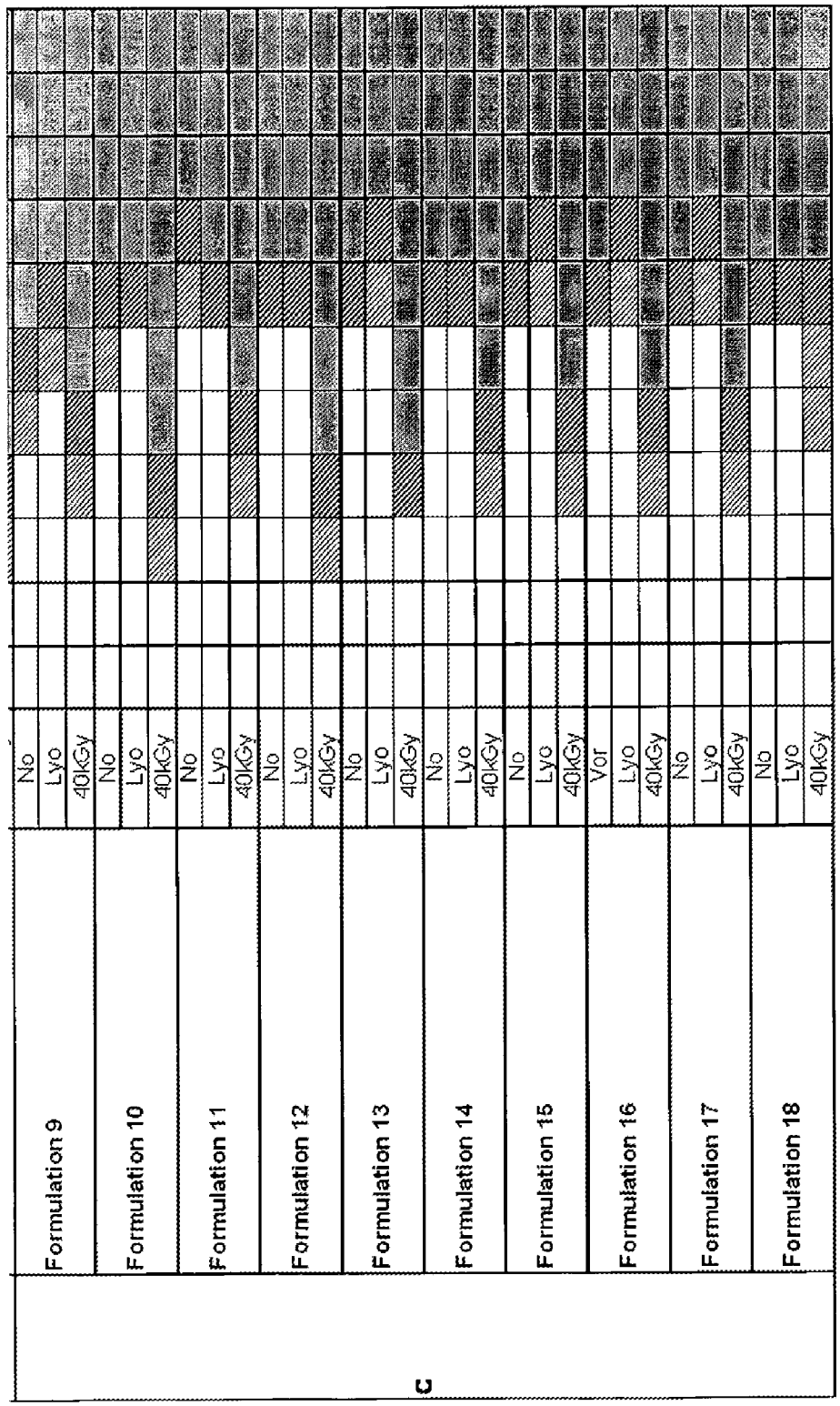

FIG. 24: Activity of an inactivated influenza A H1N1 split vaccine, respective hemagglutination activity, formulated with different compositions of the protecting solution against different types of stresses like freeze drying and β irradiation with 40 kGy. Influenza A H1N1 split vaccine was rebuffered in compositions according to the present invention, containing seven amino acids (amino acid mixture 1: Ala, Arg, Gly, Glu, Lys, His, Trp) or five amino acids (amino acid mixture 2: Ala, Arg, Gly, Glu, Lys and amino acid mixture 3: Ala, Gly, Glu, His, Trp, respectively), supplemented with the dipeptide carnosin, other dipeptides and glycyrrhizic acid, respectively.

DETAILED DESCRIPTION

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Proteins are large macromolecules made up of a sequence of amino acids and characterized by a unique 3D structure corresponding to their biologically active state. The native structure of a protein molecule is the result of a fine balance among various interactions including covalent linkages, hydrophobic interactions, electrostatic interactions (charge repulsion and ion pairing=salt bridge), hydrogen bonding and van der Waals forces. Among these forces, hydrophobic interactions seem to be the dominant forces. Intra-protein and protein-solvent interactions both play an important role in maintaining the protein structure and its stability. Proteins are generally not very stable, as the stabilization energy of the native state is mostly between 5 and 20 kcal/mol, which is equivalent to that of a few hydrogen bonds. Since the folded state is only marginally more stable than the unfolded state, any change in the protein environment may trigger protein degradation or inactivation.

Protein stability is a result of balancing between destabilizing and stabilizing forces. The destabilizing forces are mainly due to the large increase in entropy of unfolding, and the stabilizing forces are provided by a few non-covalent interactions. Disruption of any of these interactions will shift the balance and destabilize a protein and many factors are known that disrupt this delicate balance and affect protein stability. These include for example temperature, pH, ionic strength, metal ions, surface adsorption, shearing, shaking, additives, solvents, protein concentration, purity, morphism, pressure, and freeze/thawing-drying. Chemical transformations that can lead to protein instability include e.g. deamidation, oxidation, hydrolysis, isomerization, succinimidation, disulfide bond formation or breakage, non-disulfide crosslinking, and deglycosylation. One of the most challenging tasks in the development of protein pharmaceuticals therefore is to deal with their physical and chemical instabilities and to provide a formulation able to stabilize the protein in order to achieve an acceptable shelf life.

A common phenomenon of protein instability is formation of protein aggregates that can be soluble or insoluble, chemical or physical, reversible or irreversible. Under certain conditions (or sometimes with time/shelf life), the secondary, tertiary, and quaternary structure of a protein may change and lead to protein unfolding and/or the subsequent formation of protein aggregates. Aggregation of proteins is rapidly emerging as a key issue underlying multiple deleterious effects for protein-based therapeutics, including loss of efficacy, bioavailability, stability and mobilization of an unwanted host immune response toward the protein therapeutic. In particular, antibodies against therapeutic proteins can develop during treatment with a therapeutic protein, which might neutralize or otherwise compromise the clinical effects of these therapeutic proteins and can also be associated with serious side effects such as e.g. cross-reactivity with autologous proteins. The presence of any aggregates in a protein pharmaceutical is therefore generally not acceptable for product release. Protein aggregation may be induced by a variety of physical factors, however, protein aggregation and the rate and mechanism of protein aggregation is generally protein dependent.

The most important factor affecting protein stability is temperature. In general, the higher the temperature, the lower the protein stability. Proteins are usually stable in a certain temperature range. High temperatures cause denaturation of many protein pharmaceuticals. Although protein denaturation at high temperatures can be reversible depending on experimental conditions, high temperatures also accelerate chemical degradation, such as increased hydrolysis of aspartate residues, deamidation of asparagine or glutamine residues. Most importantly, degradation mechanisms in proteins often change depending on the temperature, which is of particular relevance for example during spray-drying or storage and transport, where the cooling-chain may become interrupted.

Furthermore, proteins are often only stable in a narrow pH range and the rate of protein aggregation can be strongly affected by pH. Formulation pH, like temperature, may affect both physical and chemical stability of proteins. Different chemical degradations may be facilitated at different pHs. This explains why degradation products are different at different pHs for the same protein. Hydrolysis can easily occur at aspartate residues under mild acidic conditions. Deamidation of asparagine and glutamine residues readily takes place under strongly acidic, neutral, and basic conditions. Under basic conditions, many reactions can occur, such as peptide bond hydrolysis, deamidation, hydrolysis of arginine to ornithine, 3-elimination and racemization, and double bond formation. The pH effect on chemical stability can further be altered in the presence of excipient.

Proteins can also be adsorbed to many surfaces and interfaces, such as container surfaces, ice/water interfaces and air/water interfaces. Protein adsorption in air/water interfaces starts with the creation of an area for anchoring the protein molecule, followed by subsequent reorientation and rearrangement of the adsorbed molecules at the interface. The severity of adsorption is protein-dependent and does not seem to depend on size and pI of proteins. The secondary structure of a protein, such as IgG, may change significantly at such an adsorption surface. Therefore, surface adsorption may result in loss and/or destabilization of a protein.

Protein surface adsorption is usually concentration-dependent and may reach a maximum—at least for certain proteins—above certain protein concentrations. The type (i.e. material) of a container or membrane employed for e.g. sterile filtration, dialysis or concentration of the protein has a significant influence on protein adsorption to the surface. Protein surface adsorption is further of particular relevance for example during the drying processes like freeze-drying or spray-drying.

The handling of proteins also affects stability. For example, proteins can be denatured due to shaking or shearing. Shaking, such as employed during reconstitution of dried samples, can create a hydrophobic air/water or air/surface interface, which results in alignment of protein molecules at the interface, leading to unfolding of the protein to maximize exposure of hydrophobic residues to the air or surface and the initiation of aggregation. The hydrophobic surfaces that cause protein aggregation during shaking can be either gaseous or solid. Similarly, shearing, such as encountered during spray-drying or spray-freeze drying, also exposes hydrophobic areas of proteins, thereby initiating aggregation. Different proteins may tolerate shearing inactivation to differing degrees. Rigidity of the protein structure and the number of hydrophobic residues on the protein surface might contribute to such different levels of shear tolerance.

Also salts can have an effect on protein stability, although their effect is complex, partly because of the complex ionic interactions on fully exposed surfaces and in fully or partially buried interior of proteins. Salts may stabilize, destabilize, or have no effect on protein stability depending on the type and concentration of salt, nature of ionic interactions and the presence and amount of charged residues in proteins. The salt effect further strongly depends on the pH of the solution, which dictates charged state of ionizable groups.

Depending on the type and concentration, also metal ions may stabilize or destabilize a protein. Since the negative counter ions may also significantly affect protein stability either positively or negatively, contribution of metal ions to protein stability should be carefully interpreted. The number of stabilizing metal ions required for each individual protein molecule is protein-dependent, and the metal ions may or may not be mutually replaceable for protein stability. Metal ions may significantly affect protein stability without affecting much of its secondary structure. Trace amounts of metal ions in protein formulations may catalyze oxidation in proteins namely via the Fenton pathway, targeting in particular the residues methionine, cysteine, histidine, tryptophan, tyrosine, proline, arginine, lysine, or threonine. The catalysis depends on the concentration of the metal ions, and the metal-catalyzed reaction can be facilitated in the presence of a reducing agent such as ascorbat or RSH. Metal ions, oxygen, and reducing agents can generate reactive oxygen species capable of oxidizing proteins.

In close relation to metal ions are chelating agents, such as EDTA and citric acid, that may either destabilize a protein by binding to the protein and/or its critical metal ions or stabilize the protein by binding to any harmful metal ions. Since transition metal ions can catalyze protein oxidation, ion chelating agents should be able to protect a protein from metal catalyzed oxidation. In many cases, however, the effect of chelating agents is more complex. The net effect depends on the metal ions, oxidation mechanism, and the type of the chelating agent.

Furthermore, protein aggregation is generally concentration dependent. The effect of the concentration of a protein on its aggregation depends on the mechanism of aggregation and the experimental conditions. In some cases, protein concentration also affects chemical degradation to a certain degree. On the other hand, concentrated protein solutions can be more resistant against freezing-induced protein aggregation and loss of activity.

Purity of the protein preparation is another important aspect, as the presence of trace amounts of enzymes, metal ions, or other contaminants can potentially affect protein stability.

High pressure can furthermore cause protein unfolding, because the volume of protein-solvent systems is smaller in the unfolded state. In other words, unfolded proteins are more compressible than folded proteins, which may play a role during freeze-drying or spray-freeze drying.

Also many chemical reactions are responsible for inactivation of protein drugs. In many cases, several reactions can happen simultaneously in proteins, making separation and identification of protein degradation products very difficult. To prevent proteins from chemical inactivation, the dominant reaction should first be identified and inhibited. This can be achieved to a certain degree by adjusting the formulation pH away from favorable ranges. The location of labile amino acids in a protein is critical in determining their chemical reactivity. Chemical reactions of many amino acids in proteins require a certain local flexibility and thus the rate of a reaction may be higher in denatured proteins or small peptides with high flexibility than the native proteins. Native protein conformation therefore needs to be protected to prevent or inhibit potential chemical degradation.

Deamidation, which in many cases is the major degradation pathway in proteins, also appears to be the most common degradation pathway in protein pharmaceuticals. The two amino acids susceptible to deamidation in proteins are asparagine and glutamine, whereas asparagine is the more labile amino acid. Deamidation of asparagine in proteins and peptides in an aqueous solution can proceed at much higher rate than hydrolysis of a peptide bond. The rate, mechanism, and location of deamidation in proteins are pH dependent. Furthermore, the relative positions of asparagine and/or glutamine in proteins affects their relative rate of deamidation, as do neighboring amino acids at deamidation sites in proteins. The most labile sequence seems to be Asn-Gly and the rate of deamidation in proteins is further influenced by secondary structure of proteins.

Another chemical reaction that can result in the inactivation of proteins is oxidation. In particular, the side chains of histidine, cysteine, tryptophan and tyrosine residues are potential sites of oxidation. Oxidation at these sites can be catalyzed by trace amount of transition metal ions (site-specific process) or enhanced by oxidants or upon exposure to light (non-site specific process). The site specificity is due to generation of and oxidation by reactive oxygen species at specific metal-binding sights. The most easily oxidizable sites are the thio groups on methionine and cysteine. Methionine residues in proteins can be easily oxidized by atmospheric oxygen. The formulation pH may affect the rate of oxidation by changing the oxidation potential of oxidants, the affinity of binding between catalytic metal ions and the ionizable amino acids, and the stability of oxidation intermediates. Moreover, exposure of proteins to ionizing radiation like gamma- or electron beam radiation may result in oxidation of amino acid side chains in the protein by the generated reactive oxygen species.

Disulfide bonds are often critical in controlling both protein activity and stability. Free cysteine residues in proteins can be oxidized easily to form disulfide bond linkages or cause thio-disulfide exchanges, causing protein aggregation or polymerization. Thio-disulfide exchange in a protein is a reaction between an ionized thiol group (thiolate anion) and a disulfide bond. The rate of thiol-disulfide exchange depends on the extent of ionization of the nucleophilic thiol, and therefore generally increases as the reaction pH increases until pK of the nucleophilic thiol group is exceeded. Even protein does not have free cysteine residues, disulfide bond scrambling may still occur, causing protein aggregation.

Amino acids, the components of proteins, are additionally subject to acid and base hydrolysis. Most peptide bonds are stable except those in —X-Asp-Y— sequence. During hydrolysis, aspartate forms succinimide intermediate, which is similar to the succinimide intermediate obtained during deamidation of Asn. In addition, formation of cyclic anhydride intermediate is also possible, especially when the C-flanking residue of aspartate is proline. In many cases, hydrolysis is a continuation after deamidation of asparagine residues.

Except for glycine, amino acids further have the potential of racemization. Aspartate-X peptide bonds can easily undergo a reversible isomerization between aspartate and iso-aspartate via a cyclic imide (succinimide) intermediate. The succinimide intermediate is usually not stable, and significant hydrolysis may occur within hours. Like deamidation, the rate of aspartate isomerization is strongly influenced by its location and mobility in a protein. The iso-aspartate formation is most likely to occur in relatively unstructured domains of intact proteins or domains susceptible to transient unfolding.

Formation of succinimide intermediates may precede deamidation of asparagine and isomerization of aspartate in proteins. In fact, formation of succinimide is the cause of iso-aspartate derivative formation in proteins. Asparagine deamidates via succinimide formation at neutral and alkaline conditions, but formation at Asp-Gly linkages in proteins may occur at an optimum pH of 4-5. The rate of succinimide formation is strongly influenced by neighboring groups of labile residues and by protein conformation.

Proteins may further form covalent dimers and polymers by non-disulfide pathways. For example, formaldehyde-mediated cross-linking causes significant aggregation of lyophilized tetanus and diphtheria toxoids during storage and thus raises concerns for storing formaldehyde-inactivated virus vaccine formulations in both liquid and solid forms.

Proteins may also be chemically transformed by deglycosylation, which renders the protein more sensitive to thermal denaturation, as one of the functions of carbohydrate moieties in proteins is to protect proteins from thermal and hydrolytic inactivation. The effect of glycosylation on the stability of proteins varies strongly from protein to protein.

Finally, sugars are often used as protein stabilizers in both liquid and solid formulations, however, reducing sugars may react with amino groups in proteins forming carbohydrate adducts, especially at high temperatures. This extremely complex browning pathway is known as Maillard reaction.

All of the above described influences—either simultaneously or separately—can occur when different types of stresses are applied to a protein, such as during isolation and purification of a protein, drying of a protein e.g. by lyophilisation, spray-drying, spray-freeze drying or foam drying, storage of a protein in solution or after drying as well as reconstitution after drying.

In particular during drying of a protein, considerable stress is applied. For example, during freeze-drying, pure crystalline ice forms from the liquid as it becomes frozen. Exposure of proteins to this ice-water interface can lead to denaturation, e.g. freezing damage. Further, removal of the hydration shell from proteins during drying in the absence of the appropriate stabilisers can cause an additional destabilisation of the protein structure. Furthermore, variations in pressure, pH value or ion concentration as well as concentration effects of additives, temperature variations and shear forces also affect the stability of a protein during drying. Also the influence of oxygen, surface effects or hydrolysis may inactivate or denature proteins. During storage of the dried protein, stress factors such as e.g. residual moisture, light exposure, oxidation as well as temperature during storage may further affect denaturation and inactivation of the dried proteins. All of the above aspects may result in problems in reconstitution of the proteins and loss of activity.

As it is more complicated to provide structural modifications of a protein of interest, commonly applied methods of protein stabilization are based on the addition of excipients. Excipients may reduce aggregation and may also retard certain chemical degradations in proteins. Their stabilizing effects are concentration- and protein-dependent, although high concentrations of excipients may not be necessarily more effective, and in some cases, can have negative effects. Frequently used protein stabilizers include sugars and polyols, amino acids, amines, salts, polymers and surfactants, each of which may exert different stabilizing effects.

Excipients are added to formulations for several reasons and some excipients may have more than one effect or purpose for being part of the formulation. In the choice of excipients, both physical and chemical stability have to be optimized. Excipients are often used to slow down or prevent the physical destabilization processes (protein aggregation). There are specific mechanisms of solvent-induced stabilization of proteins, which are specifically related to the excipients in the formulation. Stabilization is achieved by strengthening of the protein-stabilizing forces, by destabilization of the denatured state, or by direct binding of excipients to the protein.

The main function of stabilizers in pharmaceutical formulations thus is to protect the protein against the different types of stresses that are applied to a protein during isolation and purification of a protein, drying of a protein e.g. by lyophilization, spray-drying, spray-freeze drying or foam-drying, storage of a protein in solution or after drying as well as reconstitution after drying.

The structure of water surrounding a folded protein in solution is extremely important in maintaining the native structure of the protein. The presence of stabilizing excipients, such as sugars and amino acids, may stabilize the protein by a preferential exclusion of the excipients from the protein surface (the so-called preferential exclusion model) because of their thermodynamic unfavorable interactions with the peptide backbone, thus leading to the protein becoming preferentially hydrated, as more water molecules are found on the surface of the protein than in the bulk solution. This process is believed to act stabilizing upon exposure of proteins to typical stresses like isolation, purification, storage in solution, and preparation of liquid protein drug formulations. Protein stabilization by preferential exclusion depends on the concentration of the preferentially excluded excipient and requires sufficient amounts of water to be present at least locally.

During drying of proteins, the concentration of the excipient is increased, and the preferential exclusion effect is enhanced in the residual wet regions. Due to this process the protein remains hydrated in its native form until the residual water molecules are removed by further drying (freeze drying etc.). Upon removal of this residual water, hydrogen bonds are increasingly formed between the protein and the functional groups of the excipient, thereby replacing the missing interactions of the protein with the surrounding water molecules that constituted the hydration shell (water replacement, preferential interaction). Thus, excipients having lyoprotectant and/or cryoprotectant effects on the proteins are generally added to optimize protein stability during changes in water content. Examples of such excipients include e.g. sugars and polyols but also other excipients such as for example surfactants and amino acids. Commonly used excipients in the development of lyophilization formulations are discussed, for example, in Kofi Bedu-Addo 2004 (Pharmaceutical Technology, Lyophilization; 2004: 10-30).

The freeze-drying process yields a dried powder containing the protein in a glassy state, often including amorphous excipients and residual water. In the dried state, the rate of chemical degradation and unfolding is influenced by the mobility of the protein and the surrounding excipient molecules. Such mobility is greatly reduced in the glassy state of the dried protein, which can be further stabilized by the presence of amorphous excipients, such as e.g. trehalose. The residual moisture will depend on the solid state properties of the system, that is amorphous vs. crystalline, in combination with the chosen process conditions.

Excipients are also added to optimize a dry powder formulation. A dry powder needs to have certain characteristics to be useful. For example, a freeze-dried cake requires an acceptable appearance (as this is indicative of stability), should be rapidly dissolvable and blow-out of the formulation (i.e. foaming of the product after reconstitution) must be prevented. For this purpose, bulking agents such as sugars and polyols are generally selected, as they can also act as cryoprotectants and lyoprotectants. When selecting an appropriate excipient, the solid state properties are to be considered first. For example, mannitol will usually crystalize and thus lead to a cake with a good structural stability. However, mannitol can crystalize in three different polymorphic forms ($\alpha$, $\beta$, $\delta$) with different stabilities, and mannitol-hemi-hydrate, which may release its crystal water during storage and the solid state of mannitol depends on the freeze-drying conditions applied as well as the presence of other excipients. Sucrose usually remains amorphous on freeze-drying, which is desirable for protein stability, but it also increases the water content after primary drying and increases the danger for deliquescence and collapse of the final product.

Prevention of the direct interaction between proteins can also stabilize proteins, as these interactions most often lead to aggregation. For example arginine has previously been reported to bind strongly to some proteins while it has also been reported to be excluded from the surface of others.

Chemical instability can be minimized by the appropriate choice of preparation procedures, storage conditions, temperature, vials, or by addition of antioxidant such as for instance ascorbic acid. Ascorbic acid acts as an antioxidant to prevent oxidation of proteins. On the other hand, it also facilitates metal-catalyzed oxidation of proteins due to the reducing properties of ascorbate in the presence of metal ions and oxygen. This latter effect is usually avoided by co-adding chelating agents such as EDTA, DTPA, DFO.

Adsorption to interfaces is generally avoided by the addition of excipients that (ideally) are more surface-active than the protein itself. Mainly surfactants or other proteins are used to coat or adsorb competitively to the inner surface of the containers or adsorb to the surfaces created in the preparation of the delivery system. Surfactants may be classified as either ionic or non-ionic. Low concentrations of non-ionic surfactants are often sufficient to prevent or reduce protein surface adsorption or aggregation due to their relatively low critical micelle concentrations (CMC). Examples of generally employed non-ionic surfactants include poloxamer (Pluronic F-68) and polyoxyethyleneglycol dodecyl ether (Brij35), polysorbate 80, 20, Human Serum Albumine etc. Some of these surfactants, particularly the polysorbates, may be contaminated with alkyl peroxides arising from the ether linkage incorporated in their structures, which is disadvantageous as it can accelerate the oxidation of proteins. Polymers and dextran can also be used to protect against surface adsorption, although only large PEGs are reported to have a stabilizing effect on proteins, while small PEGs appear to induce unfolding. The chosen concentration of surfactant depends on the effect that needs to be avoided, but typically it is just above the CMC value, where a monolayer of the surfactant is present at the interface. Examples of generally employed ionic surfactants include Cetyltrimethylammonium chloride (CTAC) and Cetyltrimethylammonium bromid (CTAB).

During the process of preparing formulations, for example during the drying process, changes in the microclimate pH can occur, owing to changes in the proteins microenvironment. In drying process one component will stay in solution for a longer period than others, which can lead to a pH shift of more than three pH units. Smaller pH changes are also encountered during temperature changes such as lyophilization, spray drying, storage, etc. as the pH is dependent on temperature. However, proteins are usually only stable over a narrow pH range. Thus, an important step early in developing the appropriate formulation is to study the pH stability, especially in the range between pH 3-10.

Maintenance of the pH is achieved by employing the appropriate buffer system. Unfortunately, however, there are no general rules for specific buffer selection. Usually, specific excipients for avoiding pH changes are not added, but instead very low concentrations of buffer should be used, if it is possible. When choosing a buffer, it has to be kept in mind that the buffer system may affect the chemical stability of the formulation, as the pH value appears to be the major controlling variable in deamidation reactions and that aggregation rates are influenced by the choice of buffer.

Salts are used frequently for the adjustment of pH and tonicity. During freezing the pure solvent (water) freezes first, leading to an increase of the salt concentration in the remaining liquid phase (freeze concentrated phase), thereby increasing the ionic strength.

Finally, in some cases, an isotonic formulation might be required either due to the stability requirements of the bulk solution or the requirements for the route of administration. Excipients such as mannitol, sucrose, glycine, glycerol, and sodium chloride are good tonicity adjusters. Tonicity modifiers also can be included in the diluent rather than the formulation.

Accordingly, the present invention relates to a method for preventing the unfolding of a (poly)peptide and/or inducing the (re-)folding of a (poly)peptide, comprising the step of embedding the (poly)peptide in an aqueous solution, wherein the solution comprises (i) at least three different amino acids; or (ii) at least one dipeptide or tripeptide; and wherein the solution is free or substantially free of (a) sugar; and (b-i) protein; and/or (b-ii) denaturing compounds; and (c) silanes.

In an alternative or preferred embodiment, the present invention relates to a method for preventing the unfolding of a (poly)peptide during drying and/or inducing the (re-)folding of a (poly)peptide after drying, comprising the step of embedding the (poly)peptide in an aqueous solution, wherein the solution comprises (i) at least three different amino acids; or (ii) at least one dipeptide or tripeptide; and wherein the solution is free of (a) sugar; and (b-i) protein; and/or (b-ii) denaturing compounds.

The term "(poly)peptide" in accordance with the present invention describes a group of molecules which comprises the group of peptides, consisting of up to 30 amino acids, as well as the group of polypeptides, consisting of more than 30 amino acids. Also encompassed by the term "(poly)peptide" are proteins as well as fragments of proteins. (Poly)peptides may form dimers, trimers and higher oligomers, i.e. consisting of more than one (poly)peptide molecule. (Poly) peptide molecules forming such dimers, trimers etc. may be identical or non-identical. The corresponding higher order structures are, consequently, termed homo- or heterodimers, homo- or heterotrimers etc. Homo- or heterodimers etc. also fall under the definition of the term "(poly)peptide". The terms "polypeptide" and "protein" are used interchangeably herein. The term "(poly)peptide" also refers to naturally modified (poly)peptides wherein the modification is effected e.g. by post-translational modifications such as e.g. glycosylation, acetylation, phosphorylation and the like. Such modifications are well known in the art.

The term "unfolding of a (poly)peptide", as used herein, relates to the loss of the characteristic three-dimensional structure of (poly)peptide. The term "unfolding of a (poly) peptide", as used herein, includes partial as well as complete unfolding of (poly)peptide. The structure of an unfolded (poly)peptide is also referred to as random coil. (Poly) peptide are present in an unfolded state (or random coil) for example immediately after translation from a sequence of mRNA to a linear chain of amino acids, but also due to e.g. chemical unfolding, thermal denaturation, unfolding due to pressure or oxidative damage. The three-dimensional structure of a (poly)peptide, which is also referred to as the native state, is the result of interactions between amino acids and is, thus, determined by the amino acid sequence of the (poly)peptide. Generally, unfolding or at least partial unfolding of a (poly)peptide results in a loss of the biological activity of said (poly)peptide as the three-dimensional structure is essential for function.

The term "(re-)folding of a (poly)peptide", as used herein, refers to the folding or refolding of a (poly)peptide that has previously been unfolded, e.g. by denaturation or chemical unfolding, in order to return the (poly)peptide into its native three-dimensional structure.

As used herein, the term "drying" refers to the reduction or removal of the liquid content of a sample. Preferably, the remaining liquid content is less than 20%, such as for example less than 10%, such as for example less than 5%, more preferably less than 3%, such as less than 2% or less than 1%. Most preferably, the liquid is less than 0.5% or less.

The term "embedding", as used herein, relates to the complete insertion of the (poly)peptide into the solution in accordance with the invention.

In accordance with the present invention, the protein is embedded into the solution prior to and during drying, thereby preventing unfolding of the protein during the drying step. Alternatively, or additionally, the protein may be embedded into the solution upon reconstitution of the dried protein, thereby ensuring the correct refolding of the reconstituted protein. It will be appreciated by the skilled person that when a protein was dried in a solution according to the present invention, the reconstitution may be carried out in a solution different from the solution defined in accordance with the method of the invention and vice versa. Preferably, both the drying and the reconstitution of the protein is carried out in a solution according to the method of the invention, wherein the solution employed in these steps may be identical or may comprise different compounds.

The term "aqueous solution", as used herein, is well known to the person skilled in the art and relates to a solution in which the solvent is water.

The term "amino acid", in accordance with the present invention, relates to organic molecules that have a carboxylic acid group, an amino group and a side-chain that varies between different amino acids. Amino acids are the essential building blocks of proteins. In accordance with the present invention, the term "amino acid" refers to free amino acids which are not bound to each other to form oligo- or polymers such as dipeptides, tripeptides, oligopeptides or (poly)peptide.

The amino acids comprised in the solution of the present invention can be selected from naturally occurring amino acids as well as artificial amino acids or derivatives of these naturally occurring or artificial amino acids.

Naturally occurring amino acids are e. g. the 20 proteinogenic amino acids glycine, proline, arginine, alanine, asparagine, aspartic acid, glutamic acid, glutamine, cysteine, phenylanine, lysine, leucine, isoleucine, histidine, methionine, serine, valine, tyrosine, threonine and tryptophan. Other naturally occurring amino acids are e. g. carnitine, creatine, creatinine, guanidinoacetic acid, ornithine, hydroxyproline, homocysteine, citrulline, hydroxylysine or beta-alanine.

Artificial amino acids are amino acids that have a different side chain length and/or side chain structure and/or have the amino group at a site different from the alpha-C-atom. Derivates of amino acids are modified amino acids, including, without being limiting, n-acetyl-tryptophan, phosphonoserine, phosphonothreonine, phosphonotyrosine, melanin, argininosuccinic acid and salts thereof and DOPA.

In connection with the present invention, all the terms also include the salts of the respective amino acids.

In accordance with the present invention, three or more amino acids, which differ from each other, are comprised in the solution. For example, the term "at least three different amino acids" also relates to at least four different amino acids, such as at least five, at least six, at least seven, at least eight, at least nine, at least ten different amino acids or more, such as at least eleven, at least 12, at least 13, at least 14, at least 15, at least 16, at least 17 or at least 18 different amino acids. The term further encompasses exactly three, exactly four, exactly five, exactly six, exactly seven, exactly eight, exactly nine, exactly ten, exactly eleven, exactly 12, exactly 13, exactly 14, exactly 15, exactly 16, exactly 17 or exactly 18 different amino acids. It will be readily understood by a person skilled in the art that when referring to an amino acid herein, more than one molecule of said amino acid are intended. Thus, the recited amount of different amino acids is intended to limit the amount of different types of amino acids, but not the number of molecules of one type of amino acid. Thus, for example the term "three different amino acids", refers to three different types of amino acids, wherein the amount of each individual amino acid is not particularly limited. Preferably, the number of different amino acids does not exceed 18.

The term "dipeptide or tripeptide", as used herein, relates to peptides consisting of two or three amino acids, respectively. Exemplary dipeptides are glycylglutamine (Gly-Gln, giving rise to an enhanced stability as compared to glutamine alone), glycyltyrosine (Gly-Tyr, giving rise to an increased solubility in water as compared to tyrosine alone), alanylglutamine (Ala-Gln, giving rise to an increased solubility in water as compared to glutamine alone) and glycylglycine.

Further non-limiting examples of naturally occurring dipeptides are carnosine (beta-alanyl-L-histidine), N-acetylcarnosine (N-acetyl-(beta-alanyl-L-histidine), anserine (beta-alanyl-N-methyl histidine), homoanserine (N-(4-aminobutyryl)-L-histidine), kyotorphin (L-tyrosyl-L-arginine), balenine (or ophidine) (beta-alanyl-N tau-methyl histidine), glorin (N-propionyl-γ-L-glutamyl-L-ornithine-δ-lac ethyl ester) and barettin (cyclo-[(6-bromo-8-en-tryptophan)-arginine]).

Examples of artificial dipeptides include, without being limiting, aspartame (N-L-γ-aspartyl-L-phenylalanine 1-methyl ester) and pseudoproline.

Exemplary tripeptides are glutathione (γ-glutamyl-cysteinyl-glycine) and its analogues ophthalmic acid (L-γ-glutamyl-L-α-aminobutyryl-glycine) as well as norophthalmic acid (γ-glutamyl-alanyl-glycine). Further non-limiting examples of tripeptides include isoleucine-proline-proline (IPP), glypromate (Gly-Pro-Glu), thyrotropin-releasing hormone (TRH, thyroliberin or protirelin) (L-pyroglutamyl-L-histidinyl-L-prolinamide), melanostatin (prolyl-leucyl-glycinamide), leupeptin (N-acetyl-L-leucyl-L-leucyl-L-argininal) and eisenin (pGlu-Gln-Ala-OH). It is preferred that the at least one di- or tripeptide and more preferred all di- or tripeptides, when used in connection with medical applications, do not exert any pharmacological properties.

Preferably, at least one dipeptide is selected from the group consisting of carnosin, glycyltryrosine, glycylglycine and glycylglutamine.

In accordance with the present invention, the solution comprises one or more di- or tripeptides. For example, the term "at least one dipeptide or tripeptide" also relates to at least two di- or tripeptides, such as at least three, at least four, at least five, at least six, at least seven, at least eight or at least nine di- or tripeptides. The term further encompasses exactly one, exactly two, exactly three, exactly four, exactly five, exactly six, exactly seven, exactly eight or exactly nine di- or tripeptides. Where more than one di- or tripeptide is comprised in the solution, the mixture of dipeptides and tripeptides is explicitly envisaged herein. The number of di- and tripeptides can be selected independently of each other, e.g. the solution may comprise two dipeptides and three tripeptides. It will be readily understood by the skilled person that when referring to a certain number of di- and tripeptides herein, said number is intended to limit the amount of different types of di- and tripeptides, but not the number of molecules of one type of dipeptide or tripeptide. Thus, for example the term "four dipeptides or tripeptides", refers to four different types of dipeptides and/or tripeptides, wherein the amount of each individual di- and/or tripeptide is not particularly limited. Preferably, the number of (different) di- or tripeptides does not exceed nine.

Preferred amounts of amino acids, dipeptides and/or tripeptides to be employed are between 0.1 and 150 mg/ml, preferably between 1 and 100 mg/ml, more preferably between 10 and 50 mg/ml, even more preferably between 20 and 35 mg/ml and most preferably the amount is 25 mg/ml.

The term "free or substantially free of (a) sugar", in accordance with the present invention, refers to a solution devoid of or substantially devoid of any types of sugars, i.e. the monosaccharide, disaccharide or oligosaccharide forms of carbohydrates as well as sugar alcohols. Examples of sugars commonly used in methods of protein folding, but absent in accordance with the present invention, include without being limiting saccharose, trehalose, sucrose, glucose, lactose, sorbitol or mannitol. The solution is considered to be substantially free of sugar if it contains less than 0.1% (w/v) sugar, more preferably less than 0.01% (w/v) and even more preferably less than 0.001% (w/v) and most preferably less than 0.0001% (w/v).

As described herein above, sugars are often used in the art to stabilize the protein against freeze stress (cryoprotectant) and against drying stress (lyoprotectant), respectively. Furthermore, sugars are added to a formulation as tonicity adjuster and as bulking agents.

As used herein, the term "free or substantially free of protein" refers to a solution that does not comprise or does substantially not comprise any protein(s) other than the (poly)peptide to be (re-)folded or prevented from unfolding. It will be appreciated by the skilled person that trace amounts of proteins associated with e.g. contamination of the solution may be present and are not excluded by the requirement that the solution is free of protein. Thus, the solution is considered to be substantially free of protein if it contains less than 0.1% (w/v) proteins other than the (poly)peptide to be (re-)folded or prevented from unfolding, more preferably less than 0.01% (w/v) and even more preferably less than 0.001% (w/v) and most preferably less than 0.0001% (w/v).

Additional proteins, such as e.g. HSA, BSA etc., are often added to protein- or peptide solutions in order to avoid the adsorption to interfaces, unnecessary agitation and to minimize unnecessary air- or foam formation in the vials. Surfactants like other proteins are added to the formulations to coat or adsorb competitively to the inner surface of the containers, or to adsorb to the surface created in the preparation of the delivery system.

In accordance with the present invention, the solution can further be "free or substantially free of denaturing compounds", i.e. the solution does not comprise or does not substantially comprise any denaturing agents generally employed in methods of (re-)folding proteins expressed as insoluble protein aggregates (inclusion bodies). Examples of such denaturing compounds include, without being limiting, chaotropic solvent additives like urea, guanidinium chloride or sodium dodecylsulfate (SDS). The solution is considered to be substantially free of denaturing compounds if it contains less than 0.01% (w/v) denaturing compounds, more preferably less than 0.001% (w/v) and most preferably less than 0.0001% (w/v).

The term "free or substantially free of silanes", as used herein, refers to a solution that does not or does not substantially comprise any silane such as for example alkoxysilanes, organofunctional silanes, hydrogensil(ox)anes, siloxanes and organosilanes comprising silyl compounds with other functional groups. The solution is considered to be substantially free of silanes if it contains less than 0.01% (w/v) silanes, more preferably less than 0.001% (w/v) and most preferably less than 0.0001% (w/v).

The term "comprising" in the context of the solution according to the method of the invention denotes that further components can be present in the solution, with the exception of the explicitly recited compounds. Non-limiting examples of such further components include saponines or fatty acids or derivative thereof, as described herein below. Preferably, the solution consists of the recited amino acids or di- or tripeptides and a saponine or a fatty acids or a derivative thereof, but no further compounds. More preferably, the solution according to the method of the invention solely consists of the recited amino acids or di- or tripeptides.

As discussed above, there is currently no single established rule to follow in the selection of (a) suitable stabilizer(s), partly due to the lack of a clear and definitive understanding of protein-co-solute interactions and due to multiple inactivation mechanisms, as outlined above, but also due to the large size of proteins, their compositional variety and amphipatic characteristics that influence specific behavior such as folding, conformational stability, and unfolding/denaturation. Furthermore, the stabilizing effect of the traditionally employed combination of excipients is strongly dependent on the specific protein and, thus, may increase protein stability only in a limited amount. Due to these structural differences among different proteins, a generalization of universal stabilization strategies has not been successful so far.

In accordance with the present invention, it was surprisingly found that a solution as defined in accordance with the method of the invention prevents the unfolding of a native (poly)peptide during drying thereof and/or promotes the correct (re-) folding of a (poly)peptide upon reconstitution. In other words, the three-dimensional structure of the (poly) peptide is maintained when it is dried in the solution in accordance with the invention. The retention of the three-dimensional structural characteristics of the protein is an indispensable pre-requisite of its functionality and efficacy. As discussed herein above, certain conditions or stresses may change the secondary, tertiary, and quaternary structure of a protein and subsequently lead to protein unfolding and/or aggregation, a major event of physical instability. Changes in the three-dimensional structure of proteins affect potential chemical degradation, deamidation, alterations of disulfide bonds or succinimide formation. Furthermore, the secondary structure of a protein, such as IgG, may change significantly at an adsorption surface and the rigidity of the protein structure and the number of hydrophobic residues on the protein surface may affect shear tolerance. Despite the differences in the nature of the degradation pathways discussed herein, they are all dependent on or influenced by the three-dimensional structure of the respective proteins. Thus, by providing the present method to maintain the native three-dimensional structure of proteins, degradation induced by the majority of these various influences can be prevented. The method of the present invention therefore provides a significant advantage over prior art methods, which require that the basic properties of a protein are examined for the development of a protein pharmaceuticals.

The findings of the present invention are particularly surprising as amino acids have been used in stabilization solutions together with other excipients for a long period of time. However, due to the complexity of protein structures and characteristics, the large number of physical and chemical factors influencing protein stability and the vast amount of stresses that might lead to degradation of a protein it was never envisaged that the presence of at least three different amino acids or at least one di- or tripeptide in a solution could be sufficient to prevent the unfolding of proteins in a solution, and in particular during drying.

As is shown in the appended examples, the three-dimensional structure of a protein is maintained even after irradiation. Furthermore, no crystal-formation is observed during freezing and thawing, thus reducing negative effects usually associated with freeze-drying methods.

Due to the stabilizing effect of the solution in accordance with the present invention, changes in the three-dimensional structure of proteins are avoided and the risk of generating an unwanted host immune response towards such proteins is reduced.

Furthermore, the inventive solution does not contain any of the additives recited above that are generally employed in the art and, thus, offers the additional advantage that the costs associated with preparing the solution are reduced and no further purification steps are required in order to remove additives that might be detrimental when using the (poly) peptides for example in therapeutic applications. The dried proteins are resistant to temperature stresses, thus rendering them particularly stable during storage e.g. under conditions lacking a continues cold-chain.

In a particularly preferred embodiment of the present invention, the solution is free of cetyltrimethylammonium chloride (CTAC), N-Lauroylsarcosin, Tween, Brij 35 and/or polysorbate. The compounds cetyltrimethylammonium chloride (CTAC), N-Lauroylsarcosin, Tween, Brij 35 and polysorbate are examples of commonly employed ionic or non-ionic detergents. In a more preferred embodiment of the present invention, the solution is free of any ionic and/or non-ionic detergents.

In another preferred embodiment, the at least three amino acids do not include: (i-a) a combination of glutamate and glutamine and/or (i-b) a combination of aspartate and asparagine.

In an alternative preferred embodiment, the at least three amino acids do not include phenylalanine.

In a further preferred embodiment of the method of the invention, the at least three amino acids are selected from the groups of (a) amino acids with non polar, aliphatic R groups; (b) amino acids with polar, uncharged R groups; (c) amino acids with positively charged R groups; (d) amino acids with negatively charged R groups and (e) amino acids with aromatic R groups.

The naturally occurring amino acids, but also other than naturally occurring amino acids such as artificial amino acids, can be classified into the above characteristic groups (Nelson D.L. & Cox M.M., "Lehninger Biochemie" (2005), pp. 122-127), from which at least three amino acids are selected for the solution according to the invention.

In a more preferred embodiment, the at least three amino acids are selected from different groups (a) to (e). In other words, in this preferred embodiment, when three amino acids are comprised in the solution, the three amino acids may be selected from at least two different groups and, more preferably, from three different groups such that one is from group (a), one is from group (b) and one is from group (c). Further combinations such as e.g. (b)-(c)-(d), (c)-(d)-(e), (e)-(a)-(b), (b)-(d)-(e) and so forth are also explicitly envisaged herein. The same consideration applies when four amino acids are comprised in the solution, in which case the amino acids have to be from at least two different groups selected from (a) to (e), more preferably from at least three different groups and most preferably from four different groups. Inter alia, when five amino acids are comprised in the solution, the amino acids have to be from at least two different groups selected from (a) to (e), more preferably from at least three different groups, more preferably from at least four different groups and most preferably from five different groups. The same considerations apply when more than five amino acids are comprised in the solution, such as e.g. six or seven amino acids, in which case these amino acids are selected from at least two different groups selected from (a) to (e), more preferably from at least three different groups, even more preferably from at least four different groups and most preferably from five different groups.

In an even more preferred embodiment of the method of the invention, the solution comprises at least one amino acid selected from each group of (a) an amino acid with non polar, aliphatic R groups; (b) an amino acid with polar, uncharged R groups; (c) an amino acid with positively charged R groups; (d) an amino acid with negatively charged R groups and (e) an amino acid with aromatic R groups.

The skilled person further understands that it is not necessary that the same number of amino acids of each group is present in the solution used according to the invention. Rather, any combination of amino acids can be chosen as long as at least one amino acids of each group is present.

Furthermore, the amino acids can be present in the solution as singular molecules and/or as di- and/or tripeptides.

In another preferred embodiment of the method of the invention, the solution comprises at least the amino acids: (a) alanine, glutamate, lysine, threonine and tryptophane; (b) aspartate, arginine, phenylalanine, serine and valine; (c) proline, serine, asparagine, aspartate, threonine, phenylalanine; (d) tyrosine, isoleucine, leucine, threonine, valine; or (e) arginine, glycine, histidin, alanine, glutamate, lysine, tryptophane. In another preferred embodiment, the solution comprises at least the amino acids: (f) alanine, arginine, glycine, glutamate, lysine.

In accordance with this embodiment, at least the above recited amino acids of either group (a), (b), (c), (d) or (e) are present in the solution in accordance with the invention. In other words, whereas more than the above recited amino acids may be comprised in the inventive solution, it is required that at least the recited amino acids are present. More preferably, the solution comprises exactly the recited amino acids and no other amino acids. The same consideration apply mutatis mutandis to the amino acids of group (f).

In another preferred embodiment of the method of the invention, one or more of the amino acids are selected from the group consisting of natural non-proteinogenic and synthetic amino acids.

The term "non-proteinogenic amino acids", in accordance with the present invention, relates to amino acids that are not naturally incorporated into polypeptides and proteins. Non-proteinogenic amino acids can be derived from proteinogenic amino acids, which are L-α-amino acids, by post-translational modifications. Such non-proteinogenic amino acids are, for example, lanthionine, 2-aminoisobutyric acid, dehydroalanine, and the neurotransmitter gamma-aminobutyric acid. Also the D-enantiomers of proteinogenic L-amino acids represent non-proteinogenic amino acids. Further non-limiting examples of non-proteinogenic amino acids include carnitine, creatine, creatinine, guanidinoacetic acid, ornithine, hydroxyproline, homocysteine, citrulline, hydroxylysine or beta-alanine.

The term "synthetic amino acids", as used herein, relates to amino acids not naturally occurring in nature. Non-limiting examples of synthetic amino acids include (2R)-amino-5-phosphonovaleric acid, D-phenyl glycine or (S)- and (R)-tert-leucine.

In another preferred embodiment, the (poly)peptide is selected from the group consisting of therapeutic proteins, like antibodies, growth factors, cytokines, protein or peptide hormones, growth hormones, blood factors, therapeutic enzymes, therapeutic vaccines or fragments thereof which retain their biological activity. These (poly)peptides can be used, for example, for therapeutic or diagnostic purposes. Such purposes are well known in the art.

The term "antibody" includes polyclonal or monoclonal antibodies as well as derivatives thereof which retain their binding specificity. The term also includes synthetic, chimeric, single chain and humanized antibodies or derivatives or fragments thereof, which still retain their binding specificity. Fragments of antibodies comprise, inter alia, Fab fragments, F(ab')$_2$ or Fv fragments. Techniques for the production of antibodies and fragments thereof are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1998. Further, transgenic animals may be used to express humanized antibodies. Most preferably, the antibody is a monoclonal antibody. For the preparation of monoclonal antibodies, any technique that provides antibodies produced by continuous cell line cultures can be used. Examples for such techniques include the hybridoma technique (Kohler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). The antibody may be any class of antibody. It is most preferred that the antibody is monoclonal and of the IgG, IgM or IgY class. IgY antibodies represent the analogs of IgG antibodies in chicken.

The term "growth factor" as used herein refers to proteins that bind to receptors on the cell surface, with the primary result of activating cellular proliferation and/or differentiation. Many growth factors are versatile, stimulating cellular division in numerous different cell types, while others are specific to a particular cell-type. Preferred growth factors in accordance with the present invention include, without being limiting, erythropoietin, insulin-like growth factor 1 (IGF-1, originally called Somatomedin C) and insulin-like growth factor 2 (IGF-2).

The term "cytokine", in accordance with the present invention, relates to a class of signalling proteins that are used extensively in cellular communication, immune function and embryogenesis. Cytokines are produced by a variety of hematopoietic and non-hematopoietic cell types and can exert autocrine, paracrine and endocrine effects as do the hormones. However, many cytokines exhibit growth factor activity. Cytokine are a unique family of growth factors. Secreted primarily from leucocytes, cytokines stimulate both the humoral and cellular immune responses as well as the activation of phagocytic cells. Cytokines that are secreted from lymphocytes are termed lymphokines, whereas those secreted by monocytes or macrophages are termed monokines. A large family of cytokines are produced by various cells of the body. Many of the lymphokines are known as interleukines (ILs), since they are not only secreted by leukocytes but also able to affect the cellular responses of leukocytes. Specifically, interleukines are growth factors targeted to cells of hematopoietic origin. Cytokines include, without being limiting, interleukins, interferons, granulocyte colony-stimulating factor (G-CSF), granulocyte-macrophage colony-stimulating factor (GM-CSF) and bone morphognetic protein-2 (BMP-2).

The term "protein or peptide hormones" refers to a class of peptides that are secreted into the blood stream and have endocrine functions in living animals. Like other proteins, peptide hormones are synthesized in cells from amino acids according to an mRNA template, which is itself synthesized from a DNA template inside the cell nucleus. Peptide hormone precursors (pre-prohormones) are then processed in several stages, typically in the endoplasmic reticulum, including removal of the N-terminal signal sequence and sometimes glycosylation, resulting in prohormones. The prohormones are then packaged into membrane-bound secretory vesicles, which can be secreted from the cell by exocytosis in response to specific stimuli e.g. increase of calcium and cAMP concentration in cytoplasm. These prohormones often contain superfluous amino acid residues that are needed to direct folding of the hormone molecule into its active configuration but have no function once the hormone folds. Specific endopeptidases in the cell cleave the prohormone just before it is released into the bloodstream, generating the mature hormone form of the molecule. Mature peptide hormones then diffuse through the blood to all of the cells of the body, where they interact with specific receptors on the surface of their target cells. Some peptide/protein hormones (angiotensin II, basic fibroblast growth factor-2, parathyroid hormone-related protein) also interact with intracellular receptors located in the cytoplasm or nucleus by an intracrine mechanism. Several important peptide hormones are secreted from the pituitary gland. The anterior pituitary secretes prolactin, which acts on the mammary gland, adrenocorticotrophic hormone (ACTH), which acts on the adrenal cortex to regulate the secretion of glucocorticoids, and growth hormone, which acts on bone, muscle, and the liver. The posterior pituitary gland secretes antidiuretic hormone, also called vasopressin, and oxytocin. Peptide hormones are produced by many different organs and tissues, however, including the heart (atrial-natriuretic peptide (ANP) or atrial natriuretic factor (ANF)) and pancreas (insulin and somatostatin), the gastrointestinal tract cholecystokinin, gastrin), and adipose tissue stores (leptin). Some neurotransmitters are secreted and released in a similar fashion to peptide hormones, and some 'neuropeptides' may be used as neurotransmitters in the nervous system in addition to acting as hormones when released into the blood. When a peptide hormone binds to receptors on the surface of the cell, a second messenger appears in the cytoplasm, which triggers intracellular responses. Peptide hormones include without being limited Insulin, Glucagon, Gonadotropin, human Thyroid Stimulating Hormone, angiotensin II, basic fibroblast growth factor-2, parathyroid hormone-related protein, vasopressin, oxytocin, atrial-natriuretic peptide (ANP) or atrial natriuretic factor (ANF), somatostatin, cholecystokinin, gastrin, and adipose tissue stores (leptin).

The term "growth hormone" (GH) refers to a protein-based peptide hormone consisting of a 191-amino acid, single-chain polypeptide, stored and secreted by somatotroph cells within the lateral wings of the anterior pituitary gland. Effects of growth hormone on the tissues of the body can generally be described as anabolic (building up). Like most other protein hormones, it acts by interacting with a specific receptor on the surface of cells. Increased height during childhood is the most widely known effect of GH. Height appears to be stimulated by at least two mechanisms: 1. because polypeptide hormones are not fat-soluble, they cannot penetrate sarcolemma. Thus, GH exerts some of its effects by binding to receptors on target cells, where it activates the MAPK/ERK pathway. Through this mechanism GH directly stimulates division and multiplication of chondrocytes of cartilage. 2. GH also stimulates, through the JAK-STAT signaling pathway, the production of insulin-like growth factor 1 (IGF-1, formerly known as somatomedin C), a hormone homologous to proinsulin. The liver is a major target organ of GH for this process and is the principal site of IGF-1 production. IGF-1 has growth-stimulating effects on a wide variety of tissues. Additional IGF-1 is generated within target tissues, making it what appears to be both an endocrine and an autocrine/paracrine hormone. IGF-1 also has stimulatory effects on osteoblast and chondrocyte activity to promote bone growth. In addition to increasing height in children and adolescents, growth hormone has many other effects on the body: increases calcium retention, and strengthens and increases the mineralization of bone, increases muscle mass through sarcomere hyperplasia, promotes lipolysis, increases protein synthesis, stimulates the growth of all internal organs excluding the brain, plays a role in homeostasis, reduces liver uptake of glucose, promotes gluconeogenesis in the liver, contributes to the maintenance and function of pancreatic islets, stimulates the immune system.

Somatotropin refers to the growth hormone 1 produced naturally in animals, whereas the term somatropin refers to growth hormone produced by recombinant DNA technology, and is abbreviated "HGH" in humans. It stimulates growth, cell reproduction and regeneration.

The term "blood factors" refers to proteins that govern the functions of the blood coagulation cascade. The coagulation cascade of the human body comprises of a series of complex biochemical reactions, which are regulated by the blood factor proteins. These proteins include, for example, the pro-coagulation factors, such as Factor VIII and Factor IX, as well as anticoagulation factors, including Protein C and Antithrombin Ill.

As used herein, the term "therapeutic enzymes" refers to proteins that catalyse chemical reactions, thereby converting a starting molecule, the substrate, into a different molecule, the product. The function of therapeutic enzymes depends directly on their molecular structure and conformation. Irreversible conformational changes and irreversible aggregation lead to inactivation of the therapeutic enzymes. Preferred enzymes in accordance with the present invention include, without being limiting, therapeutic enzymes for the treatment of lysosomal storage diseases by enzyme replacement therapy, i.e. human 3-glucocerebrosidase (Gaucher disease), human galactosidase A (Fabry disease), thrombolytic drugs, i.e. sreptokinase (thrombolytic agent in treatment of ischemic stroke), urokinase, (recombinant) tissue plasminogen activator, TNKase; L-asparaginase (cytostatic drug), urate oxidase, papain.

The term "therapeutic vaccines", in accordance with the present invention, relates to the immunogenic parts of an attenuated or killed pathogen (antigen), the antigenic components of virus lysates or a recombinantly produced individual proteinogenic virus antigens.

A large number of suitable methods exist in the art to produce (poly)peptides. For example, (poly)peptides may be produced in appropriate hosts. If the host is a unicellular organism such as a prokaryote, a mammalian or insect cell, the person skilled in the art can revert to a variety of culture conditions. Conveniently, the produced (poly)peptide is harvested from the culture medium, lysates of the cultured organisms or from isolated (biological) membranes by established techniques. In the case of a multicellular organism, the host may be a cell which is part of or derived from a part of the organism, for example said host cell may be the harvestable part of a plant. A preferred method involves the recombinant production of (poly)peptides in hosts as indicated above. For example, nucleic acid sequences encoding the (poly)peptide to be folded/prevented from unfolding according to the invention can be synthesized by PCR and inserted into an expression vector. Subsequently a suitable host may be transformed with the expression vector. Thereafter, the host is cultured to produce the desired (poly) peptide(s), which is/are isolated and, optionally, purified before use in the method of the invention.

An alternative method for producing the (poly)peptide to be employed in the method of the invention is in vitro translation of mRNA. Suitable cell-free expression systems include rabbit reticulocyte lysate, wheat germ extract, canine pancreatic microsomal membranes, *E. coli* S30 extract, and coupled transcription/translation systems such as the TNT-system (Promega). These systems allow the expression of recombinant (poly)peptides upon the addition of cloning vectors, DNA fragments, or RNA sequences containing coding regions and appropriate promoter elements.

In addition to recombinant production, the (poly)peptide to be employed in the method of the invention may be produced synthetically, e.g. by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154). Synthetic peptide synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. As indicated above, chemical synthesis, such as the solid phase procedure described by Houghton Proc. Natl. Acad. Sci. USA (82) (1985), 5131-5135, can be used. Furthermore, the (poly)peptide may be produced semi-synthetically, for example by a combination of recombinant and synthetic production.

(Poly)peptide isolation and purification can be achieved by any one of several known techniques; for example and without limitation, ion exchange chromatography, gel filtration chromatography and affinity chromatography, high pressure liquid chromatography (HPLC), reversed phase HPLC, and preparative disc gel electrophoresis.

In another preferred embodiment of the method of the invention, the solution further comprises a saponine or a fatty acid or derivatives thereof.

Saponines are a class of chemical compounds forming secondary metabolites which are found in natural sources, derived from natural sources or can be chemically synthesized. Saponines are found in particular abundance in various plant species. Saponines are amphipathic glycosides grouped phenomenologically by the soap-like foaming they produce when shaken in aqueous solutions, and structurally by their composition of one or more hydrophilic glycoside moieties combined with a lipophilic steroidal or triterpenoid aglycone. Their structural diversity is reflected in their physicochemical and biological properties. Examples of saponines are glycyrrhicic acid, glycyrrhetinic acid, glucuronic acid, escin, hederacoside and digitonin.

Fatty acids are carboxylic acids with a long unbranched aliphatic chain (tail) that may be saturated or unsaturated. They are important energy sources because their metabolism yields large quantities of ATP. The majority of naturally occurring fatty acids have a chain of an even number of carbon atoms, from four to 28 and are usually derived from triglycerides or phospholipids. Fatty acids have different lengths, which is used to categorise them as short-, medium-, or long-chain fatty acids. Short-chain fatty acids (SCFA) are fatty acids with aliphatic tails of fewer than six carbons; medium-chain fatty acids (MCFA) are fatty acids with aliphatic tails of 6-12 carbons, which can form medium-chain triglycerides; long-chain fatty acids (LCFA) are fatty acids with aliphatic tails longer than 12 carbons and very-long-chain fatty acids (VLCFA) are fatty acids with aliphatic tails longer than 22 carbons. Non-limiting examples of fatty acids include unsaturated fatty acids such as e.g. myristoleic acid, palmitoleic acid, sapienic acid, oleic acid, linoleic acid, α-linolenic acid, arachidonic acid, eicosapentaenoic acid, erucic acid and docosahexaenoic acid or saturated fatty acids such as e.g. lauric acid, myristic acid, palmitic acid, stearic acid, arachidic acid, behenic acid, lignoceric acid and cerotic acid.

In another more preferred embodiment of the method of the invention, the saponine is glycyrrhizic acid or a derivative thereof.

Glycyrrhizic acid is also known as glycyrrhicic acid, glycyrrhizin or glycyrrhizinic acid and has the structure:

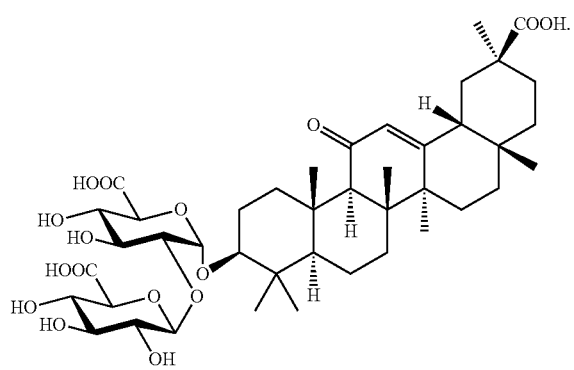

Glycyrrhizic acid is water-soluble and exists as an anion that can be a potential ligand to form electrostatically associated complexes with cationic molecule active ingredients. Without wishing to be bound by theory, the present inventors hypothesize that the anionic glycyrrhizic acid forms complexes with amino acids present in the solution of the present invention (i.e. arginine, or lysine) through electrostatic interactions, hydrogen bonds or both. This complexation is thought to enhance the ability of the solution of the present invention to maintain the native three-dimensional structure of proteins. Moreover, the ability of glycyrrhizic acid to form complexes with cationic molecule active ingredients can lead to interactions with exposed cationic side chains on the protein surface during the drying process, thus resulting in a further stabilization of the native protein structure.

Derivatives of glycyrrhizic acid are well-known in the art and include those produced by transformation of glycyrrhizic acid on carboxyl and hydroxyl groups, by conjugation of amino acid residues into the carbohydrate part or the introduction of 2-acetamido-β-D-glucopyranosylamine into the glycoside chain of glycyrrhizic acid. Other derivatives are amides of glycyrrhizic acid, conjugates of glycyrrhizic acid with two amino acid residues and a free 30-COOH function and conjugates of at least one residue of amino acid alkyl esters in the carbohydrate part of the glycyrrhizic acid molecule. Examples of specific derivatives can be found e. g. in Kondratenko et al. (Russian Journal of Bioorganic Chemistry, Vol 30(2), (2004), pp. 148-153).

In accordance with the present invention, it was surprisingly found that addition of glycyrrhizic acid to the above described solution further aids in the folding or refolding of a (poly)peptide and the prevention of unfolding thereof. In particular, glycyrrhizic acid was found to reduce aggregation of (poly)peptides that are usually prone to unwanted aggregate formation. Thus, addition of glycyrrhizic acid aids in maintaining or re-establishing the biological activity of a (poly)peptide by enhancing or supporting the correct folding thereof into the three-dimensional structure required for activity.

In another more preferred embodiment of the method of the invention, the fatty acid is selected from the group consisting of short chain and medium chain fatty acids.

Short chain and medium chain fatty acids are particularly preferred due to their better solubility in water as compared to fatty acids with longer chains.

In another preferred embodiment of the method of the invention, the w/w ratio between excipients of the solution and the (poly)peptide is between about 1:1 and about 500:1.

In accordance with this embodiment, the excipients of the solution are the non-aqueous components of the solution that are not the (poly)peptide to be folded or protected from unfolding.

More preferably, the w/w ratio between the components of the solution and the (poly)peptide is between about 1:1 and about 350:1, such as for example between about 5:1 and about 200:1, or between about 10:1 and about 100:1. Most preferably, the w/w ratio is about 2:1. It will be understood that any value falling between these ratios is explicitly also envisaged herein. Furthermore, the term about, as used herein, encompasses the explicitly recited ratios as well as deviations therefrom of ±10%.

In another preferred embodiment of the method of the invention, the (poly)peptide is a recombinant (poly)peptide.

In a further preferred embodiment of the method of the present invention, the (poly)peptide has one or more intramolecular disulfide bonds.

(Poly)peptide may be stabilized by the formation of at least one intra- or inter-molecular disulfide bridges. Suitable cysteine residues may be naturally occurring in the (poly)peptide or may be introduced into the (poly)peptide by mutating appropriate amino acids to cysteine. For example, it been disclosed in WO 2009/007124 that the introduction of disulfide bridges into immunoglobulin domains of scFvs greatly enhances the stability of these molecules, without affecting their specificity or reducing their affinity and functionality and without a loss of solubility of the molecule.

In another preferred embodiment of the method of the invention, the folded (poly)peptide is biologically active.

The term "biologically active" relates to the naturally occurring activity of a (poly)peptide. Biological activities depend on the specific (poly)peptide and include binding affinity to other molecules (e.g. for antibodies, ligands or transcription factors) or catalytic activities (e.g. for enzymes). The biological activity of an antibody, for example, requires the specific binding of its antigen. In this regard, the term "is biologically active" refers to a biological activity of the folded or re-folded (poly)peptide (i.e. after drying and reconstitution) that is at least 50%, more preferably at least 60%, more preferably at least 70% and most preferably at least 80% of the naturally occurring biological activity of said (poly)peptide. More preferably, the biological activity of the folded or re-folded (poly)peptide is at least 90%, more preferably 100% of the naturally occurring biological activity of said (poly)peptide.

As described herein above, the biological activity of any given (poly)peptide directly depends from its three-dimensional structure. Therefore, by providing a method of (re-) folding a (poly)peptide and/or preventing unfolding of a (poly)peptide, a method of maintaining or recovering the biological activity of said (poly)peptide is provided herein. It will be appreciated that the biological activity of the (poly)peptide may be recovered in the case of refolding and may be maintained in the case of preventing unfolding.

The term "dried preparation", as used herein, refers to a preparation in which the liquid content has been removed or reduced. Suitable methods for drying a viral or bacterial preparation include, without being limiting, lyophilisation (freeze-drying), spray-drying, spray-freeze drying, air drying or foam drying.

The liquid content is considered to have been reduced if the liquid is reduced to less than 20% of the volume, such as for example less than 10%, such as for example less than 5%, more preferably less than 3% of the volume, such as less than 2% or less than 1%. Most preferably, the liquid is reduced to 0.5% or less.

In a further preferred embodiment of the method of the invention, the drying is freeze-drying, spray-drying, air-drying, spray-freeze-drying or foam-drying.

Lyophilisation, also referred to as freeze-drying, is well known in the art and includes the steps of freezing the organic material and subsequently reducing the surrounding pressure while adding sufficient heat to allow the frozen water in the material to sublime directly from the solid phase to the gas phase. Preferably, the lyophilised preparation is then sealed to prevent the re-absorption of moisture.

Spray-drying is also well known in the art and is a method to convert a solution, suspension or emulsion into a solid powder in one single process step. Generally, a concentrate of the liquid product is pumped to the atomising device, where it is broken into small droplets. These droplets meet a stream of hot air and they loose their moisture very rapidly while still suspended in the drying air. The dry powder is separated from the moist air in cyclones by centrifugal action—the dense powder particles are forced toward the cyclone walls while the lighter, moist air is directed away through the exhaust pipes.

Air-drying is achieved by exposing the sample to the air until the humidity has been reduced or entirely removed.

Spray-freeze-drying is also well known in the art and is a method that combines processing steps common to freeze-drying and spray-drying. The (poly)peptide provided in the solution according to the invention is nebulized into a cryogenic medium (such as e.g. liquid nitrogen), which generates a dispersion of shock-frozen droplets. This dispersion is then dried in a lyophiliser.

Foam drying is a scalable technology for preservation of sensitive biotherapeutics in the dry state. Vacuum foam drying (VFD) can be used to stabilize therapeutic biomolecules that are stable at moderate temperatures and pressures, such as erythropoeitin, enzymes, and vaccines. The suspension or solution of biologicals is transformed into foam by boiling under vacuum, above freezing point, but significantly below 100° C. The foam consists of thin films of material from which water can be efficiently removed at an elevated temperature. The process is based on the principle of evaporation under vacuum at low temperatures.

In accordance with this embodiment, a (poly)peptide that has previously been stored under dry or amorphous conditions, i.e. as a lyophilised or spray dried composition, can be reconstituted by the method of the present invention. It was surprisingly shown that in the presence of the inventive solution, (poly)peptides can be refolded into their native state without a loss of activity and their structural integrity, respectively.

As discussed herein above, the dried proteins offer the advantage of being more resistant to temperature stresses, thus rendering them particularly stable during storage e.g. under conditions lacking a continues cold-chain. In addition, and as shown in the appended examples, a sterilisation of the dried proteins is possible without a loss of the native three-dimensional structure of the proteins. Thus, the present invention enables the sterilization of a protein preparation in order to reduce the number of bacteria and/or viruses while protecting the proteins from degradation due to β-, γ- or X-ray-radiation. Consequently, time and costs involved in the preparation of therapeutic proteins under sterile conditions are reduced.

Unless otherwise defined, all technical and scientific terms used herein have the same meaning as commonly understood by one of ordinary skill in the art to which this invention belongs. In case of conflict, the patent specification, including definitions, will prevail.

The figures show:
The examples illustrate the invention:

Example 1: Materials and Methods

Embedding Solution

The protective embedding solution was prepared by combining different amino acids L-alanine, L-arginine, L-glutamic acid, glycine, L-histidine, L-lysine monohydrochloride and L-tryptophan—and optionally glycyrrhizic acid—to reach a stock concentration of 100 g/L. The weight:weight (w/w) ratio of the final solution (1-25 g/L) used for specifically protecting proteins was >2:1. All components were non-toxic. Amino acids are approved for intravenous infusion (Fong and Grimley). Glycyrrhizic acid has been approved for intravenous application in the treatment of chronic hepatitis, and its safety has been well documented in several clinical studies.

In the embedding solution, glycyrrhizic acid can be used in a range between 1-10000 μg/mL.

Preparation of Bio-Functionalized PU Surfaces

Open porous medical-grade polyurethane foams (KCl, San Antonio, Tex., USA) were cut into 3 cm³ cylindrical samples and coupling with 4 μg/mL anti-Fas IgM (clone CH11) was done for 1 h. After washing the samples four times with phosphate-buffered saline (PBS), nonspecific reaction sites were blocked. The samples were washed with $H_2O$, and the embedding step was performed with 25 mg/mL embedding solution for 30 min and subsequent drying for at least 90 min. Sterilization was performed with β-irradiation at 25 kGy (BGS, Bruchsal, Germany).

X-Ray Diffraction

Wide-angle X-ray diffraction (XRD) was used to study the morphology of the dried layer of the embedding solution. The X-ray diffractometer XRD 3000 TT (Seifert, Germany) equipped with a copper anode (40 kV, 30 mA, wavelength 0.154 nm) and a scintillation counter was used. The dried films were placed in the sample carrier and analyzed in the angular range from 50 to 45° 2θ, with steps of 0.05° 2θ and a duration of 2 s per step. The analyses were performed by Coriolis Pharma Service GmbH (Munich, Germany).

Differential Scanning Calorimetry

Differential scanning calorimetry (DSC) in a Mettler Toledo 821e (Giessen, Germany) was used to determine the glass transition temperature of the maximally freeze-concentrated solution ($T_g'$) of the liquid formulations. The $T_g'$ samples were cooled to −80° C. at a cooling rate of approximately 10 κ/min. The midpoint of the endothermic shift of the baseline was taken as $T_g'$. The analyses were performed by Coriolis Pharma Service GmbH (Munich, Germany).

Spectral Reflectance

The thin film's characteristics were measured by reflecting light off the film and analyzing the resulting reflectance spectrum over a range of wavelengths (Filmetrics Inc., Munich, Germany). Light reflected from different interfaces of the film can be in- or out-of-phase, so these reflections add or subtract, depending on the wavelength of the light and the film's thickness and index. The result is intensity oscillations in the reflectance spectrum that are characteristic of the film. To determine the film's thickness, specific software (Filmetrics Inc.) was used to calculate a theoretical reflectance spectrum that was matched as closely as possible to the measured spectrum. The process began with an initial estimation of what the reflectance spectrum should look like, based on the nominal film stack. This included information on the thickness and refractive index of the different layers and the substrate that comprises the sample. The theoretical reflectance spectrum was then adjusted by the film's properties until a best fit to the measured spectrum was found.

Viscosity Measurements

The viscosity of the samples was determined using a falling ball viscosimeter (model AMVn, Anton Paar, Ostfildern, Germany) at 25° C. with an angle of α=60°. The AVMn measures the rolling time of a ball through transparent and opaque liquids according to the rolling ball principle. Each measurement consisted of 10 runs followed by the calculation of the average viscosity. The analyses were performed by Coriolis Pharma Service GmbH (Munich, Germany).

Small-Angle X-Ray Scattering

All small-angle X-ray scattering (SAXS) experiments were performed with Cu Kα radiation emitted by a rotating anode generator (Nanostar, BRUKER AXS). The system was equipped with a pinhole camera and an area detector (VANTEC 2000). Samples were fixed onto a stage-holder. The SAXS intensity patterns were taken at a sample-to-detector distance of 109 cm for 20 min to 6 h. All data were corrected for background scattering and then radially averaged to obtain the function I(Q), where $Q=(4\pi/\lambda)\sin\theta$ is the scattering vector, 2θ is the angle between the incident and diffracted beam, and λ=0.1542 nm is the X-ray wavelength. We chose the homologous solution structure of human IgM (2RCJ) (Perkins et al.) as the initial configuration, to which SAXS fit and applied an in-house fitting code. Using an MC algorithm, we randomly created scatters with the restriction that their position was within a size limit of 2 nm with respect to the homologous model. The homologous model was thus refined by the SAXS data but served as a permanent corrective of the numerical reconstruction procedure after each step. The final fitted scattering curves for the monomer and the self-assemblies are provided.

Sterilization

Sterilization was performed by Beta-Gamma Service (Bruchsal, Germany) using β-irradiation at 25-40 kGy.

With regard to the validation of sterility according to ISO 11137 $VD_{max}$ (Paunel-Gorgulu, Logters, et al.), the main question was whether embedding favors growth of bacteria/fungi. Sampling was performed by sterile rinsing of the housings and collecting the fluids in a sterile container. After membrane filtration of the samples, membranes were transferred to CASO Agar plates for the determination of colony-forming units of aerobic bacteria, fungi, and spore-forming bacteria. The analysis was performed by Medical Device Services (MDS, Munich, Germany).

Virus Infectivity Assay

For the infectivity/inactivation study, adenovirus type 5, strain Adenoid 75 (American Type culture collection, ATCC-VR-5) was propagated on human lung cancer cell line A549 (ATTC-CCL-185). For virus propagation, cells were grown at 37° C. and 5% $CO_2$ in minimum essential medium (MEM) supplemented with 5% fetal calf serum (FCS). The virus titer was determined by means of end-point titration (eight wells per dilution in a 96-well microtiter plate), with 50 μL virus dilution and 50 μL A549 cells ($10\text{-}15\times10^3$ cells) per well. For the experiments, a titer of $1.1\times10^9$ tissue culture infectious dose (TCID50)/mL was used. Specifically, a volume of 50 μL virus suspension was dried at 37° C. on the bottom of sterile polystyrol tubes. The dried virus was then overlaid by 50 μL of the embedding solution and dried again at 37° C. After β-irradiation at 25 kGy or 40 kGy (controls were not irradiated), the virus/protective solution bilayer was resuspended in 1 mL MEM. The virus titer was determined again as described above. The cultures were observed for cytopathic effects (CPE) after 7 days of inoculation. Virus controls were treated identically but without β-irradiation. The virus titers are expressed as TCID50/mL including standard deviation. Titer reduction is expressed as the difference between the virus titer after β-irradiation and control virus titer.

Functional Characterization

ELISA: For the gross quantification of the amount of immobilized IgM on the surface of open porous polyurethane foams, an enzyme-linked immunosorbent assay (ELISA) was developed. As a detecting antibody, a horseradish peroxidase (HRP)-conjugated goat-anti-mouse IgM antibody was used. TMB (3,3',5,5'-tetramethylbenzidine; Sigma) was used for the substrate reaction.

Antigen binding: To obtain information on the specific functionality of the immobilized anti-Fas IgM, experiments were performed with recombinant antigens. Recombinant hFas:Fc protein was purified from Chinese hamster ovary cells stably transfected with an hFas:Fc expression plasmid (ps299-hFasFc; provided by Pascal Schneider, Lausanne, Switzerland) using HiTrap Protein A column one-step purification according to standard procedures. The bioactivity of hFas:Fc was tested by inhibiting FasL-mediated cell death of RKO cells (human colon carcinoma cell line) and flow cytometric quantification of cells with hypoploid DNA content by propidium iodide staining (Nicoletti et al.).

Peptide binding: Peptide arrays of isoform 1 of human Fas (aa 1-177 and permutated peptides; accession no. P25445) were synthesized by Fmoc chemistry at activated PEG-spacers on cellulose membranes by automated parallel peptide synthesis on a MultiPep RS instrument (Intavis, Köln, Germany) as described previously (Brandt, Dietrich and Koch; Koch and Mahler). Interaction studies with antibodies were performed according to published procedures (Hilpert, Winkler and Hancock; Koch and Mahler). Bound antibodies were visualized by chemiluminescence imaging. Selected soluble epitope peptides carrying N-terminal biotinylation were obtained from Diana Imhof (Institute of Biochemistry, University of Jena, Germany).

Apoptosis induction in T-cells and neutrophils: For the evaluation of clinically relevant function, Fas-negative and Fas-positive T-cells (Jurkat cell line) and freshly isolated neutrophils from trauma patients (study approval was obtained from the Ethics Review Board of the University of Duesseldorf, Germany) were challenged with PU-IgM$_{Fas}$ for 4 h. Subsequently, cells were harvested, and apoptosis was determined by staining the cells with propidium iodide. Flow cytometry followed the protocol of Nicoletti (Nicoletti et al.).

Statistics

All experiments were done at least five times. Where relevant, data are presented as mean+/−SEM. Statistical analyses were performed by Student's t-Test (GraphPad Prism Program, version 5, GraphPad Software, San Diego, Calif.). P values of less than 0.05 were considered statistically significant.

Example 2: Physical Characteristics of the Inventive Solution

Although sugars are generally employed lyoprotectants because of their solubility and OH groups to form hydrogen bonds, their rapid crystallization at higher concentrations is a clear disadvantage (Y. Han et al.). Given an initial molar ratio of 500:1 (sugar:protein), this ratio is further increased during the drying process. Therefore, crystallization occurs, which reduces the availability of sugar molecules and consequently their capacity to provide hydrogen bonds. We found that some glycosidic plant metabolites, such as glycyrrhizic acid (FIG. 1), act as suitable lyoprotectants, possibly because of the presence of glycoside OH groups.

By contrast to saccharides, the therapeutically approved saponin glycyrrhizic acid (Baltina) does not crystallize but rather forms an amorphous gel (glassy state), particularly when combined with amino acids, (Fuchs et al.) thereby providing the OH groups for the formation of hydrogen bonds until the protein is entirely dried. In order to investigate whether the glassy state of the solution in accordance with the present invention, comprising glycyrrhizic acid in combination with selected amino acids, helps to prevent undesirable microcrystal formation during freezing and drying, several experimental approaches were followed (see below).

Figure 2A:
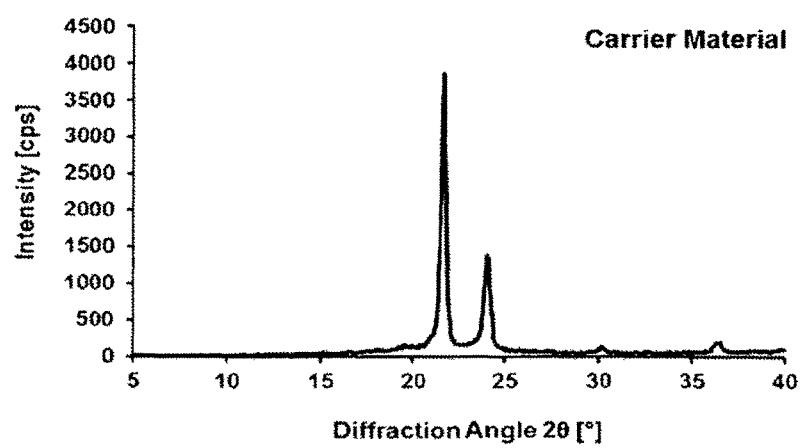
Figure 2B:
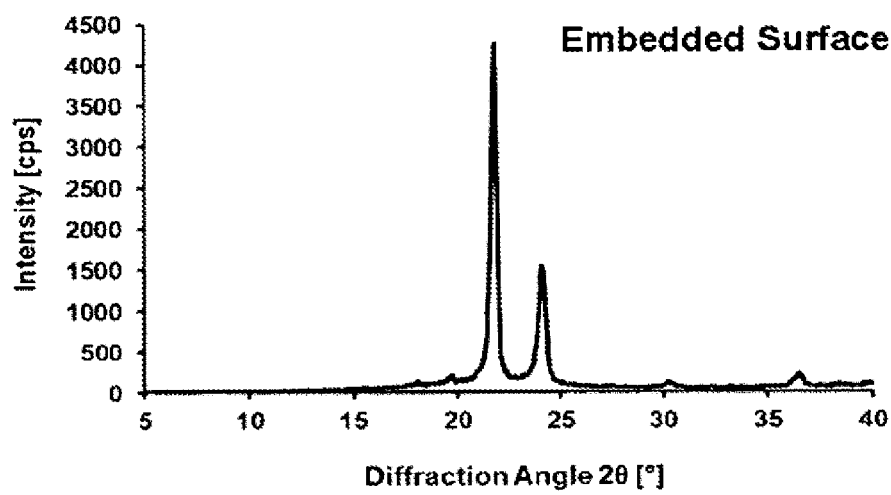
Figure 2C:
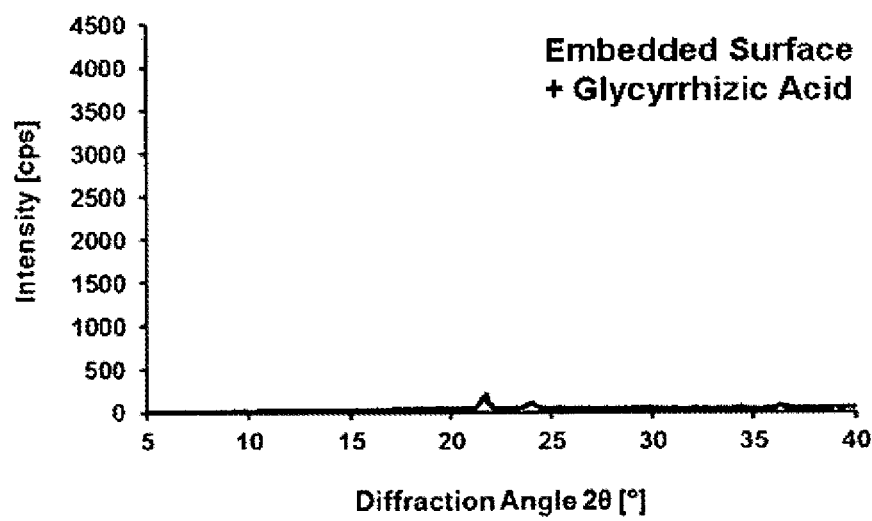
Figure 2D:
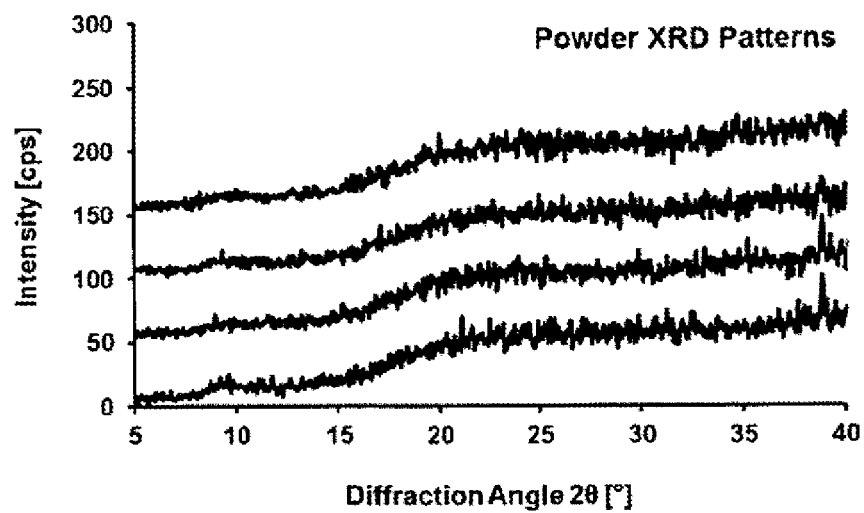

The physical nature of dried films of the inventive solution on a carrier material was determined by wide-angle X-ray diffraction (XRD) (FIG. 2A-C). The XRD patterns of the coated surfaces showed four characteristic peaks for the used carrier material (FIG. 2A). Coating of this material with co-solvent solution devoid of glycyrrhizic acid resulted in the same XRD pattern, suggesting an amorphous structure without additional crystallization peaks (FIG. 2B). Supplementation of the solution in accordance with the present invention with glycyrrhizic acid led to a more pronounced amorphous character and resulted in interference with the diffraction signal of the coated carrier (FIG. 2C). Moreover, antibody solids, freeze-dried in the presence of the solution in accordance with the present invention, displayed halo powder XRD patterns (FIG. 2D), which are typical for non-crystalline solids. The absence of peaks suggests that the analyzed samples were present in an amorphous state.

Analysis of the frozen co-solvent solution by differential scanning calorimetry (DSC) revealed two thermal transitions of the freeze-concentrated non-ice phase ($T_g$': glass transitions of maximally freeze-concentrated phases): $T_g1'$ at −60° C. and $T_g2'$ at −49° C., which are typical for amino acids. No characteristic crystallization events were found in the thermograms of the frozen solution in accordance with the present invention (FIG. 3A). Additionally, the DSC thermograms of antibody solids, freeze-dried in the presence of the solution in accordance with the present invention, were consistent with amorphous solids without any evidence of crystallization (FIG. 3B).

In order to investigate whether the inventive solution can form homogenous thin films on surfaces, spectral reflectance analyses were performed on silicium coated with a mannitol (sugar alcohol)-albumin mixture or with the solution in accordance with the present invention (FIG. 4). Spectral reflectance showed crystallization of mannitol in the mannitol-albumin mixture (FIG. 4A), whereas a homogenous film was formed in the presence of the solution in accordance with the present invention (FIG. 4B). The corresponding oscillation curves confirmed the crystalline and amorphous layer characteristics, respectively (data not shown). Films of the solution in accordance with the present invention displayed a viscosity of 1.15 mPa*s (water: 0.89 mPa*s) and a thickness in the low nanometer range in accordance with the observed characteristic "rainbow" effect (FIG. 4C).

Based on the determined key physical parameters of the solution in accordance with the present invention we concluded—and further tested—that the inventive solution is suitable for the stabilization of proteins during freeze-drying.

Example 3: Structural Stabilization of the Anti-Fas IgM by the Solution in Accordance with the Present Invention, Monitored by Small-Angle X-Ray Scattering (SAXS)

The goal of embedding in the solution in accordance with the present invention is to preserve the structural and functional integrity of proteins during e.g. storage or sterilization procedures. The protective effect of the inventive solution on the integrity of the three-dimensional structure of polyurethane (PU)-IgMFas after drying (FIG. 5B), β-irradiation, and rehydration (FIGS. 5C and D) was analyzed by SAXS (Horejs, Gollner, et al.; Horejs, Pum, et al.).

The measured background-corrected scattering contrasts, I(Q), of the dried and rehydrated samples mapped the characteristic spatial arrangement of IgM in the reciprocal space Q [nm-1] (FIG. 5B-D, upper panel, large red open circles). For the reconstruction of the immobilized IgM structures from these curves we considered the IgM pentamer as mathematically self-similar and thus fractal (Horejs, Gollner, et al.; Horejs, Pum, et al.). The self-similarity of the IgM molecule at different length scales is based on its characteristic Y-like structure (FIG. 5, Y model).

We investigated the structural changes after embedding in the inventive solution (PU-IgMFas-NC), exposure to radiation (*PU-IgMFas), or embedding and subsequent exposure to radiation (*PU-IgMFas-NC) compared with the dried immobilized IgM molecules. The signals of the untreated immobilized PU-IgMFas were at the lower limit of resolution when compared to the background signal of PU alone. Thus, we calculated the relative changes of the form factors, ΔP(Q), of the dried PU-IgMFas (FIG. 5B, upper panel, red, gray, and black small open circles). The relative scattering contrast is negative. The greatest differences were found when untreated PU-IgMFas samples were compared with PU-IgMFas-NC (FIG. 5B, upper panel, small red open circles). The embedding decreased the scattering contrast for characteristic distances between $\zeta=3$ and $\zeta=15$ nm. These distances correspond to the average extension of the IgM molecule and provide evidence that the IgM molecules are entirely embedded.

When PU-IgMFas samples were compared with *PU-IgMFas (FIG. 5B, upper panel, small gray open circles), we again observed a significant decrease in scattering contrast, which was detectable between $\zeta=3$ and $\zeta=12$ nm. This result may principally reflect the fact that radiation causes a conformational change (Gianfreda and Scarfi; Kapoor and Priyadarsini; Stadtman and Levine; Zbikowska, Nowak and Wachowicz) or leads to a breakage of bonds within the protein and thus decreases electronic contrast. When we compared PU-IgMFas with *PU-IgMFas-NC, the relative difference in scattering contrast was lower compared with the differences observed between PU-IgMFas and *PU-IgMFas samples (FIG. 5B, upper panel, small black open circles).

According to the applied analytical model, we fitted the measured scattering profiles, leading to an average size of the IgG arm of κ=4.0-6.0 nm (FIG. 5B, dashed lines) for the dried immobilized IgM molecule. Additionally, based on the known three-dimensional structure of the IgG unit cell (Protein Data Bank: 2RCJ) (Perkins et al.) as the initial configuration, we were able to reconstruct the IgG subunits of the dried immobilized IgM molecules as depicted by the gray bead model in FIG. 5B. Further computational operations determined the spatial arrangements of the IgG subunits within the pentameric IgM molecules, particularly $\kappa_p$, a circular measure that spans two opposite IgG arms and subsequently their opening angles θ. The fractal dimensions D are related to the particular opening angles θ (FIG. 5) that comprise the five IgG arms. All dried systems have a common fractal dimension of D=3. We anticipated that all dried samples have a common IgM superstructure with θ=0.51° or θ=29.22° for the IgG arms. The anticipated IgM structural model of the dried samples *PU-IgMFas, PU-IgMFas-NC, and *PU-IgMFas-NC is given in FIG. 5B by the green bead model.

To reconstruct the entire SAXS signal, using a complementary approach, we determined the mean forces between the IgG arms. These are given at the bottom of FIG. 5B (small open connected circles). The high corrugation of the mean forces indicates a stabilized but collapsed protein structure. We related the high corrugation to the lack of a hydration shell in any of the dried samples.

After rehydration of the samples embedded in the inventive solution or non-embedded and reconstitution of the hydration shell, the scattering contrast for all samples was positive compared with the dried samples. In the case of the rehydrated PU-IgMFas, the fractal dimension decreased to D=2.5 whereas no measurable signals were obtained for *PU-IgMFas. This finding indicates that the IgM molecule without the inventive solution is destroyed by irradiation and that rehydration of PU-IgMFas results in a partially open IgM superstructure comprising an increased angle θ caused by re-imposing the hydration shell. The corrugation of the corresponding mean forces is decreased (bottom of FIG. 5C) suggesting that the IgG arms are less attracted to each other, which is consistent with the partially open configuration of the IgM superstructure.

Figure 6A:
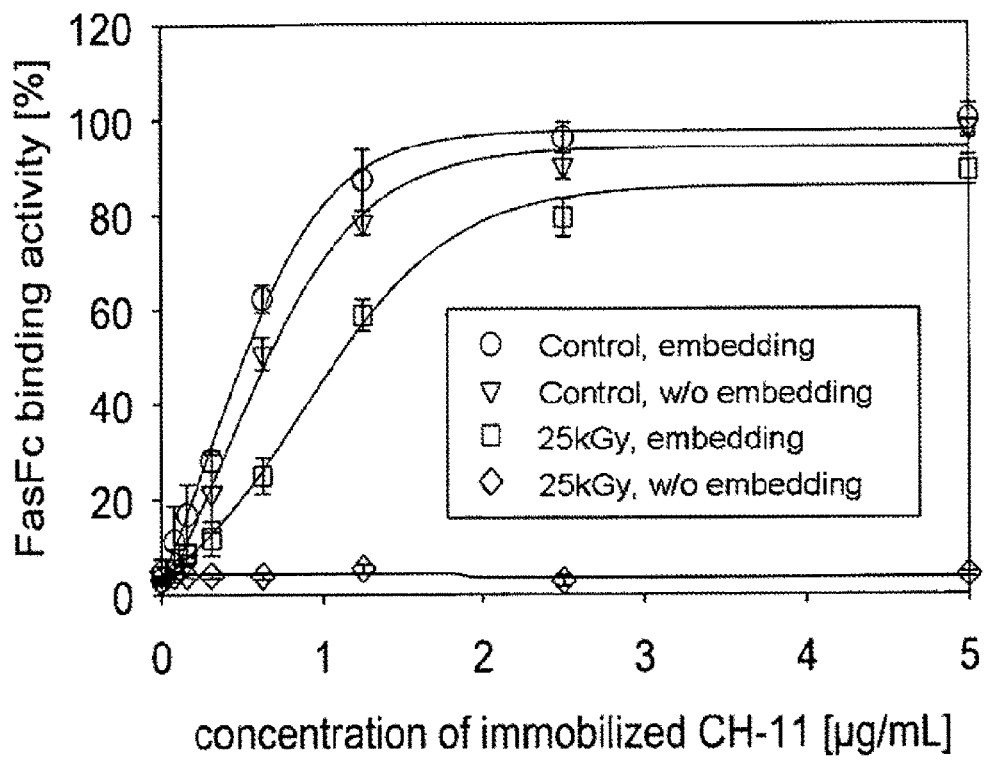
Figure 6B:
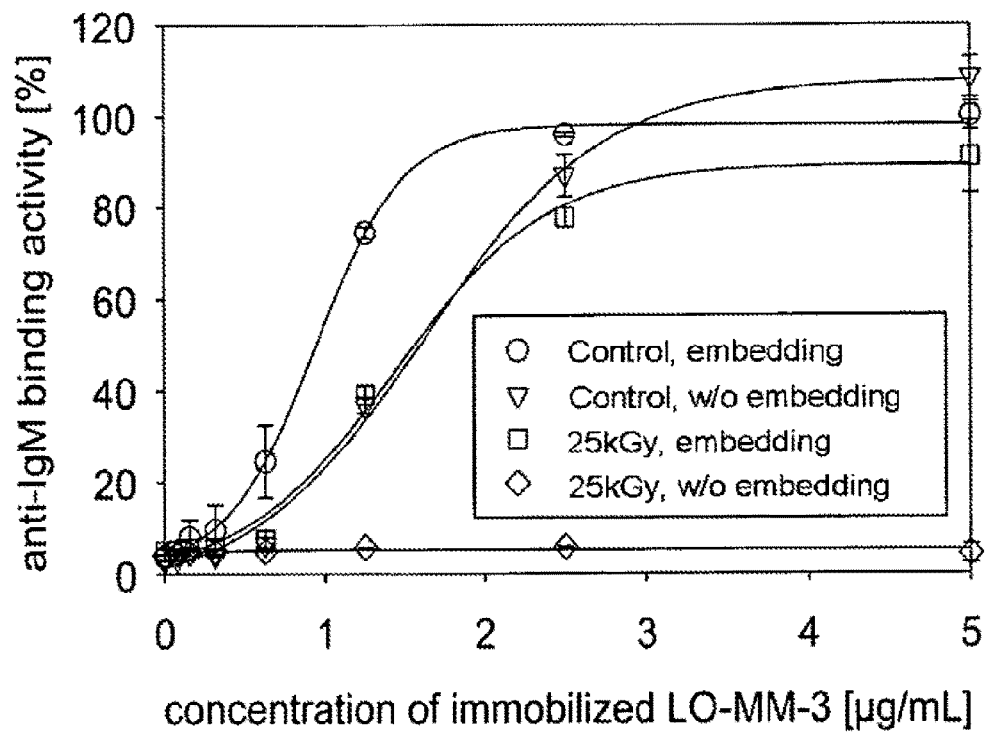
Figure 6C:
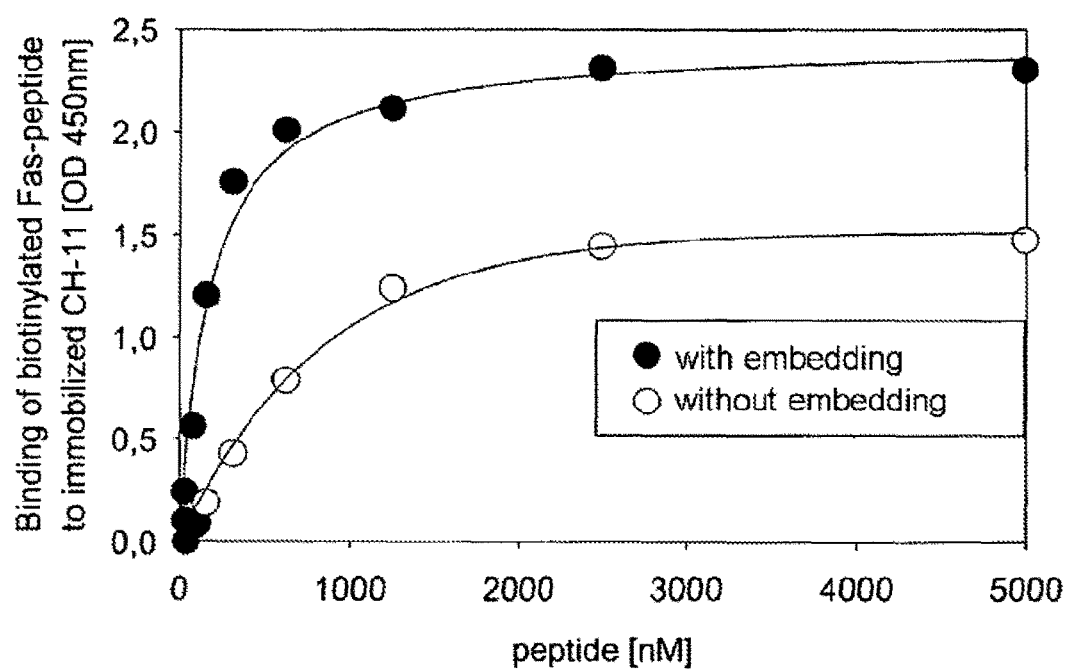

The opening of the IgM superstructure and thus refolding was even better when *PU-IgMFas-NC samples were rehydrated. A structural model for the IgG arms was calculated (gray bead model in FIG. 5D). As the fractal dimension decreased to D=1.5, the angle θ can be expected to increase. We anticipated that embedding favors rehydration of the protein. If we combine the structural model and the opening angle θ, then we can reconstruct a rather open structural model for the IgM molecule. This is given by the green bead model in FIG. 5D. Again, we calculated the mean forces and found that the corrugation is lower than in the other examples given in FIG. 5 (bottom).

These results show that after drying proteins are embedded in a shell formed by the inventive solution, and that the three-dimensional protein structure is maintained and refolding after reconstitution is improved.

Example 4: Functional Evaluation of Antigen Binding of Immobilized Anti-Fas IgM

Next, we investigated whether embedding in the inventive solution can preserve the functionality of $IgM_{Fas}$. Therefore, $IgM_{Fas}$ was immobilized on an ELISA plate and probed for binding of a highly specific recombinant human Fas antigen fragment (hFas::Fc) (Schneider et al.) with and without embedding in the inventive solution and/or β-irradiation.

As shown in FIG. 6A/B, hFas::Fc was recognized by $IgM_{Fas}$ in a concentration dependent manner. Without protection, β-irradiation at >25 kGy led to functional impairment of $IgM_{Fas}$, as demonstrated by complete loss of antigen binding capacity. By contrast, embedding in the inventive solution did not affect antigen binding of IgM$_{Fas}$, but protected IgM$_{Fas}$ from radiation-mediated damage over a broad range of concentrations. In order to investigate the functional integrity of the IgM$_{Fas}$ paratopes at the molecular level, we employed an N-terminally biotinylated epitope peptide (biotin-RCKPNFFCNSTVCEHCDP-NH2) which was identified by peptide array screening. IgM$_{Fas}$ was immobilized on an ELISA plate (with and without β-irradiation and/or embedding) and probed with graded amounts of epitope peptide, which was subsequently detected by a streptavidin-HRP conjugate in a colorimetric assay (FIG. 6C). For reference, the $K_D$ of IgM$_{Fas}$ for the epitope peptide without embedding and β-irradiation was determined to be 160±13 nM (data not shown). As shown in FIG. 6C, β-irradiation led to a drastically reduced affinity of IgM$_{Fas}$ for the epitope peptide ($K_D$=855±129 nM), demonstrating severe radiation-induced damage. By contrast, the integrity of the antibody paratopes was fully maintained when embedding was performed prior to β-irradiation, demonstrated by preservation of the $K_D$ of the IgM$_{Fas}$ for the epitope peptide (188±25 nM).

These results confirm that the inventive solution preserves the three-dimensional structure of proteins, such that their function is maintained even when exposed to stress conditions such as drying and irradiation.

Figure 7D:
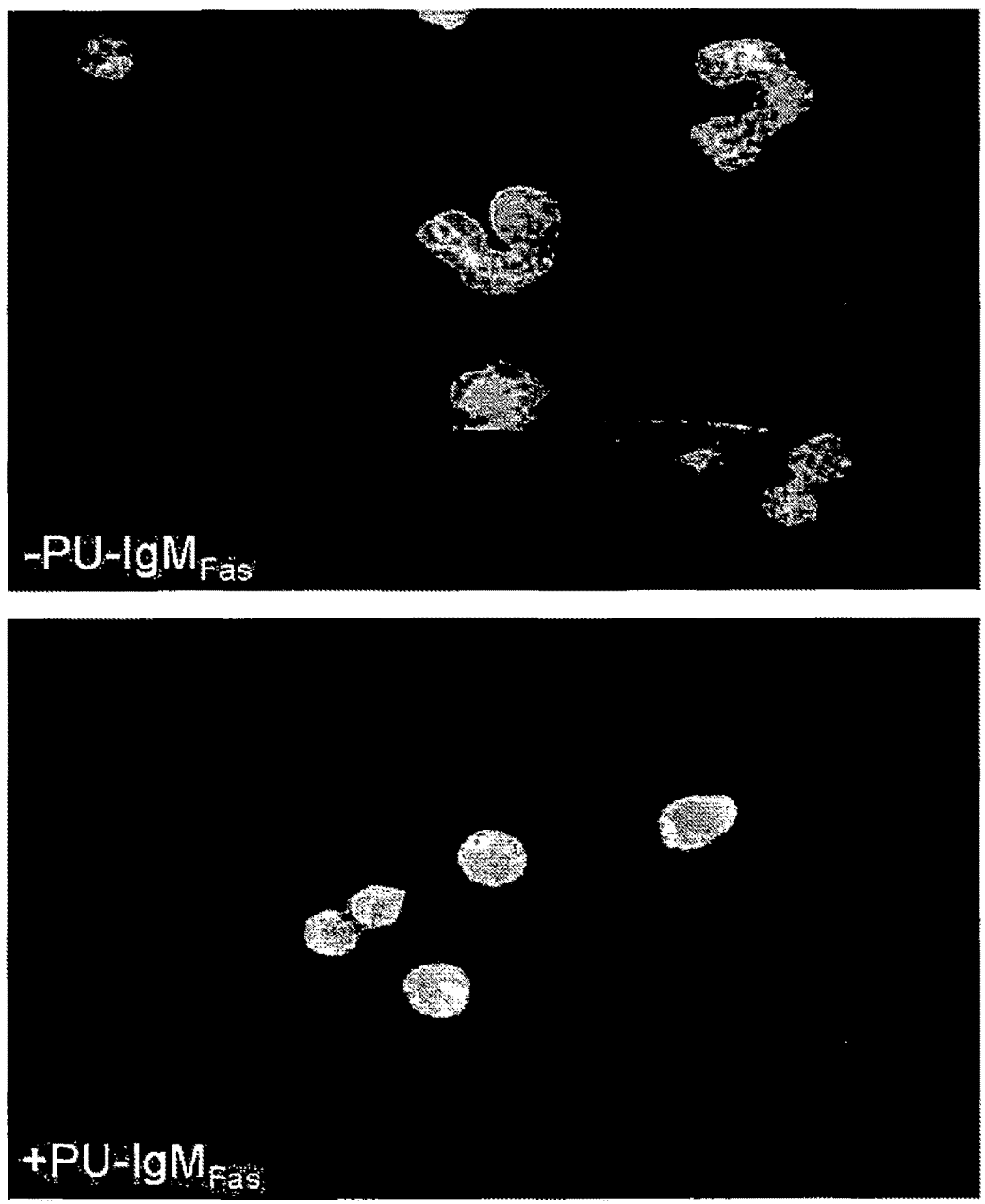
Figure 7E:
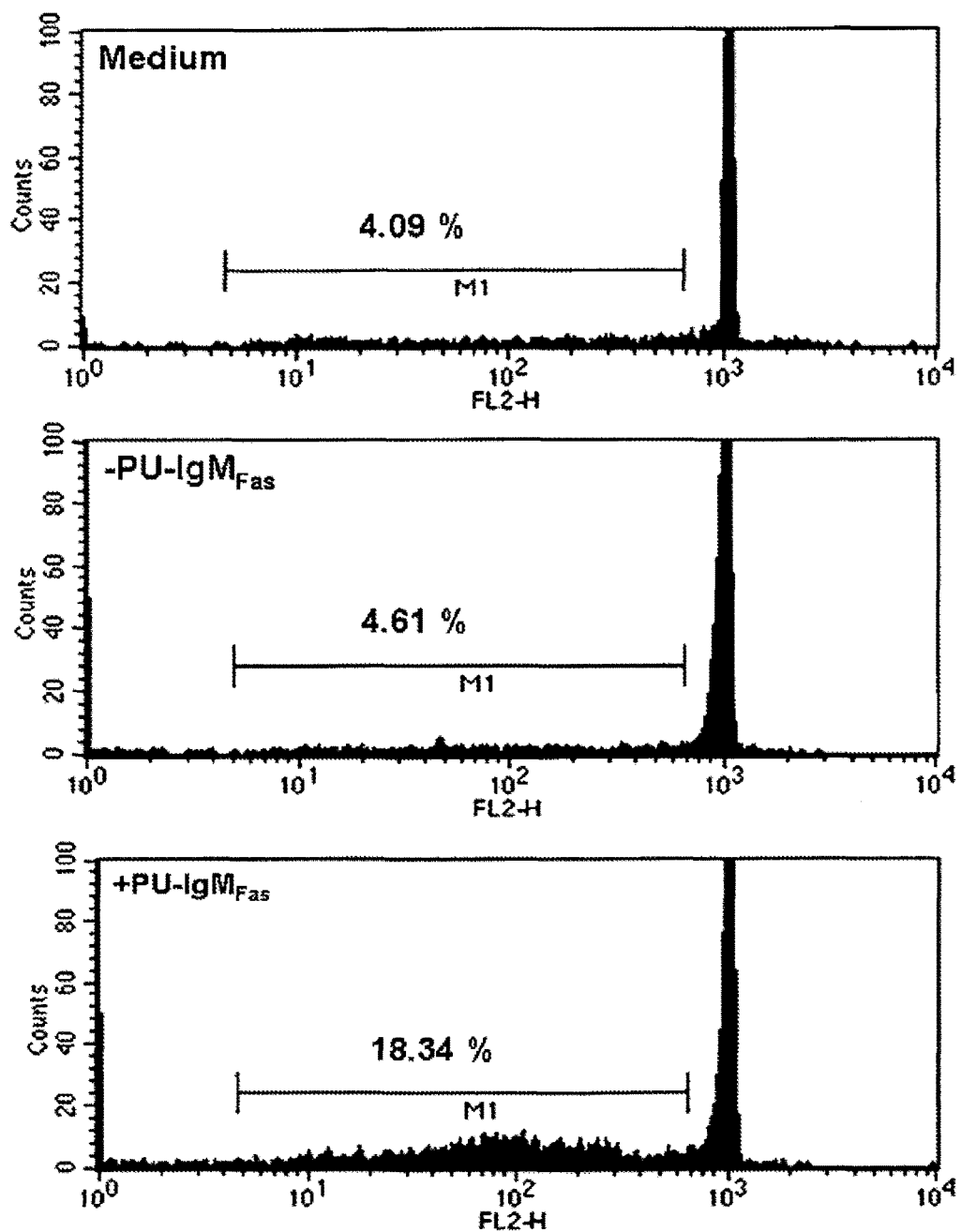

Example 5: Functional Evaluation of the Agonistic Biological Activity of PU-IgM$_{Fas}$-NC To further investigate the maintenance of biological activity, we studied the potential of PU-IgM$_{Fas}$-NC to induce apoptosis (Logters et al.; Paunel-Gorgulu, Logters, et al.; Paunel-Gorgulu, Zornig, et al.; Scholz et al.) and inactivate Fas-sensitive cells (Zamzami and Kroemer) in vitro. To prove that apoptosis induction by PU-IgM$_{Fas}$-NC is receptor-specific, we used Fas-positive and Fas-negative Jurkat T-cell lines as targets. As shown in FIG. 7C, apoptosis induction occurred exclusively in Fas-positive cells after incubation with PU-IgM$_{Fas}$-NC. Moreover, to confirm the potential therapeutic efficacy of PU-IgM$_{Fas}$-NC in a clinically relevant setting, we used highly activated Fas-expressing neutrophils obtained from severely injured trauma patients (Paunel-Gorgulu, Zornig, et al.) (Injury Severity Score>16) to confirm PU-IgM$_{Fas}$-NC-mediated apoptosis in patient neutrophils. Specifically, apoptosis-related condensation of the neutrophil nuclei (Zamzami and Kroemer) was found in PU-IgM$_{Fas}$-NC-treated cells but not in untreated cells as demonstrated by nucleic staining (FIG. 7D) and flow cytometry (FIG. 7E) after challenging these neutrophils ex vivo with PU-IgM$_{Fas}$-NC for 4 h.

These results provide further proof that the inventive solution preserves the three-dimensional structure of proteins, such that their function is maintained even when exposed to stress conditions such as drying and irradiation.

Example 6: Sterilization Reduces Contamination while Maintaining Functionality of Polypeptides To test whether the embedding of polypeptides in the inventive solution may undesirably protect bacteria or viruses, that might contaminate the polypeptide preparation, during a sterilization process, the bio-burden of functionalized and embedded polyurethane foams was determined. Six different lots of each >70 plastic housings containing PU-IgM$_{Fas}$-NC were manufactured for potential use for extracorporeal immune modulation. The bio-burden of 10 non-sterilized PU-IgM$_{Fas}$-NC samples from each lot was measured for reference. The mean bio-burden was 151±18 bacteria/fungi per module. Sterilization was performed by β-irradiation at ≥25 kGy, and validation of sterilization was performed according to the ISO 11137 VD$_{max}$ (Paunel-Gorgulu, Logters, et al.) method. All 60 PU-IgM$_{Fas}$-NC modules irradiated with the reference dose (8.5±0.8 kGy) were found to be sterile confirming the validity of the sterilization process with NC.

Additionally, virus inactivation studies were performed using human adenovirus type 5 (Ad5), which is a reference virus for testing the virucidal efficacy of chemical disinfectants (Kim et al.; Sauerbrei et al.). Specifically, 50 µL of virus suspension were dried at 37° C. on the bottom of sterile polystyrol tubes. The dried virus was then overlaid with 50 µL of the inventive solution and dried again at 37° C. After β-irradiation at 25 kGy or 40 kGy (controls were not irradiated), the virus/protective solution bilayer was resuspended in 1 mL of MEM, and the titer of infectious virus was determined by means of end-point titration (FIG. 8A/B). In parallel, the same experimental setup was employed with IgM (LO-MM-3; FIG. 8C/D).

As is shown in FIG. 8, β-irradiation led to quantitative inactivation of Ad5 (25 kGy, ≥99.9% reduction, 40 kGy≥99.999% reduction; FIG. 8A/B) while the functionality of an IgM antibody was maintained. These results demonstrate that the inventive solution selectively stabilizes and protects protein structures but does not prevent irradiation-induced impairment of virus replication. Therefore, embedding in the inventive solution does not constitute a risk for virus contamination during production processes.

Example 7: A Mechanistic Model of the Activity of the Inventive Solution

Figure 9C:
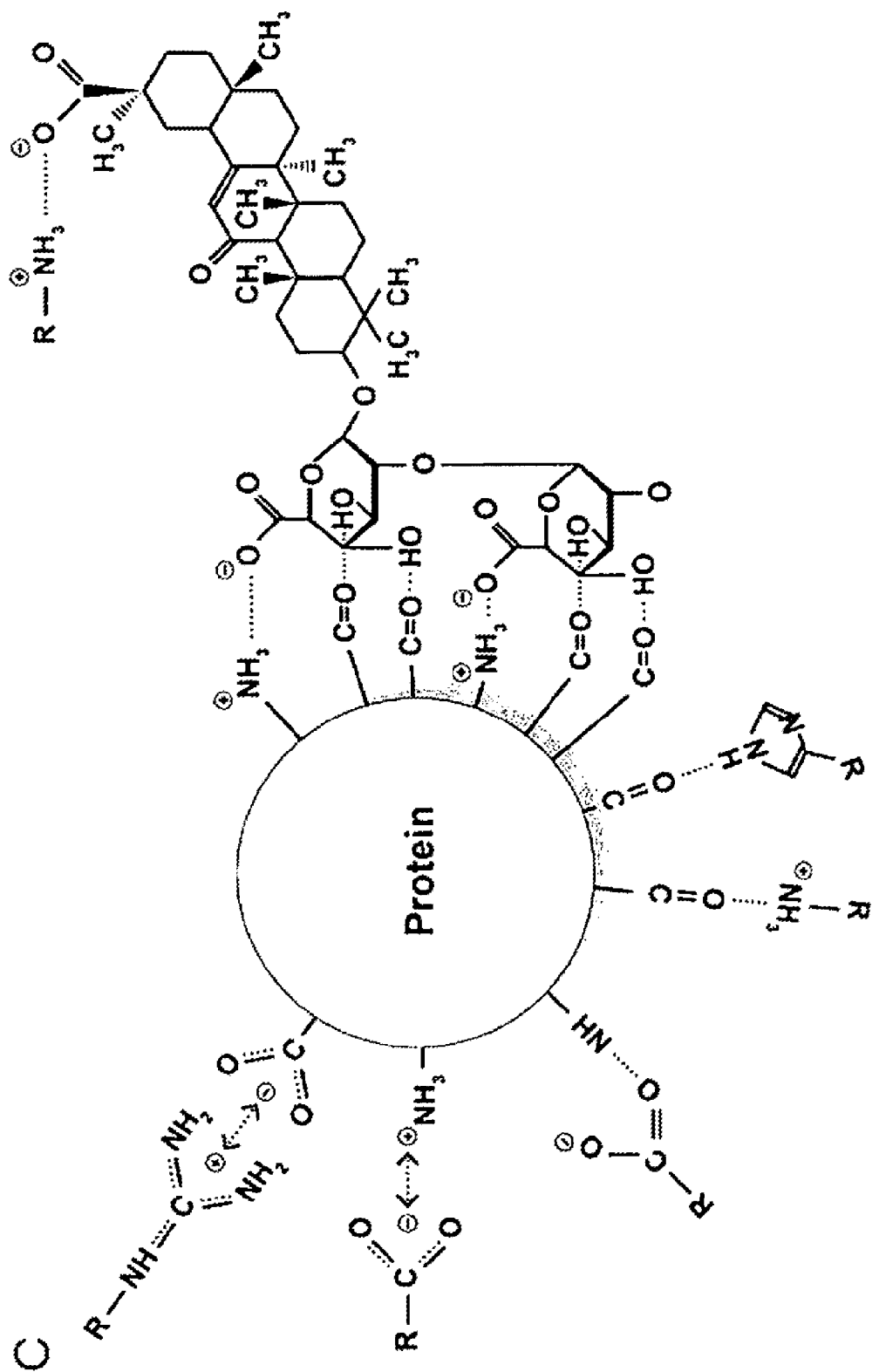

Without wishing to be bound by theory, the inventors of the present invention hypothesize that interactions between small molecules, such as amino acids (FIG. 9A), amino acids with glycyrrhizic acid (FIG. 9B), and amino acids/glycyrrhizic acid with protein structures (FIG. 9C) mediate the activity of the inventive solution as depicted schematically in FIG. 9. In this model, glycyrrhizic acid interacts with both the protein (via ionic interactions and hydrogen bonds) and small molecules (e. g., amino acids via three carboxyl groups of the glycosidic part and the aglycon). According to the preferential exclusion concept, glycyrrhizic acid together with uncharged molecules may support the osmolytic stabilization of the hydration shell around the protein in the presence of water by increasing the surface tension of the aqueous solutions. In this example, interactions between different amino acids, as well as between amino acids and glycyrrhizic acid, result in the strong amorphous character of the inventive solution. Moreover, during drying, the protein is interconnected with glycyrrhizic acid and with charged amino acids that replace the water molecules while interacting with the protein via hydrogen bonds according to the concept of preferential binding (FIG. 9C). The amorphous character in combination with the antioxidant, radical scavenging, and metal chelating features of particular components may support the protective effects of the shell around the protein.

Example 8: Stabilization of Proteins During Spray Drying

To confirm the usefulness of the inventive solution for the stabilization of proteins during spray drying, Ovalbumin (OVA) was employed as a model protein and was spray dried with the inventive solution. The dried powder was then characterized for integrity using Circular dichroism (CD), Sodium dodecyl sulphate polyacrylamide gel electrophoresis (SDS-PAGE) and fluorescence spectroscopy.

Materials and Methods

Ovalbumin was purchased from Sigma (St. Louis, Mo., USA). The inventive solution was as described above (see embedding solution). 1-Anilino-8-naphthalene sulfonate (ANS) was also purchased from Sigma (St. Louis, Mo., USA). All other reagents were of analytical grades.

Preparation of Spray-Dried Protein

3% (w/v) of Ovalbumin along with 6% (w/v) of the inventive solution were spray dried using a Büchi B-290 laboratory spray dryer (Büchi, Flawil, Switzerland). Inlet air temperature was set to 120° C., the air flow was 470 L/h, the pump rate was 7.5 ml/min and the outlet air temperature was between 50-55° C.

SDS-PAGE

SDS-PAGE was carried out using a Bio-Red Mini-Protean 3 gel electrophoresis system (Bio-Red Laboratories, Hercules, USA). 10 μl of protein samples (0.5 mg/ml) was loaded into each well after incubating (95° C., 5 min) with 10 μl of sample buffer and subjected to electrophoresis at voltage of 200 V for about 55 min. The protein was visualised with Coomassie blue staining.

Circular Dichroism (CD)

Jasco J-715 spectropolarimeter (JASCO International Co. Ltd, Hachioji city, Japan) was used to assess the secondary structure of proteins before and after spray drying. CD spectra were recorded in far UV range (200 to 250 nm) region with a sampling interval of 1.0 nm in a 0.05 cm path length cuvette. The solution of the invention was separated from the protein using an ultra-filtration device (Vivaspin 6 from Sartorius Stedim biotech, Göttingen, Germany) since it has some signal in CD. All spectra are average of two scans and were background corrected and normalised. Spectra were then compared to that of pure/unprocessed protein.

Fluorescence Spectroscopy

The fluorescence spectra were recorded in a fluorescence spectrometer (LS55 from PerkinElmer, Waltham, USA) using a 1 cm path length cuvette. Intrinsic fluorescence of ANS was measured by exciting it at 360 nm and the emission spectrum was recorded in 390-550 nm range. Fluorescence spectra were corrected for the background spectrum of solvent.

Results

Figure 10A:
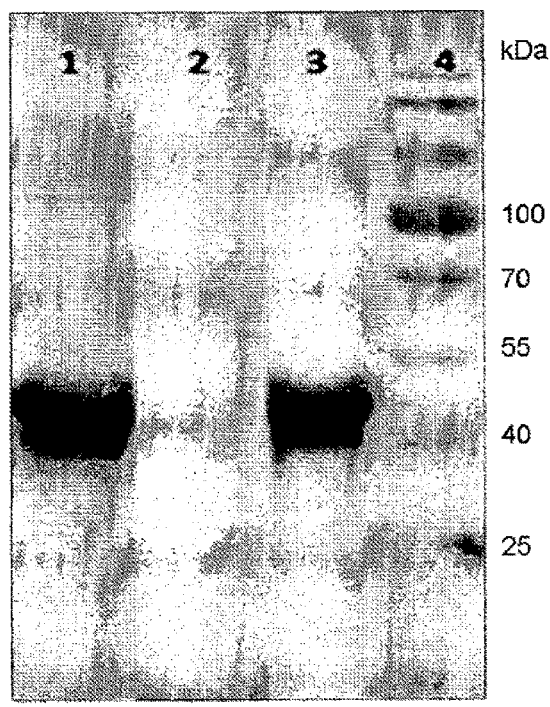

SDS-PAGE analysis of OVA control and spray dried OVA with the inventive solution is shown in FIG. 10(A). The same gel pattern is observed in both samples and no low molecular weight bands are present, indicating that no degradation of the OVA molecule has taken place upon spray drying.

Figure 10B:
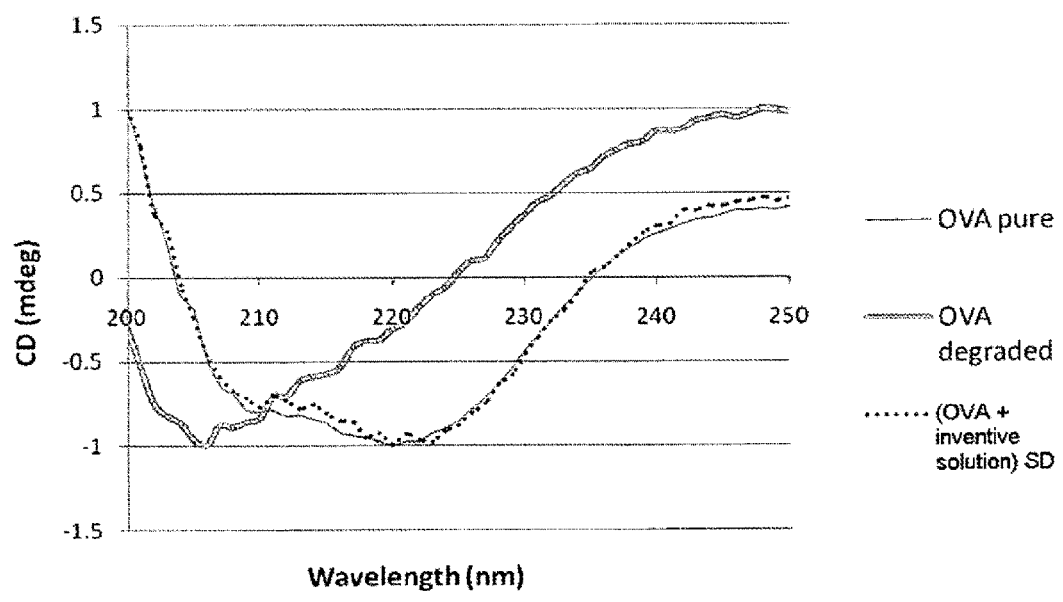

In addition, as shown in FIG. 10(B), the CD spectra of OVA after spray drying with the inventive solution resembles the OVA control indicating that no change in secondary structure can be observed after re-dispersion.

Figure 11:
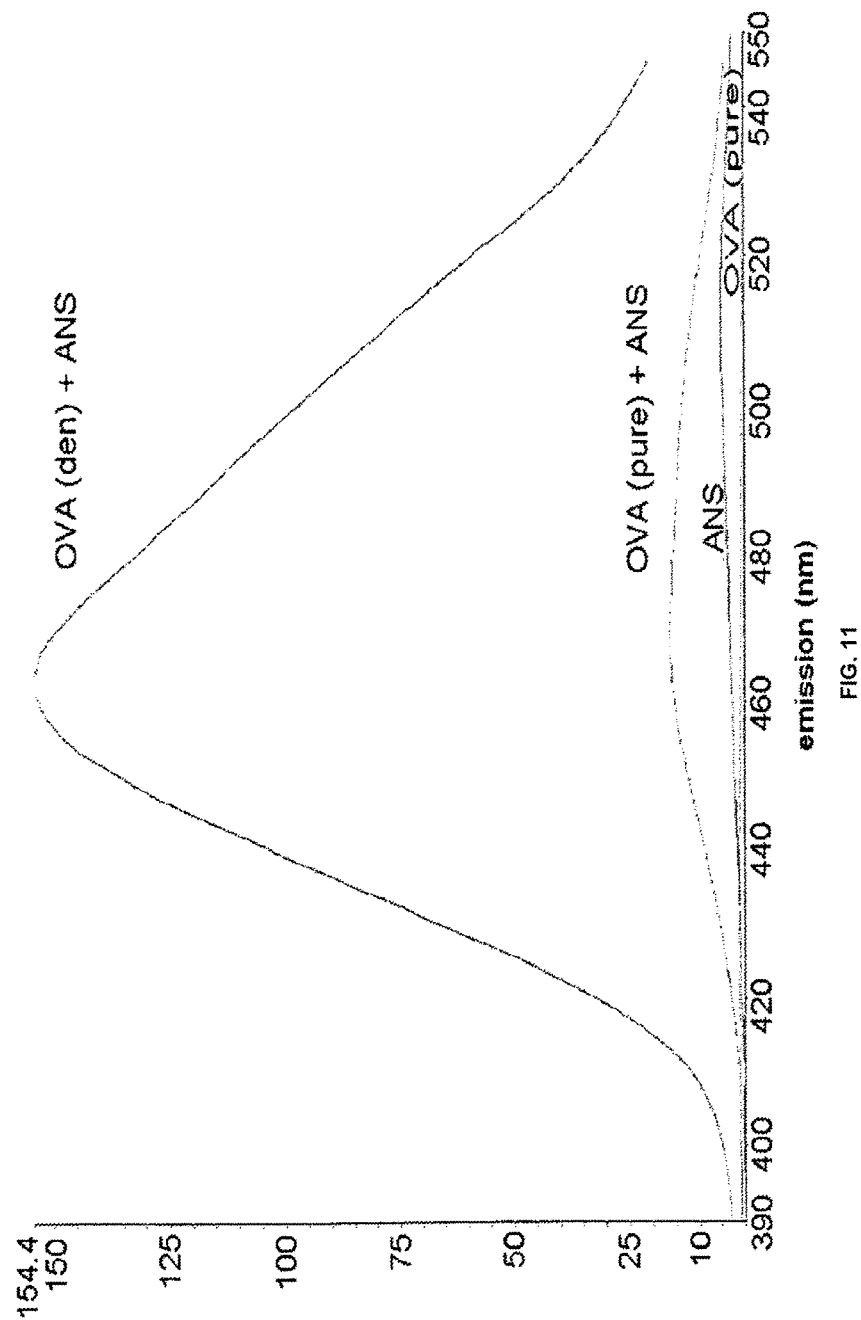
Figure 12:
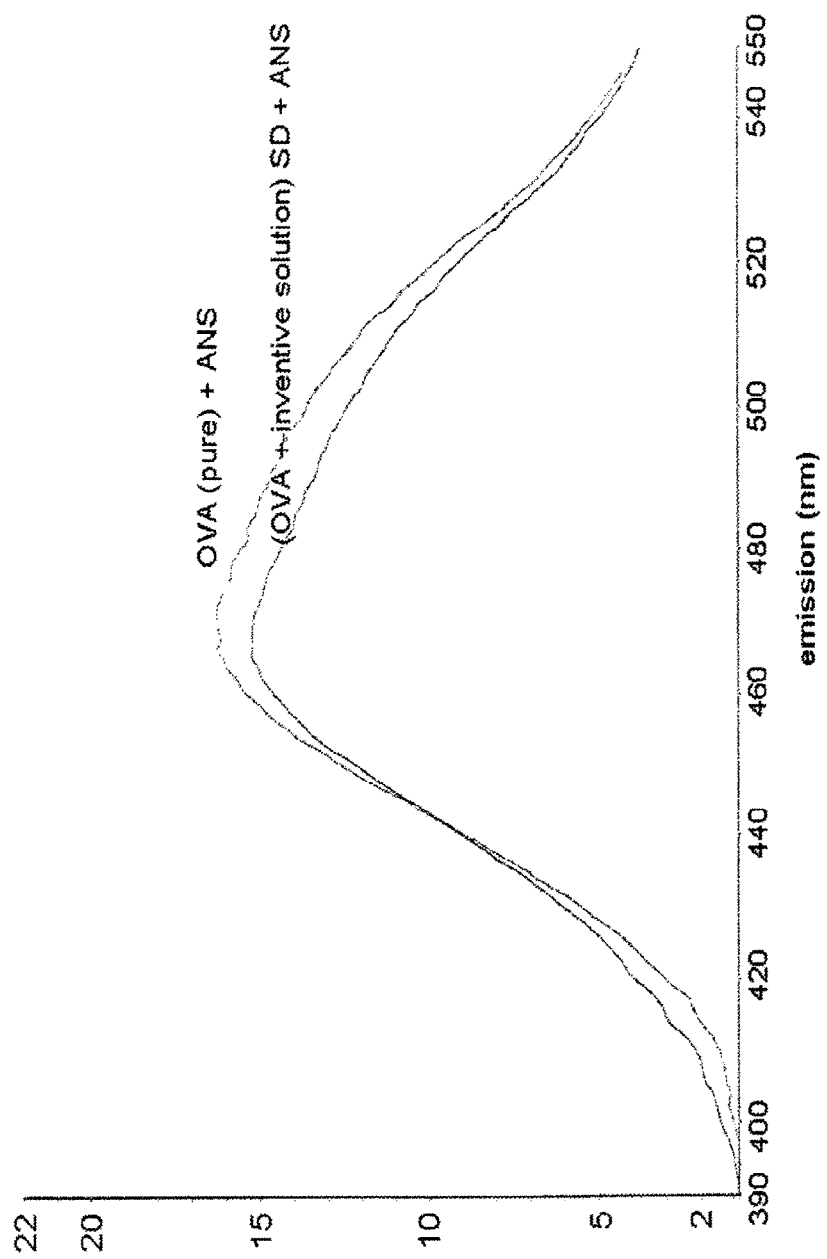

1-Anilino-8-naphthalene sulfonate (ANS) is practically non-fluorescent in water, but shows fluorescence upon binding to hydrophobic sites that exists on proteins. Accordingly, this fluorescence is greatly increased when the protein is denatured and thus serves as a measure of the degree of denaturation (FIG. 11). This phenomenon was used to characterise the integrity of OVA after spray drying. As seen in FIG. 12, the control and spray dried OVA with the inventive solution possess the same fluorescence intensity indicating that no denaturation event had taken place during spray drying.

In conclusion, the inventive solution is suitable for preserving the protein structure during spray drying of Ovalbumin as confirmed by a set of different techniques.

Example 9: Stabilization of Proteins after Lyophilization and Storage for Six Weeks at 40° C.

To determine the influence of the stabilizing and protecting solution (SPS) of the present invention on a therapeutic anti-TNF-α antibody, protein microarrays were applied as an easy and fast tool. UNIchip® high-density protein microarrays are designed for the quantitative analysis of antibody binding profiles and characteristics (Feyen et al. 2008; Lueking et al. 2008; Lueking et al. 2005). The UNIchip® microarray contains 384 pre-defined and His-tag purified recombinant human proteins on a nitrocellulose-coated glass slide. Sets of membrane proteins, intracellular and extracellular proteins are available. The screening of antibody binding profiles is, for example, an important tool to characterize the specificity of therapeutic antibodies, to avoid side effects due to antibody cross-reactivity, or to detect autoimmune antibodies in patient blood.

9.1 Materials and Methods

UNIchip® Protein Microarrays

Protein microarrays were manufactured by Protagen on nitrocellulose-coated slides (UNIchip® AV-400 Premium, Lot 0421104; Protagen, Dortmund, Germany). Each microarray was printed with a set of 384 different recombinant human proteins, representing different gene ontology classes. Additionally, 19 human serum proteins and 10 control proteins are included in the content of the UNIchip® AV-400 microarray. The proteins originate from an *E. coli* protein expression library and were purified using a His-tag as published earlier (Feyen et al. 2008). Each recombinant human protein was printed in quadruplicates on the biochip at an average amount of 20 fmol/spot. In addition, IgG from different species commonly used as hosts for antibody generation were printed in different concentrations as process controls for immunodetection by secondary antibodies. The protein biochip was also printed with a serial dilution of native TNF-α (Sigma, St Louis, Mo.) in the following concentrations: 10, 8, 6, 4, 2, 1, 0.5, 0.2, 0.1, 0.05, 0.025, 0.01, 0.001, 0.0005, 0.0001 pmol/μl. This corresponds to 20, 16, 12, 8, 4, 2, 1, 0.4, 0.2, 0.1, 0.05, 0.02, 0.01, 0.002 fmol of TNF-α per spot, respectively.

Incubation Conditions on UNIchip® AV-400.

A therapeutic anti-TNF-α antibody, was incubated on two protein biochips for every experiment unless indicated otherwise. The optimum working concentration of 2.5 mg/ml was used as previously determined (Feyen et al. 2008).

The protein microarrays were blocked in 2% (w/v) bovine serum albumin (BSA/TBST, 0.1% [v/v] Tween 20) at room temperature for 1 h. The antibody was added to 2% (w/v) BSA/TBST and was incubated in a humidified atmosphere for 16 h. Following three TBST washes and subsequent incubation with the secondary antibody (goat-anti-human-IgG-Cy3 (Dianova, Hamburg, Germany) at 0.002 mg/ml for 1 h at room temperature in 2% (w/v) BSA/TBST, the protein microarrays were washed three times in TBST. All antibody incubation steps were carried out in a volume of 200 μl in an automated hybridization station (Tecan HS 4800 Pro; Tecan, Crailsheim, Germany). Read out of the results was performed with a confocal microarray reader (ScanArray 4000, Perkin Elmer Life Science; San Jose, Calif.) using identical settings for all protein microarrays.

Sample Preparation

The following samples were produced:
a) 5 mg of the therapeutic anti-TNF-α antibody, re-buffered with the SPS-solution of the present invention (mixture of seven amino acids; Arg, Ala, Gly, Lys, Glu, His, Trp at pH 5.2-7.5);
b) 5 mg of the therapeutic anti-TNF-α antibody, re-buffered without SPS.

Each preparation was aliquoted into vials at 1.25 mg and lyophilized. Samples were stressed by increased temperature and time. After reconstitution samples were analyzed by UNIchip® AV-400. As a control, the therapeutic anti-TNF-α antibody was reconstituted following the manufacturer's instruction and stressed by increased temperature (40° C.) and time (six weeks; $t_6$) in the resolved state.

Buffers

The buffers were prepared according to standard protocols. TBS buffer: 10 mM Tris-HCl, pH 7.5 (Merck, Darmstadt, Germany), 150 mM NaCl (Diagonal, Minster, Germany). Blocking Buffer: 10 mM Tris-HCl, pH 7.5 (Merck), 150 mM NaCl (Diagonal), 2% BSA (Sigma). TBS-T Buffer: 20 mM Tris-HCl, pH 7.5 (Merck), 0.5 M NaCl (Diagonal), 0.1% (v/v) Tween 20 (Sigma).

Image and Data Analysis.

Image analysis was performed using the software package GenePix Pro 6.0 (Molecular Devices, Ismaning, Germany).

The mean intensity was determined for each protein spot after background subtraction. For background subtraction the median background fluorescence intensity was used.

For reporting the off-target activity (OTA) the median intensity of the four protein spots (quadruplicates) of each protein was determined.

Based on all experiments for one antibody, the average of the median intensities of each protein or protein concentration was normalized using the corresponding IgG process control (e.g. fluorescence intensity derived from binding of secondary antibody to host IgG protein spots). The following calculation was used for normalization: signal antigen/mean signal of IgG process control×100=X units.

For determination of binding to printed serial antigen dilutions, the Mean+/−SD of the four protein spots (quadruplicates) of each concentration tested was used. For the determination of statistical significance between data groups, the student's t Test was used. Differences between data groups were considered statistically significant when p was <0.05.

9.2 Quantification of Decreased Antibody Function

Figure 13A:
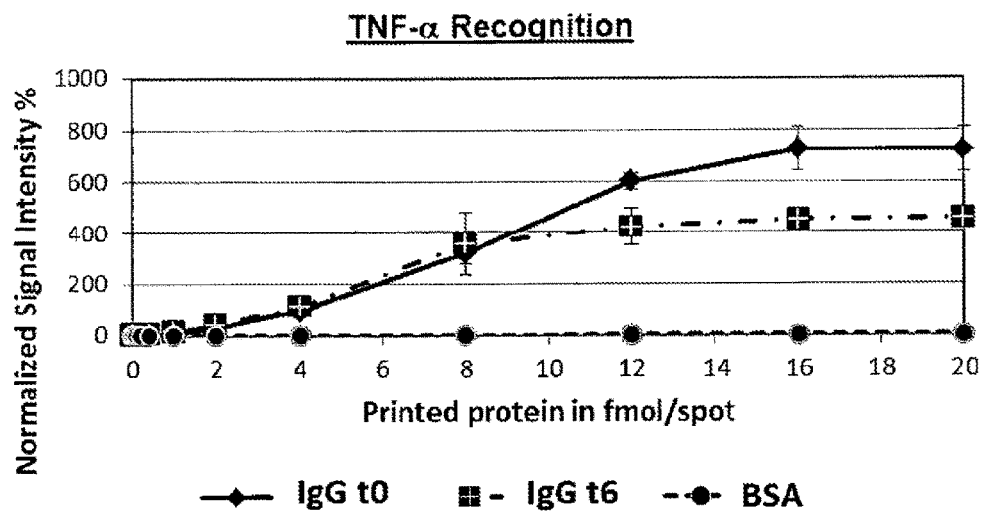
Figure 13B:
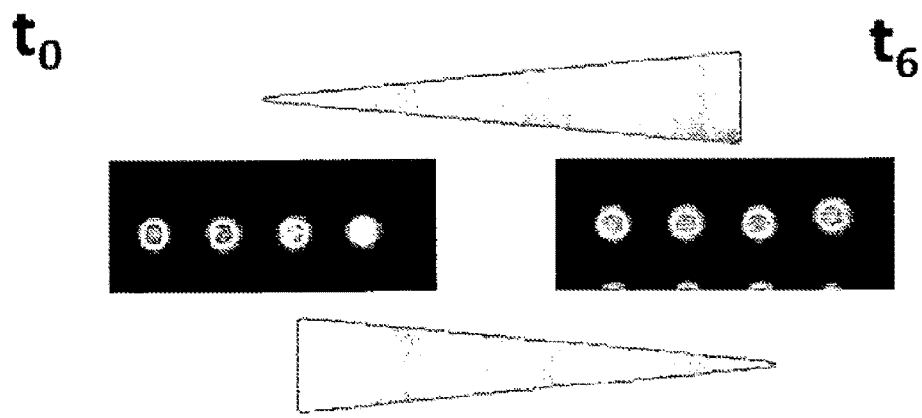

In order to determine the optimum antigen (TNF-α) concentration to be spotted on the microchip, different amounts of target antigens (range, 0-20 fmol/spot) were printed. For the binding studies, the therapeutic anti-TNF-α antibody was added to the microchip at a concentration of 2.5 mg/ml either freshly reconstituted (to) or after six weeks storage ($t_6$). The binding affinity as shown by fluorescence signal intensity was measured overtime (FIG. 13). As depicted in FIG. 13A, the functional loss of the therapeutic anti-TNF-α antibody after six weeks storage at 40° C. was observed with antigen concentrations of 12, 16, and 20 fmol/spot (p<0.05) but not with antibody concentrations in the range between 0-8 fmol/spot. For example, when 20 fmol/spot were used, normalized signal intensity units at time point to were in the range of 700-800 whereas after six weeks a decrease in signal intensity (450 units) was found. The loss of fluorescence intensity overtime is depicted qualitatively in FIG. 13B.

These results indicate that the concentration of 20 fmol antigen/spot is suitable for further experiments and that the range of signal intensity in which the loss of antibody function can be monitored is sufficient for the testing of stabilizing formulations. Therefore, in the following experiments, the antigen concentration of 20 fmol/spot and 2.5 mg/ml the therapeutic anti-TNF-α antibody were used as a standard.

9.3 Preservation of Antibody Binding Intensity by SPS

Figure 14:
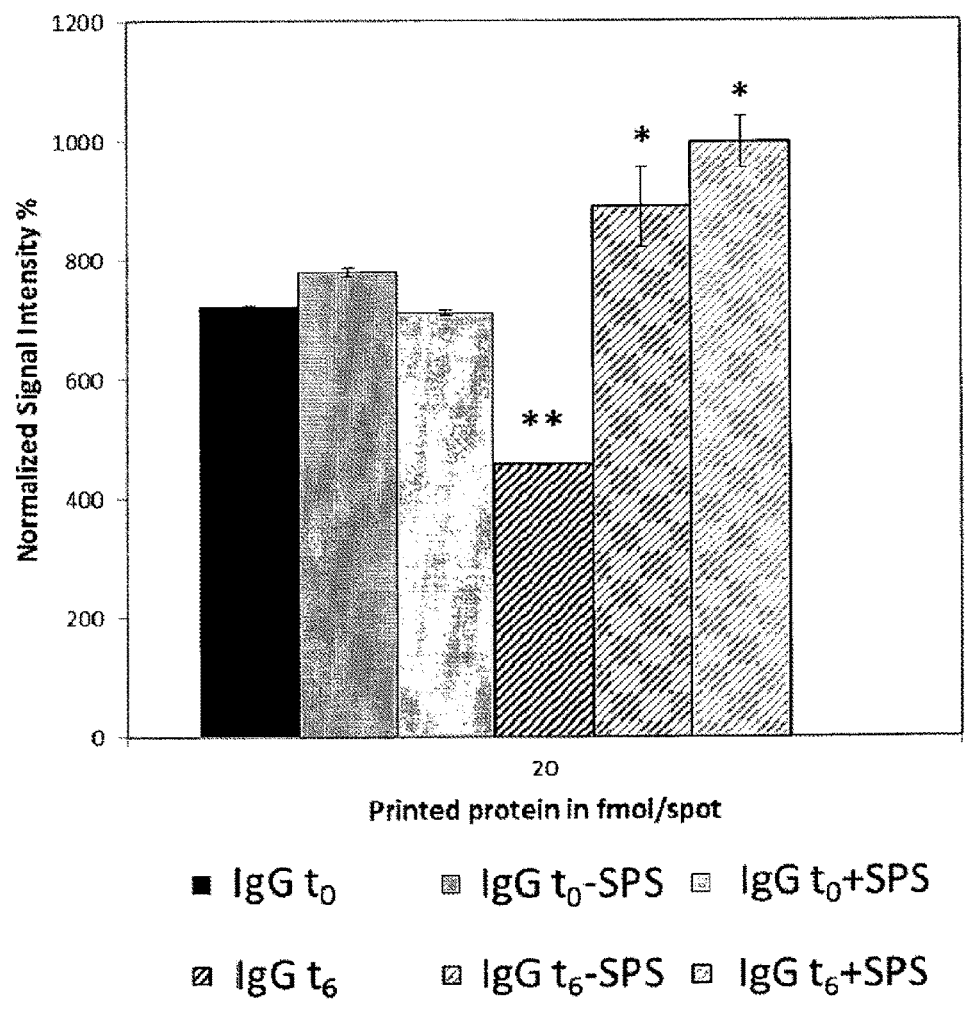

To evaluate the efficacy of the inventive solution (SPS) in stabilizing the antibody, the therapeutic anti-TNF-α antibody was re-buffered in SPS or in the buffer as recommended by the manufacturer and lyophilized. After lyophilization, samples were stored at increased temperatures and were reconstituted in water at the indicated time points and used in the microarray study at day 0 ($t_0$) and after six weeks storage at 40° C. ($t_6$). The functional activity of both formulations was compared with the freshly reconstituted antibody that was reconstituted at to and stored as a fluid formulation in the original buffer of the manufacturer (control). Immediately after reconstitution at to and $t_6$ the preparations of the lyophilized samples without SPS reacted with higher signal intensity up to 779/889 (normalized signal intensity; 108/123% of control). The $t_6$ preparation of reconstituted antibody (which was not lyophilized) showed decreased signal intensity (456 units; 63%). In contrast, the formulation with SPS resulted in further increased signal intensity at time point $t_6$ (138%), as shown in FIG. 14.

These results confirm the stabilizing effects of SPS that preserves the antibody binding strength to the specific antigen.

9.4 Binding Specificity—Number of Off Target Activities (OTAs)

To study whether SPS-formulated the therapeutic anti-TNF-α antibody exhibits unspecific binding profiles, the affinity to irrelevant proteins was quantified by counting the numbers of OTAs.

The comparison of the originally re-buffered the therapeutic anti-TNF-α antibody (control) and the sample that was re-buffered without SPS and subsequently lyophilized indicates that the lyophilization step resulted in a significant number of high OTAs (Table 1). However, the number of OTAs in the SPS-formulated sample was reduced at both time points, $t_0$ and $t_6$ (36 and 150 OTAs, respectively) compared with the formulation according to the manufacturer's recommendation (212 OTAs at to; 286 OTAs at $t_6$).

Therefore, the SPS-mediated preservation of binding strength as shown above is largely antigen specific and not a result of unspecific binding, represented by OTA.

TABLE 1

Number of OTAs detected over time in three different formulations

| Antibody Preparation | No. of OTAs $t_0$ | No. of OTAs $t_6$ | Ø OTA (Signal intensity) $t_0$ | Ø OTA (Signal intensity) $t_6$ |
|---|---|---|---|---|
| anti-TNF-α antibody + SPS | 36 | 150 | 23 | 45 |
| anti-TNF-α antibody − SPS | 94 | 135 | 41 | 83 |
| anti-TNF-α antibody resolved | 212 | 286 | 6 | 10 |

OTA: off target activity;
SPS: stabilizing and protecting solution;
$t_0$: start of experiment;
$t_6$: six weeks after start of the experiment 9.5 Determination of OTA Signal Intensity Values In addition to the evaluation of OTA numbers, the unspecific binding intensity, as an important aspect in characterizing the antibody binding profile, was quantified (see FIG. 15 for an overview).

The off-target-activities (OTAs) were normalized to a process control (human IgG; 250 μg/ml). The therapeutic anti-TNF-α antibody preparation which was directly resolved (control) showed up to 212 OTAs at time point to with very low mean OTA signal intensity values of 6% (Table 1). A significance threshold of 20% was arbitrarily defined by taking the mean OTA value of the control plus two-times the standard deviation of this mean. In detail, only 14 OTAs were higher than the significance threshold, indicating that most of the OTAs were considered as not significant. At time point T6 the number of OTAs was increasing up to 286 with a small increase to an average OTA value of 10%. The SPS-formulated antibody revealed only 36 OTAs at $t_0$. However, the mean signal intensity was 23% and therefore slightly higher than obtained by the control. Moreover, 15 OTAs were higher than a signal intensity value of 20% including OTAs with higher values in the range of ~50%. Under stressing conditions the number of OTAs was increasing to 150 OTAs including 76 OTAs with signal intensity values higher than 20% (not shown). Overall, this resulted in a mean signal intensity value of 45% (Table 1).

The antibody preparation which was reconstituted without SPS following lyophilization showed up to 94 OTAs at T0. The mean signal intensity value obtained was 41%. More specifically, 51 OTAs had signal intensity values>50%. Under stressing conditions the number of OTAs was increasing up to 135 OTAs accompanied by a mean signal intensity value of 83%.

Overall, these results indicate that the SPS formulation resulted in less OTA of the therapeutic anti-TNF-α antibody.

Accordingly, this example shows the improved antibody recognition of the respective cognate antigen TNF-α under protection by the SPS technology. Lyophilization on one hand improved the binding activity to the specific antigen and, on the other hand, significantly increased the OTAs after lyophilization, whereas the antibodies formulated with SPS resulted in less OTAs compared with the formulated antibodies according to the manufacturer's recommendation.

These results show that reconstituted SPS-formulated and lyophilized the therapeutic anti-TNF-α antibodyelicits significantly less Off-Target-Activity (OTA) after reconstitution and preserves binding strength even after six weeks storage at 40° C. compared with the therapeutic anti-TNF-α antibody that underwent the same treatment with the original formulation. In conclusion, it was possible to confirm the protein stabilizing effects of SPS as shown by preserved antibody functionality.

Example 10: Stabilizing Effects of the SPS on an Irradiated IgG1 Antibody

By using a therapeutic anti ErbB2 humanized IgG1 antibody as a model antibody, the efficacy of the Stabilizing and Protecting Solution (SPS) of the invention to prevent irradiation-mediated protein damage was studied.

10.1 Materials and Methods
ELISA.

An ELISA assay using immobilized, recombinant ErbB2 antigen (Sino Biological Inc., Beijing, China) was established and validated to quantify the antigen specific binding of soluble anti ErbB2 antibody antibody (Roche Pharma A G, Grenzach-Wyhlen, Germany). After coupling of ErbB2 antigen to the microtiter plates, free protein binding sites were blocked by using a blocking buffer containing FCS and Tween 20 (Sigma-Aldrich, Munich, Germany). Subsequently to the addition of anti ErbB2 antibody, plates were washed and alkaline phosphatase conjugated secondary antibodies (Dianova, Hamburg, Germany) were added. Specific binding of anti ErbB2 antibody to ErbB2 was detected photometrically by enzymatic conversion of the alkaline phosphatase substrate p-nitrophenylphosphat at 405 nm. The time and concentration dependent color reaction allows the quantification of functional anti ErbB2 antibody.

The ELISA exhibits a linear dose response curve at 405 nm for a anti ErbB2 antibody concentration range between 5 and 50 ng/mL. Linear regression was applied to fit a linear equation to the data points. The commercially available anti ErbB2 antibody formulation served as positive control during irradiation experiments.

All experiments to monitor the functionality of anti ErbB2 antibody following lyophilization and irradiation were performed with reconstituted Herceptin (20 ng/mL).

Fourier-Transform Infrared Spectroscopy FT-IR

The secondary structure of the anti ErbB2 antibody was analyzed using a FT-IR spectrometer Equinox 55 (Bruker Optics GmbH, Ettlingen, Germany) equipped with a mercury-cadmium-telluride (MCT) detector, a diamond-ATR-unit DuraSampl/RII™ (SensIR) and OPUS 65 software (Bruker Optics). For each spectrum, an accumulation of 240 scans was collected at a resolution of 4 cm$^{-1}$ from 4000 to 400 cm$^{-1}$. Reference spectra were recorded with the corresponding buffer and excipient solutions prior to each experiment to correct for background effects. Second derivative spectra were calculated with OPUS-65 software and the final protein spectra were smoothed with a 13-point function.

Electrophoresis

Non-reducing SDS-PAGE was used to monitor the aggregation and fragmentation of the antibody formulations. Analysis was performed using a Novex XCell II Mini cell system and Novex NuPAGE Bis-Tris Gels (4-12%); 10 wells at 1 mm thickness (Invitrogen, Darmstadt, Germany) with NuPAGE MOPS running buffer. Reconstituted lyophilizates were diluted to a final concentration of 0.4 mg/mL in LDS-sample buffer (Invitrogen). The samples were denatured at 95° C. for 10 min and then 10 μL of the samples were loaded to the gel wells. The applied protein amount was 4 μg/well. Separation was done at a constant voltage of 200 V and running time was approximately 90 min.

Gels were stained with Coomassie Brilliant Blue R250 staining and destaining solution (BioRad, Hercules, Calif., USA). A molecular weight standard was analyzed on each gel to determine the molecular weight of the detected bands (Novex Sharp Pre-Stained Standard, Invitrogen).

ProteoStat® Protein Aggregation Assay

The microplate aggregation assay (ProteoStat®; Enzo Life Sciences, Farmingdale, N.Y., USA) was carried out according to the manufacturer's recommendations. Briefly, samples were prepared for the aggregation assay at ambient temperature in the assay buffer. ProteoStat® positive control (aggregated lysozyme) and negative control (native lysozyme) for monitoring and detection of protein aggregation were supplied as lyophilized powders (300 μg each) and were reconstituted in 500 μl deionized water to generate 40 μM stock solution that may be stored at 4° C. for several weeks. The solutions were applied following 1:2 dilution (20 μM) in assay buffer. The reconstituted anti ErbB2 antibody samples (20 mg/mL) were diluted in assay buffer to a concentration of 4.5 mg/mL. As a control fresh reconstituted anti ErbB2 antibody (20 mg/mL) was diluted to 4.5 mg/mL. A clear bottom 96-well microplate (μClear black; Greiner, Frickenhausen, Germany) was prepared with 98 μL of these protein solutions. 2 μL of the freshly prepared ProteoStat® detection reagent loading solution were dispensed into each well. The microplates containing test samples were incubated in the dark for 15 min at room temperature. Fluorescence was quantified by a Fusion fluorescence micro plate reader (excitation: 550 nm; emission: 603 nm; PerkinElmer, Mass., USA).

Size Exclusion Chromatography (SEC)

Protein aggregation and degradation were quantified by SE-HPLC. Analytics were performed on HPLC system equipped with a UV-280 nm detector (Malvern Instruments, Worcestershire, UK) and a TSK-gel G3000SWXL 7.8×300 nm column (Tosoh Bioscience, Tokyo, Japan) at 30° C. and with a flow rate of 0.5 mL/min. The injection volume was 50-100 µL. The running buffer for SE-HPLC was Dulbecco's PBS pH 7.1 (PAA Laboratories, Pasching, Austria). Molecular weight standards (BSA, Thermo Scientific; Waltham, Mass., USA) and a placebo buffer were run in each sequence. Quantification of aggregation and fragmentation in % was determined by comparing the area under the curves of the monomer peaks, the sum of the high molecular weight species and the sum of the low molecular weight species.

Irradiation Protocols

Sterilization was performed by Sterigenics (Leuven, Belgium) using β- or γ-irradiation at 25 or 40 kGy. As a modification to the standard irradiation protocols, part of the samples was irradiated at −80° C.

Dialysis

Anti ErbB2 antibody (20 mg/mL) was dialyzed overnight against SPS (40 mg/mL) pH 6, original formulation and Dulbecco's PBS adjusted to a pH of 6 using Slide-A-Lyzer® dialysis cassettes (cutoff 3.5 kDa; volume 3-12 mL) purchased from Thermo Scientific. Dialysis was performed immediately prior to lyophilization to ensure optimal stability. A part of the antibody samples were dialyzed for re-buffering in SPS or PBS.

Lyophilization

Lyophilization was done with an EPSILON 2-6D (Martin Christ; Osterode am Harz, Germany) according to the protocol shown in Table 2 below:

TABLE 2

Lyophilization protocol

| Protocol Step | Target T (° C.) | Slope (h) | Hold (h) | Pressure (mbar) |
|---|---|---|---|---|
| Introduction | 20 | 0 | 0 | 1000 |
| Freezing | −50 | 1:30 | 2:30 | 1000 |
| Sublimation | −50 | 0:15 | 0 | 0.045 |
|  | −15 | 1:30 | 30:00 | 0.045 |
| Secondary | −15 | 0:15 | 0 | 0.009 |
| Drying | 20 | 1:30 | 10:00 | 0.009 |

Data Analysis.

All experiments were done at least in triplicates and data are depicted as Mean±SD. SigmaStat 3.0 was used to conduct nonparametric analyses using Mann-Whitney Rank Sum Test. Differences were considered significant at $p<0.01$.

10.2 the Effect of Irradiation on ErbB2 Recognition

An anti ErbB2 ELISA was established in order to study the impact of irradiation on functional antigen binding. FIG. 17 depicts the standard curve established with immobilized recombinant ErbB2 and freshly reconstituted anti ErbB2 antibody. By means of the standard curve, 20 ng/mL the anti ErbB2 antibody was selected as the standard concentration for the following experiments.

The functional activity of the stressed anti ErbB2 antibody samples was compared with the functional activity of freshly reconstituted original anti ErbB2 antibody which was defined as the 100% positive control. When anti ErbB2 antibody was re-buffered in SPS, lyophilized and tested in the ELISA, antigen binding was 115±13.7% whereas samples re-buffered in the original buffer antigen binding was 95±5.2% (FIG. 2). After β- and γ irradiation at 25 kGy, we found almost 100% binding activity in the SPS-formulated samples and between 83.2±6.4% and 87.4±1.9% for the original buffers. When samples were treated with 40 kGy, the activity ranged between 93.0±2.1% and 102.6±5.1% in SPS-formulated samples whereas binding activity was in the range between 63.19±2.1% and 71.8±4.5% for the original buffers (FIG. 16).

10.3 the Effect of Irradiation on the Formation of Aggregates and Fragments

To analyze the integrity of the molecular structure of the therapeutic anti ErbB2 IgG1 antibody after irradiation, the aggregation status of irradiated samples was compared with controls. The aggregate content of therapeutically applied biologics should be as low as possible (e.g. below 2%) and is a crucial parameter for regulatory compliance. By means of semi-quantitative non-reducing SDS-PAGE (FIG. 18) and a fluorescence-based microplate assay (FIG. 19), substantial formation of aggregates and degradation products of anti ErbB2 antibody were observed following both 25 and 40 kGy β- and γ-irradiation. When samples were lyophilized and irradiated in SPS, irradiation-mediated aggregates and degradation products were found to be markedly reduced. This semi-quantitative observation was confirmed by size exclusion chromatography (SEC) analysis (FIG. 20). Selected chromatograms obtained for the irradiated samples with SPS formulation, compared with the original formulation and with PBS (negative control) are depicted in FIGS. 20A and 20B (zoomed). The main peak corresponding to the intact IgG1 monomer (M) with a molecular weight of approx. 160 kDa elutes at a retention volume of 8.5 mL. The elution range of high molecular weight aggregates (HMW) consisting of dimers, trimers, tetramers and possibly higher molecular weight aggregates of the IgG monomer lies between 5.5 and 8 mL. Only a small propensity for fragmentation was observed between retention volumes of 10-11 mL in form of low molecular weight species (LMW). The values for the percentages of HMW, LMW, and monomers (M) are listed in Table 3. In all experiments, the SPS formulation resulted in an up to 20-fold reduction of aggregates and degradation products ($p<0.05$).

TABLE 3

Percentage of anti ErbB2 IgG1 monomers, aggregates, and fragments with and without different irradiation protocols

|  |  | Monomers [%] | | | Aggregates [%] | | | Fragments [%] | | |
|---|---|---|---|---|---|---|---|---|---|---|
|  |  | Original | SPS | PBS | Original | SPS | PBS | Original | SPS | PBS |
| 4° C. | original | 99.4 | n.a. | n.a. | 0.6 | n.a. | n.a. | 0 | n.a. | n.a. |
| RT | no irradiation | 99.0 | 98.8 | 99.0 | 1.0 | 1.0 | 1.0 | 0.0 | 0.2 | 0.0 |
|  | 25 kGy -β | 87.1 | 98 | 73.2 | 11.5 | 1.7 | 25.2 | 1.4 | 0.3 | 1.6 |

TABLE 3-continued

Percentage of anti ErbB2 IgG1 monomers, aggregates, and fragments with and without different irradiation protocols

| | Monomers [%] | | | Aggregates [%] | | | Fragments [%] | | |
|---|---|---|---|---|---|---|---|---|---|
| | Original | SPS | PBS | Original | SPS | PBS | Original | SPS | PBS |
| 25 kGy -γ | 84.5 | 98 | 68.8 | 13.6 | 1.7 | 30.7 | 1.9 | 0.3 | 0.5 |
| 40 kGy - β | 81.7 | 97.8 | 65.2 | 16.3 | 1.8 | 33.7 | 2.0 | 0.4 | 1.1 |
| 40 kGy - γ | 79.8 | 97.3 | 60.3 | 17.5 | 2.2 | 38.7 | 2.7 | 0.5 | 1.0 |

10.4 Freeze-Drying Mediated Changes in Secondary Structures is Prevented by SPS.

To study the secondary structure of the freeze-dried molecules, FT-IR analysis was carried out (FIG. 21). No changes in the amid-I-absorption band at 1638 cm-1 were detected in all spectra. However, the spectra of the dried antibodies formulated in the original formulation and in the negative control PBS showed considerably changes in both the peak position and form of the amid-II-absorption band at 1547 cm−1, suggesting a substantial loss of α-helical secondary structure content but not in the β-sheet content after lyophilization. For the dried SPS formulated antibodies no changes in the secondary structure were detected (FIG. 21 and Table 4).

TABLE 4

Calculated secondary structure content in percent from the monitored FT-IR spectra

| Sample | α-helix [%] | β-sheet [%] |
|---|---|---|
| Dried anti-ErbB2 IgG1 in SPS | 8.8 ± 1.3 | 55.8 ± 2.8 |
| Dried anti-ErbB2 IgG1 in original formulation | 0 | 51.2 ± 1.2 |
| Dried anti-ErbB2 IgG1 in PBS | 0 | 49.9 ± 1.1 |
| Freshly reconstituted anti-ErbB2 IgG1 Control | 3.0 ± 0.4 | 51.8 ± 0.7 |

Thus, these examples revealed significant aggregation in samples which were formulated with the original supplier formulation and with PBS upon analysis of irradiated samples by SDS-PAGE and by a fluorescent aggregation assay. Aggregate formation is a severe risk for patients because it might provoke side effects and unappreciated immune response. During production and storage of therapeutic proteins it is therefore crucial to retain a high percentage of monomers. It could be shown, that this important goal can be reached when the therapeutic anti-ErbB2 IgG1 antibody is reformulated in SPS.

SEC analysis showed that either irradiation type induced severe aggregation and degradation of the therapeutic anti-ErbB2 IgG1 antibody in the original formulation but not in SPS-formulated samples, thus confirming the findings by SDS-PAGE and fluorescent aggregation tests. Interestingly, even after irradiation at 40 kGy SPS-formulated biomolecules reached this goal and the content of high molecular weight aggregates was around 2% or less.

Example 11: Embedding of a Human Anti-IL6-IgG Antibody Adsorbed on a Surface in Different Compositions of the Protecting Solution Protection of a human anti-IL6-IgG antibody by a variety of different compositions of the protecting solution according to the invention against 40 kGy β irradiation was analyzed.

After coating a 96 well ELISA plate with a human anti-IL6-IgG antibody, the protecting solution was added to each well and subsequent vacuum drying of the plates was performed. The dried plates were β-irradiated at 40 kGy and the antigen binding activity was measured in the corresponding anti-IL6-ELISA. Specific binding of recombinant human IL-6 to the anti-IL6-IgG antibody was detected photometrically by enzymatic conversion of the horseradish peroxidase substrate TMB at 450 nm. In FIG. 22 the antigen binding activity in percent of the untreated control is depicted. Compositions with seven amino acids (amino acid mixture 1: Ala, Arg, Gly, Glu, Lys, His, Trp) or with five amino acids (amino acid mixture 2: Ala, Arg, Gly, Glu, Lys and amino acid mixture 3: Ala, Gly, Glu, His, Trp, respectively) were used. The experiments revealed that the exclusion of amino acids that may have unappreciated side effects upon prolonged storage (oxidation sensitive; hygroscopic) resulted in reduced protective effects. When GA and/or carnosine, and/or dipeptides (Gly-Tyr, Gly-GLy, Gly-Gln) were supplemented to these compositions, the protecting effects of the composition could be increased.

Supplementation of glycyrrhizic acid to the amino acid mixtures, particularly in combination with the dipeptide carnosin, and other dipeptides resulted in a rescue of the irradiation mediated loss of function to varying degrees (Table 5).

TABLE 5

Compositions of the applied formulations 1-16 without and in combination with glycyrrhizic acid in stabilizing the immobilized anti-IL6-IgG antibody after vacuum drying against 40 kGy β irradiation

| | Amino acids | Supplements |
|---|---|---|
| Formulation 1 | Ala, Arg, Gly, Glu, Lys, His, Trp | |
| Formulation 2 | Ala, Arg, Gly, Glu, Lys, | |
| Formulation 3 | Ala, Gly, Glu, His, Trp | |
| Formulation 4 | Ala, Arg, Gly, Glu, Lys | carnosin concentration <5% |
| Formulation 5 | Ala, Arg, Gly, Glu, Lys | carnosin concentration <10% |
| Formulation 6 | Ala, Arg, Gly, Glu, Lys | carnosin concentration <12% |
| Formulation 7 | Ala, Arg, Gly, Glu, Lys | carnosin concentration <18% |
| Formulation 8 | Ala, Arg, Gly, Glu, Lys | carnosin concentration <20% |
| Formulation 9 | Ala, Arg, Gly, Glu, Lys, Trp | carnosin |
| Formulation 10 | Ala, Arg, Gly, Glu, Lys | carnosin, N-acetyl-Trp |
| Formulation 11 | Ala, Arg, Gly, Glu, Lys, Trp | His, β-alanine (single components of carnosin) |
| Formulation 12 | Ala, Arg, Gly, Glu, Lys | N-acetyl-Trp, N-acetyl-His, β-alanine |
| Formulation 13 | Ala, Arg, Gly, Glu, Lys | Gly-Gly, Gly-Gln |
| Formulation 14 | Ala, Arg, Gly, Glu, Lys | Carnosin, Gly-Gly, N-acetyl-Trp, N-acetyl-His |
| Formulation 15 | Ala, Arg, Gly, Glu, Lys | Carnosin, Gly-Gln, N-acetyl-Trp, N-acetyl-His |
| Formulation 16 | Ala, Arg, Gly, Glu, Lys | Gly-Tyr, Gly-Gly, Gly-Gln |

Example 12: Retention of Enzymatic Activity of Recombinant Lactic Dehydrogenase Dried in Combination with Different Compositions of the Protecting Solutions Against β Irradiation Lyophilized recombinant lactic dehydrogenase (LDH) was dissolved in a variety of different compositions of the protecting solution according to the present invention in enzyme/excipient ratios of approx. 1:2,5 and subsequently freeze dried. Freeze drying was done in 100 µl volumes and the dried samples were β irradiated at 40 kGy. After reconstitution of the samples, enzymatic LDH activity was measured photometrically by monitoring the decrease of the absorption of the enzyme's reduced cofactor NADH at 340 nm upon its oxidation to NADH$^+$ and the simultaneously reduction of the substrate pyruvate to lactate. The enzymatic activity is depicted in percent of the untreated control. Compositions with seven amino acids (amino acid mixture 1: Ala, Arg, Gly, Glu, Lys, His, Trp) or with five amino acids (amino acid mixture 2: Ala, Arg, Gly, Glu, Lys) were used. Supplementation of glycyrrhizic acid to the amino acid mixtures, particularly in combination with the dipeptide carnosin, and other dipeptides resulted in a rescue of the irradiation mediated loss of function to varying degrees (Table 6).

TABLE 6

Compositions of the applied formulations 1-8 without and in combination with glycyrrhizic acid in stabilizing the freeze dried enzyme lactic dehydrogenase against 40 kGy β irradiation.

| | Amino acids | Supplements |
|---|---|---|
| Formulation 1 | Ala, Arg, Gly, Glu, Lys | |
| Formulation 2 | Ala, Arg, Gly, Glu, Lys | carnosin concentration <5% |
| Formulation 3 | Ala, Arg, Gly, Glu, Lys | carnosin concentration <10% |
| Formulation 4 | Ala, Arg, Gly, Glu, Lys, | His, β-alanine, N-acetyl-Trp, |
| Formulation 5 | Ala, Arg, Gly, Glu, Lys, Trp | N-acetyl-His, β-alanine, |
| Formulation 6 | Ala, Arg, Gly, Glu, Lys | Carnosin, Gly-Tyr |
| Formulation 7 | Ala, Arg, Gly, Glu, Lys | Gly-Tyr, Gly-Gly, |
| Formulation 8 | Ala, Arg, Gly, Glu, Lys | Gly-Tyr, Gly-Gly, Gly-Gln |

Example 13: Hemagglutination Activity of an Inactivated Influenza A H1N1 Split Vaccine was Retained Upon Freeze Drying and 40 kGy β-Irradiation of the Dried Formulations Monitored by Hemagglutination Assay The original supplier formulation of an inactivated influenza A H1N1 split vaccine was exchanged at 2 to 8° C. versus different compositions of the protecting solution according to the present invention. The w/w (vaccine/excipients of the protecting solution) ratio was between approx. 1:50 and 1:12.5. Freeze drying was done in 100 μl volumes and lyophilisates were irradiated with 40 kGy β-irradiation.

After irradiation and reconstitution, the functionality of the samples was evaluated in the hemagglutination assay (HA). As shown in FIG. 24, in contrast to the influenza A split vaccine freeze dried in the original supplier formulation, which showed a complete loss of hemagglutination activity already after freeze drying, the hemagglutination activity was almost fully maintained after reconstitution of influenza A split vaccine freeze dried in different compositions of the inventive solution.

Moreover, the hemagglutination activities of the freeze dried samples formulated in a variety of different compositions of the protecting solution according to this invention were almost fully maintained after 40 kGy β-irradiation and reconstitution of the dried samples compared to the activities before and after freeze drying. Compositions with seven amino acids (amino acid mixture 1; Ala, Arg, Glu, Gly, Lys, His, Trp) or with five amino acids (amino acid mixture 2; Ala, Arg, Glu, Gly, Lys and amino acid mixture 3: Ala, Gly, Glu, His, Trp, respectively) were used. Compositions containing the dipeptide carnosine, glycyrrhizic acid, additional dipeptides, and combinations thereof, resulted in the best protection against lyophilisation-mediated and/or irradiation-mediated loss of functionality (Table 7). After the substitution of selected amino acids with dipeptides and/or GA the osmolarity of the composition is lower and may therefore be beneficial for therapeutical purposes.

TABLE 7

Compositions of the applied formulations 1-18 in stabilizing the inactivated influenza A H1N1 split vaccine against different types of stresses.

| | Amino acids | Supplements |
|---|---|---|
| Formulation 1 | Ala, Arg, Gly, Glu, Lys, His, Trp | |
| Formulation 2 | Ala, Gly, Glu, His, Trp | |
| Formulation 3 | Ala, Arg, Gly, Glu, Lys | Carnosin, N-acetyl-Trp |
| Formulation 4 | Ala, Arg, Gly, Glu, Lys, Trp | Carnosin, glycyrrhizic acid |
| Formulation 5 | Ala, Arg, Gly, Glu, Lys, His | N-acetyl-Trp, β-alanine |
| Formulation 6 | Ala, Arg, Gly, Glu, Lys | Carnosin, Gly-Tyr, N-acetyl-Trp, N-acetyl-His |
| Formulation 7 | Ala, Arg, Gly, Glu, Lys | Carnosin, Gly-Tyr, Gly-Gly, Gly-Gln |
| Formulation 8 | Ala, Arg, Gly, Glu, Lys | Gly-Tyr, Gly-Gly, Gly-Gln |
| Formulation 9 | Ala, Arg, Gly, Glu, Lys | N-acetyl-Trp, N-acetyl-His, β-alanine, glycyrrhizic acid |
| Formulation 10 | Ala, Arg, Gly, Glu, Lys | Carnosin, Gly-Tyr, glycyrrhizic acid |
| Formulation 11 | Ala, Arg, Gly, Glu, Lys | Gly-Tyr, Gly-Gly, glycyrrhizic acid |
| Formulation 12 | Ala, Arg, Gly, Glu, Lys | Gly-Gly, Gly-Gln, glycyrrhizic acid |
| Formulation 13 | Ala, Arg, Gly, Glu, Lys | Carnosin, Gly-Tyr, N-acetyl-Trp, N-acetyl-His, glycyrrhizic acid |
| Formulation 14 | Ala, Arg, Gly, Glu, Lys | Carnosin, Gly-Gly, N-acetyl-Trp, N-acetyl-His, glycyrrhizic acid |
| Formulation 15 | Ala, Arg, Gly, Glu, Lys | Carnosin, Gly-Gln, N-acetyl-Trp, N-acetyl-His, glycyrrhizic acid |
| Formulation 16 | Ala, Arg, Gly, Glu, Lys | Carnosin, Gly-Tyr, Gly-Gly, Gly-Gln, glycyrrhizic acid |
| Formulation 17 | Ala, Arg, Gly, Glu, Lys | Carnosin, N-acetyl-Trp, Gly-Tyr, Gly-Gly, Gly-Gln, glycyrrhizic acid |
| Formulation 18 | Ala, Arg, Gly, Glu, Lys | Gly-Tyr, Gly-Gly, Gly-Gln, glycyrrhizic acid |

REFERENCES

Arakawa, T., et al. "Factors Affecting Short-Term and Long-Term Stabilities of Proteins." Adv Drug Deliv Rev 46.1-3 (2001): 307-26.

Arakawa, T., et al. "Biotechnology Applications of Amino Acids in Protein Purification and Formulations." Amino Acids 33.4 (2007): 587-605.

Arnold, J. N., et al. "Human Serum Igm Glycosylation: Identification of Glycoforms That Can Bind to Mannan-Binding Lectin." J Biol Chem 280.32 (2005): 29080-7.

Auton, M., D. W. Bolen, and J. Rosgen. "Structural Thermodynamics of Protein Preferential Solvation: Osmolyte Solvation of Proteins, Aminoacids, and Peptides." Proteins 73.4 (2008): 802-13.

Baltina, L. A. "Chemical Modification of Glycyrrhizic Acid as a Route to New Bioactive Compounds for Medicine." Curr Med Chem 10.2 (2003): 155-71.

Brandt, O, U Dietrich, and J Koch. "Solid-Supported Peptide Arrays in the Investigation of Protein-Protein and Protein-Nucleic Acid Interactions." Curr Chem Biol 3 (2009): 171-79.

Brinston, R., A. Miller, and C. Deeley. "Developments in Radiation Sterilisation." Med Device Technol 19.2 (2008): 36-7.

Fadeel, B., et al. "A Three-Dimensional Model of the Fas/Apo-1 Molecule: Cross-Reactivity of Anti-Fas Antibodies Explained by Structural Mimicry of Antigenic Sites." Int Immunol 10.2 (1998): 131-40.

Feyen, O., Lueking, A., Kowald, A., Stephan, C. et al., Off-target activity of TNF-alpha inhibitors characterized by protein biochips. Analytical and bioanalytical chemistry 2008,391,1713-1720.

Fong, W. L., and G. W. Grimley. "Peripheral Intravenous Infusion of Amino Acids." Am J Hosp Pharm 38.5 (1981): 652-9.

Fuchs, H., et al. "Saponins as Tool for Improved Targeted Tumor Therapies." Curr Drug Targets 10.2 (2009): 140-51.

Garrison, W. M., M. E. Jayko, and W. Bennett. "Radiation-Induced Oxidation of Protein in Aqueous Solution." Radiat Res 16 (1962): 483-502.

Gianfreda, L., and M. R. Scarfi. "Enzyme Stabilization: State of the Art." Mol Cell Biochem 100.2 (1991): 97-128.

Han, Q., et al. "The Promotion of Neural Regeneration in an Extreme Rat Spinal Cord Injury Model Using a Collagen Scaffold Containing a Collagen Binding Neuroprotective Protein and an Egfr Neutralizing Antibody." Biomaterials 31.35 (2010): 9212-20.

Han, Y., et al. "Effects of Sugar Additives on Protein Stability of Recombinant Human Serum Albumin During Lyophilization and Storage." Arch Pharm Res 30.9 (2007): 1124-31.

Hilpert, K., D. F. Winkler, and R. E. Hancock. "Peptide Arrays on Cellulose Support: Spot Synthesis, a Time and Cost Efficient Method for Synthesis of Large Numbers of Peptides in a Parallel and Addressable Fashion." Nat Protoc 2.6 (2007): 1333-49.

Horejs, C., et al. "Atomistic Structure of Monomolecular Surface Layer Self-Assemblies: Toward Functionalized Nanostructures." ACS Nano 5.3 (2011): 2288-97.

Horejs, C., et al. "Surface Layer Protein Characterization by Small Angle X-Ray Scattering and a Fractal Mean Force Concept: From Protein Structure to Nanodisk Assemblies." J Chem Phys 133.17 (2010): 2288-97.

Hosper, N. A., et al. "Intra-Uterine Tissue Engineering of Full-Thickness Skin Defects in a Fetal Sheep Model." Biomaterials 31.14 (2010): 3910-9.

Hoxey, E., et al. "Revised Standards for Sterilisation: The Changes." Med Device Technol 18.2 (2007): 33-38.

Hupcey, M. A., and S. Ekins. "Improving the Drug Selection and Development Process for Combination Devices." Drug Discov Today 12.19-20 (2007): 844-52.

Jain, N. K., and I. Roy. "Effect of Trehalose on Protein Structure." Protein Sci 18.1 (2009): 24-36.

Jorgensen, L., et al. "Recent Trends in Stabilising Peptides and Proteins in Pharmaceutical Formulation—Considerations in the Choice of Excipients." Expert Opin Drug Deliv 6.11 (2009): 1219-30.

Kapoor, S., and K. I. Priyadarsini. "Protection of Radiation-Induced Protein Damage by Curcumin." Biophys Chem 92.1-2 (2001): 119-26.

Kim, I. S., et al. "Dry-Heat Treatment Process for Enhancing Viral Safety of an Antihemophilic Factor Viii Concentrate Prepared from Human Plasma." J Microbiol Biotechnol 18.5 (2008): 997-1003.

Koch, J, and M Mahler. "Peptide Arrays on Membrane Supports." Springer, Heidelberg (2002).

Lueking, A., Beator, J., Patz, E., Müllner, S. et al., Determination and validation of off-target activities of anti-CD44 variant 6 antibodies using protein biochips and tissue microarrays. BioTechniques. 2008,45:Pi-v.

Lueking, A., Huber, O., Wirths, C., Schulte, K. et al., Profiling of alopecia areata autoantigens based on protein microarray technology. Molecular & cellular proteomics. 2005,4,1382-1390.

Logters, T. T., et al. "Extracorporeal Immune Therapy with Immobilized Agonistic Anti-Fas Antibodies Leads to Transient Reduction of Circulating Neutrophil Numbers and Limits Tissue Damage after Hemorrhagic Shock/Resuscitation in a Porcine Model." J Inflamm (Lond) 7 (2010): 18.

Masefield, J., and R. Brinston. "Radiation Sterilisation of Advanced Drug-Device Combination Products." Med Device Technol 18.2 (2007): 12-4, 16.

Nicoletti, I., et al. "A Rapid and Simple Method for Measuring Thymocyte Apoptosis by Propidium Iodide Staining and Flow Cytometry." J Immunol Methods 139.2 (1991): 271-9.

Paunel-Gorgulu, A., et al. "Stimulation of Fas Signaling Down-Regulates Activity of Neutrophils from Major Trauma Patients with Sirs." Immunobiology 216.3 (2011): 334-42.

Paunel-Gorgulu, A., et al. "Mcl-1-Mediated Impairment of the Intrinsic Apoptosis Pathway in Circulating Neutrophils from Critically Ill Patients Can Be Overcome by Fas Stimulation." J Immunol 183.10 (2009): 6198-206.

Perkins, S. J., et al. "Solution Structure of Human and Mouse Immunoglobulin M by Synchrotron X-Ray Scattering and Molecular Graphics Modelling. A Possible Mechanism for Complement Activation." J Mol Biol 221.4 (1991): 1345-66.

Peter, M. E., et al. "The Cd95 Receptor: Apoptosis Revisited." Cell 129.3 (2007): 447-50.

Ratner, M. "Reality Check for Device-Drug Convergence." Nat Biotechnol 25.2 (2007): 157-9.

Sauerbrei, A., et al. "Hexon Denaturation of Human Adenoviruses by Different Groups of Biocides." J Hosp Infect 65.3 (2007): 264-70.

Sawyer, A. A., et al. "The Stimulation of Healing within a Rat Calvarial Defect by Mpcl-Tcp/Collagen Scaffolds Loaded with Rhbmp-2." Biomaterials 30.13 (2009): 2479-88.

Schneider, P., et al. "Characterization of Fas (Apo-1, Cd95)-Fas Ligand Interaction." J Biol Chem 272.30 (1997): 18827-33.

Scholz, M., and J. Cinatl. "Fas/Fasl Interaction: A Novel Immune Therapy Approach with Immobilized Biologicals." Med Res Rev 25.3 (2005): 331-42.

Scholz, M., et al. "First Efficacy and Safety Results with the Antibody Containing Leukocyte Inhibition Module in Cardiac Surgery Patients with Neutrophil Hyperactivity." Asaio J 51.2 (2005): 144-7.

Shmulewitz, A., and R. Langer. "The Ascendance of Combination Products." Nat Biotechnol 24.3 (2006): 277-80.

Stadtman, E. R., and R. L. Levine. "Protein Oxidation." Annals of the New York Academy of Sciences 899 (2000): 191-208.

Timasheff, S. N. "The Control of Protein Stability and Association by Weak Interactions with Water: How Do Solvents Affect These Processes?" Annu Rev Biophys Biomol Struct 22 (1993): 67-97.

Woolston, J. "Radiation Processing: Adapting to a Changing World." Med Device Technol 20.1 (2009): 14-7.

Zamzami, N., and G. Kroemer. "Condensed Matter in Cell Death." Nature 401.6749 (1999): 127-8.

Zbikowska, H. M., P. Nowak, and B. Wachowicz. "Protein Modification Caused by a High Dose of Gamma Irradiation in Cryo-Sterilized Plasma: Protective Effects of Ascorbate." Free Radical Biology & Medicine 40.3 (2006): 536-42.

The invention claimed is:

1. A method for inhibiting the unfolding of a polypeptide during drying and/or inducing the refolding of a polypeptide after drying, comprising the steps of:
   (A) dissolving the polypeptide in an aqueous solution, wherein the solution comprises at least three different amino acids in an amount effective to inhibit the unfolding of a polypeptide during and/or inducing the refolding of a polypeptide after drying, wherein the at least three different amino acids are selected from at least three different groups of:
      (a) amino acids with nonpolar, aliphatic R groups selected from alanine or glycine;
      (b) an amino acid with a polar, uncharged R group which is threonine;
      (c) amino acids with positively charged R groups selected from arginine, histidine or lysine;
      (d) amino acids with negatively charged R groups selected from glutamate or aspartate; and
      (e) amino acids with aromatic R groups selected from tryptophan or histidine;
   and wherein the solution is free or substantially free of
      (1) sugar, protein and silanes; or
      (2) sugar, denaturing compounds and silanes; or
      (3) sugar, protein, denaturing compounds and silanes; and
   (B) drying the polypeptide,
      wherein step (A) is performed before or after step (B).

2. The method of claim 1, wherein the at least three different amino acids do not include:
   (i-a) a combination of glutamate and glutamine, and/or
   (i-b) a combination of aspartate and asparagine.

3. The method according to claim 1, wherein the solution comprises at least the amino acids:
   (a) alanine, glutamate, lysine, threonine and tryptophan;
   (b) arginine, glycine, histidine, alanine, glutamate, lysine and tryptophan; or
   c) alanine, arginine, glycine, glutamate, and lysine.

4. The method according to claim 1, wherein at least one of the amino acids is selected from the group consisting of natural non-proteinogenic amino acids and synthetic amino acids.

5. The method according to claim 1, wherein the w/w ratio between the amino acids of the solution and the polypeptide is between 1:1 and 500:1.

6. The method according to claim 1, wherein the polypeptide is a recombinant polypeptide.

7. The method according to claim 1, wherein the polypeptide has one or more intra-molecular disulfide bonds.

8. The method according to claim 1, wherein the refolded polypeptide is biologically active.

9. The method according to claim 1, wherein the drying is freeze-drying, air-drying, spray-drying, spray-freeze-drying or foam drying.

10. The method according to claim 1, wherein the aqueous solution in step (A) further comprises at least one dipeptide selected from the group consisting of carnosine, glycyltyrosine, glycylglycine and glycyl-glutamine.

11. The method of claim 1, wherein the method further comprises the step of:
   (C) dissolving the dried polypeptide in a second aqueous solution to induce refolding of the polypeptide, wherein the second aqueous solution is different from the aqueous solution of step (A), and wherein step (A) is performed prior to step (B).

12. The method of claim 1, wherein the aqueous solution comprises at least one amino acid selected from each group of:
   (a) an amino acid with nonpolar, aliphatic R groups;
   (b) an amino acid with polar, uncharged R groups;
   (c) an amino acid with positively charged R groups;
   (d) an amino acid with negatively charged R groups; and
   (e) an amino acid with aromatic R groups.

* * * * *